United States Patent
Ylera

(10) Patent No.: US 11,453,883 B2
(45) Date of Patent: Sep. 27, 2022

(54) DISPLAY SYSTEMS FOR PROTEINS OF INTEREST

(71) Applicant: BIO-RAD ABD SEROTEC GMBH, Puchheim (DE)

(72) Inventor: Francisco Ylera, Munich (DE)

(73) Assignee: BIO-RAD ABD SEROTEC GMBH, Puchheim (DE)

(*) Notice: Subject to any disclaimer, the term of this patent is extended or adjusted under 35 U.S.C. 154(b) by 1 day.

(21) Appl. No.: 16/375,894

(22) Filed: Apr. 5, 2019

(65) Prior Publication Data

US 2019/0309312 A1  Oct. 10, 2019

Related U.S. Application Data

(60) Provisional application No. 62/652,938, filed on Apr. 5, 2018.

(51) Int. Cl.
| | |
|---|---|
| *C12N 15/00* | (2006.01) |
| *C12N 15/70* | (2006.01) |
| *C07K 16/24* | (2006.01) |
| *C07K 16/32* | (2006.01) |
| *C12N 7/00* | (2006.01) |
| *C12N 15/85* | (2006.01) |
| *C12N 15/10* | (2006.01) |
| *C07K 19/00* | (2006.01) |

(52) U.S. Cl.
CPC ............ *C12N 15/70* (2013.01); *C07K 16/241* (2013.01); *C07K 16/32* (2013.01); *C07K 19/00* (2013.01); *C12N 7/00* (2013.01); *C12N 15/1037* (2013.01); *C12N 15/85* (2013.01); *C07K 2317/21* (2013.01); *C07K 2317/24* (2013.01); *C07K 2317/55* (2013.01); *C12N 2795/00051* (2013.01)

(58) Field of Classification Search
CPC ...................................................... C12N 15/70
See application file for complete search history.

(56) References Cited

U.S. PATENT DOCUMENTS

| | | | | |
|---|---|---|---|---|
| 5,616,686 | A | * | 4/1997 | Fischetti ................ C07K 14/31 530/326 |
| 6,753,136 | B2 | | 6/2004 | Lohning |
| 7,785,859 | B2 | | 8/2010 | Lohning |
| 9,062,097 | B2 | | 6/2015 | Prassler et al. |
| 9,133,500 | B2 | | 9/2015 | Frisch et al. |
| 2018/0327446 | A1 | | 11/2018 | Fong et al. |
| 2020/0299358 | A1 | | 9/2020 | Knappik et al. |
| 2020/0299369 | A1 | | 9/2020 | Knappik |
| 2020/0299746 | A1 | | 9/2020 | Hentrich et al. |

FOREIGN PATENT DOCUMENTS

| | | |
|---|---|---|
| EP | 1144607 B1 | 12/2008 |
| EP | 2190987 B1 | 11/2012 |
| EP | 2534484 B1 | 11/2014 |
| WO | 2011/098772 A1 | 8/2011 |
| WO | WO 2013/045632 | 4/2013 |
| WO | WO 2013/171156 | 11/2013 |
| WO | WO 2017/058114 | 4/2017 |
| WO | WO 2017/070742 | 5/2017 |
| WO | WO 2018/220386 | 12/2018 |
| WO | WO 2019/006046 | 1/2019 |

OTHER PUBLICATIONS

Liu et al (Scientific Reports 4:7266, pp. 1-8) (Year: 2014).*
Brune et al (Scientific Reports 6:19234, pp. 1-13) (Year: 2016).*
Albrecht, Hugette et al. "Production of Soluble ScFvs with C-Terminal-Free Thiol for Site-Specific Conjugation or Stable Dimeric ScFvs on Demand," Bioconjugate Chem. Dec. 31, 2003, vol. 15, No. 1, pp. 16-26.
Fierer, Jacob O. et al. "SpyLigase peptide-peptide ligation polymerizes affibodies to enhance magnetic cancer cell capture," PNAS, 2014, pp. 1-6.
Mazor, Yariv et al. "Selection of full-length IgGs by tandem display on filamentous phage particles and Escherichia coli fluorescence-activated cell sorting screening," the FEBS Journal, Journal No. 227, 2010, pp. 2291-2303.
Nguyen et al. "Butelase 1 is an Asx-specific ligase enabling peptide macrocyclization and synthesis," nature chemical biology, vol. 10, Jul. 20, 2014, pp. 732-738.
Qi, Huan et al. "Phagemid Vectors for Phage Display: Properties, Characteristics and Construction," Journal of Molecular Biology, Jan. 30, 2012, vol. 417, pp. 129-143.
Reddignton, Samuel et al. Secrets of a covalent interaction for biomaterials and biotechnology: SpyTag and SpyCatcher, Current Opinion in Chemical Biology, Oct. 20, 2015, vol. 29, pp. 94-99.
Rondot, Susanne et al. "A helper phage to improve single-chain antibody presentation in phage display," Nature Biotechnology, Jan. 2001, vol. 19, pp. 75-78.

(Continued)

*Primary Examiner* — Albert M Navarro
*Assistant Examiner* — Mark Navarro
(74) *Attorney, Agent, or Firm* — Saliwanchik, Lloyd & Eisenschenk

(57) ABSTRACT

Described herein is a protein display selection method which uncouples a protein of interest (POI) library from the display selection system. Display of the POI can be achieved by forming a covalent bond between the POI and the anchor protein post expression either by enzymatic protein ligation (e.g. SpyLigase, SnoopLigase, sortase, butelase, peptiligase etc.) or by spontaneous covalent bond formation (e.g. Spy-Tag/SpyCatcher, SnoopTag/SnoopCatcher, etc.). The POI library is fused to a tethering sequence, for example SpyTag, at the C-terminus of the POI which then forms a covalent bond to a capture sequence found on an anchor protein, for example, the SpyCatcher-fused anchor protein, e.g., a Spy-Catcher-geneIII protein (SpyCatcher-pIII) fusion, for the most common form of phage display. Nucleic acid constructs, host cell systems and methods of producing the protein display systems are also provided.

21 Claims, 6 Drawing Sheets

Specification includes a Sequence Listing.

(56) References Cited

OTHER PUBLICATIONS

Rothe, Christine et al. "The Human Combinatorial Antibody Library HuCAL GOLD Combines Diversification of All Six CDRs According to the Natural Immune System with a Novel Display Method for Efficient Selection of High-Affinity Antibodies," J. Mol. Bio., 2008, vol. 376, pp. 1182-1200. (Available online: Dec. 15, 2017).
Thiel, Ilka V. et al. "An Atypical Naturally Split Intein Engineered for Highly Efficient Protein Labeling," Angew. Chem. Int. Ed., 2014, vol. 53, 1306-1310.
Toplak, Ana et al. "Peptiligase, an Enzyme for Efficient Chemoenzymatic Peptide Synthesis and Cyclization in Water," Adv. Synth. Catal. May 24, 2016, vol. 358, pp. 2140-2147.
Veggiani, Gianluca et al. "Programmable polyproteams built using twin peptide superglues," PNAS, Feb. 2, 2016, vol. 113, No. 5, pp. 1202-1207.
Wang, Kevin Caili et al. "Adapter-Directed Display: A Modular Design for Shutting Display on Phage Surfaces," J. Mol. Biol., Dec. 4, 2009,vol. 395, 1088-1101.
Ward, R.L. et al. "Retrieval of human antibodies from phage-display libraries using enzymatic cleavage," Journal of mmunological Methods, 1996, vol. 189, pp. 73-82.
Yumura, Kyohei et al. "Use of SpyTag/SpyCatcher to construct bispecific antibodies that target two epitopes of a single antigen," Oxford University Press on behalf of Japanese Biochemical Society, 2017, pp. 1-27.
Zakeri, Bijan et al. Peptide tag forming a rapid covalent bond to a protein, through engineering a bacterial adhesin, PNAS, vol. 109, No. 12, Mar. 20, 2012, pp. 4347-4348.
Schmohl, Lena et al. "Sortase-mediated ligations for the site-specific modification of proteins," Current Opinion in Chemical Biology, Oct. 6, 2014, vol. 22, pp. 122-128.
Siegmund, Vanessa et al. "Spontaneous Isopeptide Bond Formation as a Powerful Tool for Engineering Site-Specific Antibody-Drug Conjugates," Scientific Reports, Dec. 16, 2016, 6:39291, DOI:10. 103/srep39291, pp. 1-9.
Van den Berg van Saparoea, H. B. et al. "Display of Recombinant Proteins on Bacterial Outer Membrane Vesicles by Using Protein Ligation" *Applied and Environmental Microbiology,* Feb. 9, 2018, pp. 1-17, vol. 84, Issue 8, e02567-17.
Schmohl, L. et al. "Engineering sortase A by screening a second-generation library using phage display" *Journal of Peptide Science,* Feb. 10, 2017, pp. 631-635, Supporting Information pp. 1-14, vol. 23, Nos. 7-8.
Nguyen, H. D. et al. "Analysis and application of *Bacillus subtilis* sortases to anchor recombinant proteins on the cell wall" *AMB Express,* Jul. 21, 2011, pp. 1-11, vol. 1, No. 22.
Borodina, I. et al. "Disply of wasp venom allergens on the cell surface of *Saccharomyces cerevisiae*" Microbial Cell Factories, Sep. 24, 2010, pp. 1-13, vol. 9, No. 74.
Hatlem, D. et al. "Catching a SPY: Using the SpyCatcher-SpyTag and Related Systems for Labeling and Localizing Bacterial Proteins" *International Journal of Molecular Sciences,* Apr. 30, 2019, pp. 1-19, vol. 20, No. 9.
International Search Report and Written Opinion in International Application No. PCT/IB2019/000339, dated Sep. 13, 2019, pp. 1-22.
Alam, M. K. et al. "Site-Specific Fluorescent Labeling of Antibodies and Diabodies Using SpyTag/SpyCatcher System for In Vivo Optical Imaging" *Mol Imaging Biol.,* 2018, pp. 54-66, vol. 21.
Alam, M. K et al. "Synthetic Modular Antibody Construction Using the SpyTag/SpyCatcher Protein Ligase System" *ChemBioChem,* 2017, pp. 2217-2221, vol. 18, No. 22.
International Search Report and Written Opinion in International Application No. PCT/IB2020/000197, dated Aug. 28, 2020, pp. 1-18.
Keeble, A. H. et al. "Evolving Accelerated Amidation by SpyTag/SpyCatcher to Analyze Membrane Dynamics" *Ange. Chem. Int. Ed.,* 2017, pp. 16521-16525, vol. 56.
International Search Report and Written Opinion in International Application No. PCT/IB2020/000134, dated Aug. 27, 2020, pp. 1-18.
Meerman, H. et al. "Construction and Characterization of a Set of *E. coli* Strains Deficient in All Known Loci Affecting the Proteolytic Stability of Secreted Recombinant Proteins," *Biotechnology,* Nov. 23, 1994, pp. 1107-1110, vol. 12.
Chen, C. et al. "High-Level Accumulation of a Recombinant Antibody Fragment in the Periplasm of *Escherichia coli* Requires a Triple-Mutant (degP prc spr) Host Strain" *Biotechnology and Bioengineering,* published online Jan. 26, 2004, pp. 463-474, vol. 85, No. 5.
Ellis, M. et al. "Development of a High Yielding *E. coli* Periplasmic Expression System for the Production of Humanized Fab' Fragments" *Biotechnol. Prog.,* 2017, pp. 212-220, vol. 33, No. 1.
Alves, N. J. et al. "Bacterial Nanobioreactors-Directing Enzyme Packaging into Bacterial Outer Membrane Vesicles" *ACS Appl. Mater Interfaces,* 2015, pp. 24963-24972, vol. 7.
International Search Report and Written Opinion in International Application No. PCT/IB2020/000172, dated Jul. 27, 2020, pp. 1-18.
Zakeri, B. et al. "Peptide tag forming a rapid covalent bond to a protein, through engineering a bacterial adhesin" *PNAS,* published online Feb. 24, 2012, pp. E680-E697 and supporting pp. 1-19, vol. 109, No. 12.

\* cited by examiner

DISPLAY SYSTEMS FOR PROTEINS OF INTEREST

The Sequence Listing for this application is labeled "Seq-List-replace-2.txt" which was created on Nov. 30, 2021 and is 74 KB. The entire content of the sequence listing is incorporated herein by reference in its entirety.

BACKGROUND OF THE INVENTION

Phage Display

Selection of proteins with specific properties from large libraries is a well-established process. Phage display is the oldest and most commonly used selection method. It is based on the presentation of the protein of interest (POI) on the surface of phages which contain the corresponding DNA of the POI, for example, an antibody. For phage display, the POI is covalently linked to a phage coat protein. Most frequently, a genetic fusion to the gene III protein (pIII) of filamentous phage M13 is used but fusions to the other coat proteins have been in the literature as well. The POI-pIII fusion is usually cloned into a phagemid vector which contains an antibiotic resistance marker, origins of replication for phage and bacterial DNA polymerases, and a phage morphogenetic signal for the packaging of the phagemid into the phage (Qi et al., 2012).

The missing genes for phage production are supplied by infection with a helper phage, a full-length phage with a mutated packaging signal. Due to this mutation, predominantly the phagemid, and not the helper phage DNA, is packaged into the phage coat. These phages typically contain only one POI-pIII fusion on the surface since the wild-type pIII from the helper phage is incorporated faster than the fusion protein from the phagemid. The resulting monovalent protein display allows the selection for protein binding strength as it is not influenced by any avidity effects. Multivalent display can be achieved by using hyperphage, a modified helper phage which does not contain a wild-type gene III (gIII), therefore, all 5 copies of pIII have to originate from the phagemid (Rondot et al., 2001).

Instead of a genetic fusion between POI and pIII, it is also possible to connect the POI to the phage via a disulfide bond. In this system termed CysDisplay®, the pIII on the phagemid carries a cysteine at the N-terminus, and the POI has an additional cysteine at the C-terminus of the heavy chain (Rothe et al., 2008). Upon export to the periplasm, they form a disulfide bond and are incorporated into the phage coat. The advantage of CysDisplay® is the simple and quantitative elution of the specific phage POIs by cleavage of the disulfide bond with a reducing agent like DTT, a method that is independent of POI affinity. This avoids bias towards low-affinity POI, which are more readily eluted by conventional pH shift elution. A similar advantage can be achieved by a genetic fusion containing a protease cleavable linker (Ward et al., 1996). Non-covalent ways to display a POI on the pIII protein are the use of two dimerization domains (Wang et al., 2010) or the protein A ZZ domain (Mazor et al., 2010).

In phage display, selection is performed for typically 2 to 4 rounds to enrich clones that contain the desired properties like binding to a target or enzymatic activity. The selection output is then screened to identify the desired clones. For this step, the POI are usually expressed without the pIII most commonly by subcloning into an expression vector, by removing the gene III from the vector by restriction digest and re-ligation or by using an amber stop codon between the POI and the gIII in combination with *E. coli* strains lacking suppressor tRNAs. However, for expression of larger amounts, the POI is usually subcloned into an expression vector which gives higher yields than the amber stop codon system. This subcloning step is a laborious and time consuming step especially for high throughput selections against a multitude of targets in parallel.

Protein Ligation

Several technologies have been developed in recent years that enable covalent conjugation of polypeptides at specific pre-determined sites. One example is the sortase system (Schmohl et al., 2014), whereby a short peptide (the sorting motif) is genetically fused to the C-terminus of one polypeptide and two glycine residues are genetically fused to the N-terminus of a second peptide (or vice versa). In the presence of the sortase enzyme, the two modified polypeptides are fused together. A disadvantage of this system is the slow enzymatic reaction and the relatively low yield of end product that can be currently achieved. Other enzymatic protein ligase systems are butelase (Nguyen et al., 2014) or peptiligase (Toplak et al., 2016).

Another example is the in-frame addition of nucleotides encoding one or more cysteines to the C- or N termini of two polypeptides. When such free cysteine containing polypeptides are mixed under oxidizing conditions, they will form disulfide bridges. Such systems, however, suffer from the many side-products that will appear.

A third example is the so-called SpyTag/SpyCatcher (Reddington et al., 2015) system. Here, the concept of spontaneous isopeptide formation in naturally occurring proteins has been used to covalently attach one polypeptide to another. A domain from the *Streptococcus pyogenes* protein FbaB that contains such an isopeptide bond has been split into two parts. One part, the SpyTag, is a 13 amino acid peptide that contains part of the autocatalytic center. The other part, the SpyCatcher, is a 116 amino acid protein domain containing the other part of the center. It was shown that mixing those two polypeptides restores the autocatalytic center and leads to formation of the isopeptide bond, thereby covalently bind the SpyTag to the SpyCatcher (Zakeri et al., 2012). Further engineering has led to a shorter version of SpyCatcher with only 84 amino acids as well as an optimized version, SpyTag002 and SpyCatcher002 with accelerated reaction (Keeble et al., 2017; which is hereby incorporated by reference in its entirety). A further modification of the system was the invention of SpyLigase (Fierer et al., 2014), which was achieved by splitting the FbaB domain into three parts, the SpyTag, the K-tag and the SpyLigase. SpyTag and K-tag are both short peptides that are covalently fused by addition of SpyLigase.

BRIEF DESCRIPTION OF THE FIGURES

FIG. 2 provides an exemplary SpyCatcher-pIII sequence (SEQ ID NOs: 29 and 30).

FIG. 3A shows detection with anti-SpyCatcher antibody which can only detect the modified SpyCatcher phage but not the VCSM13 phage. FIG. 3*b* shows a Western blot with anti-pIII detection which gives a signal for both phages but shows a larger product (SpyCatcher-pIII fusion) for the SpyCatcher phages.

BRIEF DESCRIPTION OF THE INVENTION

Figure 1A:
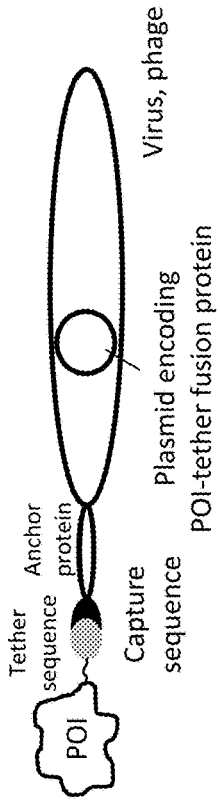
FIGS. 1A-1D provide an illustration of the phage and cell display (FIGS. 1A-1B) and the disclosed invention (FIGS. 1C-1D).
Figure 1B:
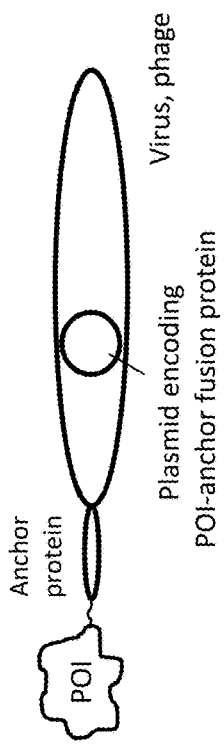
Figure 1C:
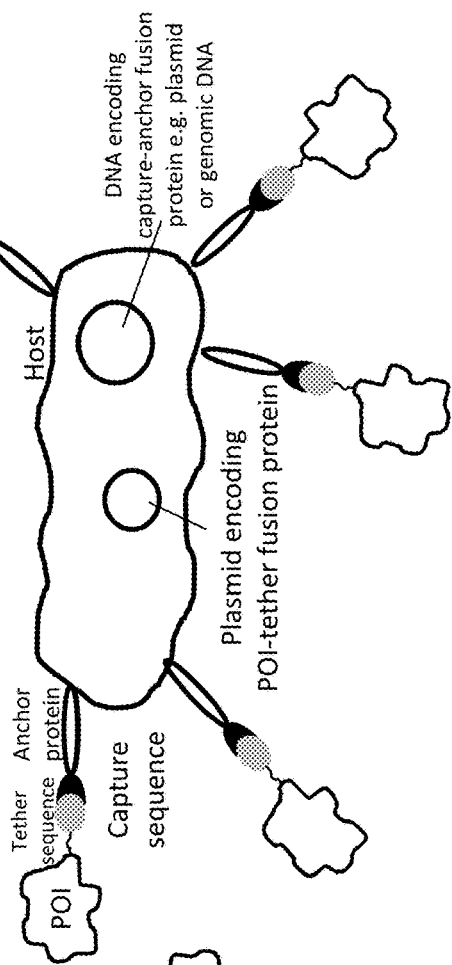
Figure 1D:
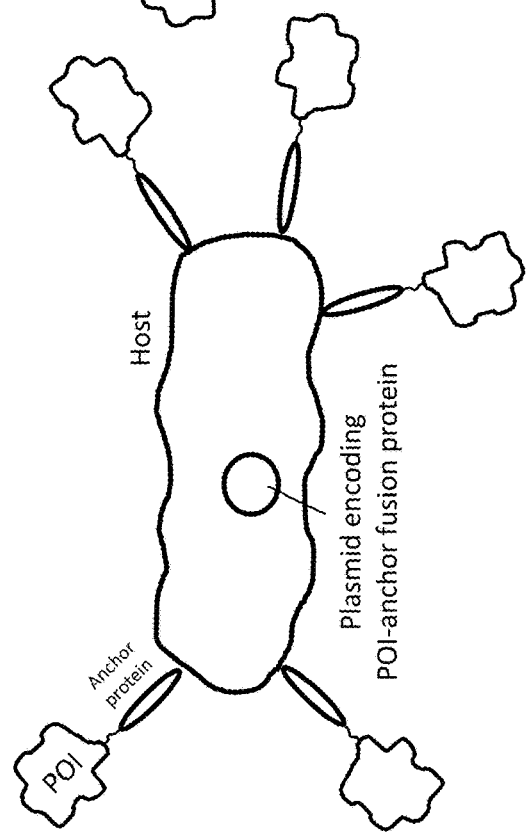

The invention described herein is a protein display selection method which uncouples the POI library from the display selection system. This is achieved by removing the fusion partner (e.g. gIIII protein in the case of phage display) from the library vector. Display of the POI can be achieved by forming a covalent bond between the POI and the anchor protein post expression either by enzymatic protein ligation (e.g. SpyLigase, SnoopLigase, sortase, butelase, peptiligase etc.) or by spontaneous covalent bond formation (e.g. SpyTag/SpyCatcher, SnoopTag/SnoopCatcher, etc.). The POI library is fused to a tethering sequence, for example SpyTag, at the C-terminus of the POI which then forms a covalent bond to a capture sequence found on an anchor protein, for example, the SpyCatcher-fused anchor protein, e.g., a SpyCatcher-geneIII protein (SpyCatcher-pIII) fusion, for the most common form of phage display. Alternatively, the POI is fused to the capture protein and the anchor protein is fused to the tether sequence. FIG. 1 provides a schematic representation of the disclosed invention.

To keep the library separate from the anchor protein, the capture-anchor protein gene is not encoded on the library phagemid but either by a modified helper phage, modified *E. coli* genome or an additional plasmid—for phage display or bacterial display—or by a modified expression host or additional plasmid for other display techniques.

The display system of this invention expresses the POI for the selection steps without modification i.e. without fusion to an anchor protein. Therefore, the expressed POI during selection is identical to the protein used for the following screening and production steps. Circumventing an artificial fusion (e.g., POI-pIII), which is required in conventional display selection systems, can avoid a bias in the selection introduced by different properties (expression, solubility, activity, stability, etc.) of a POI-anchor fusion protein. Furthermore, since the POI is not expressed as an anchor fusion protein, no subcloning step is required prior to screening and expression. This saves time and effort especially in high throughput selection settings.

By keeping the library vector independent from the selection system, the library becomes usable for various display selection systems i.e. different coat proteins for phage display (coat proteins other than pIII) as well as other display systems (e.g., yeast display, mammalian or bacterial display) as long as the vector elements are compatible with the other host. The development of dual host vectors for switching from prokaryotic to eukaryotic expression systems have been described (e.g. Tesar et al. 2013, Batonick et al. 2016). The display system can also be switched within a selection between different selection rounds or after selection for screening e.g. of POI displayed on other hosts.

For phage display a high display rate of the POI on the phage is often beneficial in the first selection round. In standard phage display this can be achieved by using hyperphage without a gIII leaving the POI-pIII as the only source for pIII and thus producing phage with several POI on the phage surface. In the invention described here, a high display rate can be achieved by infecting *E. coli* containing the POI library with a modified helper phage which carries a SpyCatcher-gIII instead of gIII All copies of the pIII in the phage coat thus carry a SpyCatcher which enables protein ligation of several POI per phage. To achieve a monovalent display in the following rounds, to select for affinity rather than avidity, the selected phages of the first round are used to infect a modified *E. coli* strain which carries a SpyCatcher-gIII fusion in their genome or carries an additional plasmid for co-expression of SpyCatcher-gIII The SpyCatcher can be fused to a complete gIII (N1-N2-Ct) or to truncated or modified gIII (N2-Ct or Ct). After infection with helper phage, bacteria produce new phages which predominantly carry the wildtype pIII from the helper phage as it gets incorporated into the phage coat faster than the modified pIII from the *E. coli* genome/second plasmid. Alternatively, an additional SpyTag or a SpyTag fusion protein can be co-expressed which competes with the POI-SpyTag fusion for ligation with SpyCatcher which is introduced by the modified SpyCatcher-pIII helper phage. Instead of gIII other phage coat proteins can be used.

After the last selection round, non-modified *E. coli* which do not carry a SpyCatcher-fusion gene are infected with the phage output and can be used for screening and expression. The SpyTag at the C-terminus of the POI can be used for detection (with appropriate antibodies against the tag) as well as for conjugation with biotinylated, fluorescent- or enzyme-labelled SpyCatcher.

Thus, one embodiment of the envisioned invention consists of the POI-SpyTag fusion protein and the SpyCatcher-phage coat protein fusion, either produced by a modified *E. coli* strain, by a modified helper phage or co expressed by a second plasmid to display POI on the surface of phage.

In one embodiment, a POI-tethering sequence fusion protein is linked to a capture sequence-anchor fusion protein to display the POI on the surface of a biological entity. The capture sequence-anchor protein fusion is part of, or associated with, the outer surface of the biological entity and thus links the POI to the surface of the biological entity by formation of a covalent bond between the tethering sequence and the capture sequence. Furthermore, the biological entity contains the DNA which encodes the POI and thus provides a physical link of the POI and its DNA which is required for protein selection systems. In one non-limiting embodiment, the biological entity can be a phage with the capture sequence fused to a phage coat protein such as pIII-, pVI-, pVII-, pVIII- or pIX protein or an optimized, modified or truncated version of these coat proteins and the phagemid encoding the POI inside the phage coat. In other embodiments, the biological entity can be a yeast e.g., *Saccharomyces cerevisiae* or *Pichia pastoris* with the capture sequence fused to, e.g., the a-agglutinin yeast adhesion receptor, a bacteria or a mammalian cell. The POI can be a protein or a library of proteins such as antibodies, antibody fragments, single chain antibodies (e.g., scFv, scFab), single domain antibodies, protein scaffolds (e.g., based on fibronectin III, cystatin, lipocalins, Ankyrin repeat domains, Z domain of protein A and others) etc. The system can be used to select for proteins with certain properties such as affinity, activity or certain biological or physical properties. Depending on the biological entity the selection system would be referred to as phage display, yeast display, bacterial display or mammalian display.

In other embodiments the POI library is fused to the capture protein and the anchor protein is fused to the tether sequence.

In yet other embodiments, the system described in the first embodiment uses a SpyTag/SpyCatcher system to spontaneously form a covalent bond and link the POI to the anchor protein. The SpyTag or a modified or optimized version of it, e.g., SpyTag002, is the tether sequence and the SpyCatcher or a modified or optimized version of it, e.g., SpyCatcher002, is the capture sequence. The POI is either fused to the SpyTag and the anchor protein is fused to the SpyCatcher or the POI is fused to the SpyCatcher and the SpyTag is fused to the anchor protein.

In other embodiments, the system described in the first embodiment uses a different protein ligation system than the SpyTag/SpyCatcher to link the POI to the anchor protein such as the SnoopTag/SnoopCatcher (Veggiani et al., 2016), SpyTag/KTag/SpyLigase (Fierer et al., 2014), Sortase system (Schmohl et al., 2014), split inteins (Thiel et al., 2014), Butelase 1 (Nguyen et al., 2014), Peptiligase (Toplak et al., 2016), or other similar methods.

In a yet another embodiment, a POI, such as an antibody fragment or single chain antibody library with a tethering sequence at the C-terminus of the heavy or light chain and one or more additional tags which can be used for antibody purification or detection is expressed. A filamentous phage, such as M13, is the biological entity. Production of phage with the POI displayed on the surface of the phage is achieved by infection of bacteria carrying a phagemid with the POI-tethering sequence fusion gene with a modified helper phage. The modified helper phage produces a capture sequence-pIII fusion instead of wildtype pIII. The modified pIII might contain a protease cleavage site between the capture sequence and pIII, such as TEV, rhinovirus 3C protease or trypsin, for elution of selected phage by protease cleavage. Furthermore, bacteria carrying a plasmid which encodes a capture sequence-pIII fusion protein or modified bacteria which carry a capture sequence-pIII gene in their genome can be used in combination with helper phage infection to produce new POI displaying phage. Instead of a complete pIII fusion, an optimized, modified or truncated pIII fusion might be used.

In another embodiment, a POI, such as an antibody fragment or single chain antibody library with a capture sequence at the C-terminus of the heavy or light chain and one or more additional tags which can be used for antibody purification or detection is expressed. A filamentous phage, such as M13, is the biological entity. Production of phage with the POI displayed on the surface of the phage is achieved by infection of bacteria carrying a phagemid with the POI-capture sequence fusion gene with a modified helper phage. The modified helper phage produces a tethering sequence-pIII fusion instead of wildtype pIII. The modified pIII might contain a protease cleavage site between the tethering sequence and pIII, such as TEV, rhinovirus 3C protease or trypsin, for elution of selected phage by protease cleavage. Furthermore, bacteria carrying a plasmid which encodes a tethering sequence-pIII fusion protein or modified bacteria which carry a tethering sequence-pIII gene in their genome can be used in combination with helper phage infection to produce new POI displaying phage. Instead of a complete pIII fusion, an optimized, modified or truncated pIII fusion might be used.

As used in this specification and claims, the singular form "a," "an," and "the" include plural references unless the context clearly dictates otherwise.

As used herein the term "genetic constructs" refers to polynucleotide sequences encoding a protein of interest (POI) that is fused, in frame, to a "tether sequence" (TS) or to a capture sequence (CS) or to a protein (also referred to as an "anchor protein") expressed on the surface or linked to the surface of a prokaryotic cell, eukaryotic cell, prokaryotic virus or phage, or eukaryotic virus that is fused, in frame, to a capture sequence or tether sequence. For ease of reference, GC1 refers to genetic constructs comprising POI fused to a tether sequence or capture sequence and GC2 refers to genetic constructs comprising a capture sequence or tether sequence fused to an anchor protein.

The terms "tether sequence" or "tethering sequence" relate to a sequence that is attached to a POI or anchor protein and that facilitates the formation of a covalent linkage to a capture moiety expressed either on the surface of a biological entity or fused to the POI. Non-limiting examples of tethering sequences include SpyTag sequences, including SpyTag002, SnoopTag sequences, Sortase motifs, a C-peptide, butelase substrates, and peptiligase substrates. The tether sequence may be fused to POI or anchor protein at the N- or C-terminus of such proteins or polypeptides or in an internal loop. Particularly, a spacer sequence (e.g., a glycine/serine rich spacer) may flank the tether sequence in order to enhance accessibility for reaction. The spacer may further include a site for specific proteolysis (e.g., by Factor X, thrombin, enterokinase, tobacco etch virus (TEV) NIa protease, rhinovirus 3C protease or trypsin), allowing specific release from a tether sequence.

The term "capture sequence" refers to a polypeptide fused to an anchor protein or POI with which a tethering sequence forms a covalent peptide linkage, for example SpyCatcher for the SpyTag tethering sequence. The capture sequence may be fused to the anchor protein or POI at the N- or C-terminus of such proteins or polypeptides or in an internal loop. Particularly, a spacer sequence (e.g., a glycine/serine rich spacer) may flank the capture sequence in order to enhance accessibility for reaction. The spacer may further include a site for specific proteolysis (e.g., by Factor X, thrombin, enterokinase, tobacco etch virus NIa protease, rhinovirus 3C protease or trypsin), allowing specific release from a capture sequence.

The term "prokaryotic system" refers to prokaryotic cells such as bacterial cells or prokaryotic viruses, prokaryotic phages or bacterial spores. The term "eukaryotic system" refers to eukaryotic cells including cells of animal, plants, fungi and protists, and eukaryotic viruses such as retrovirus, adenovirus, baculovirus. Prokaryotic and eukaryotic systems may be, collectively, referred to as "expression systems".

The term "expression cassette" is used here to refer to a functional unit that is built in a vector for the purpose of expressing recombinant proteins/peptides. An expression cassette includes a promoter or promoters, a transcription terminator sequence, a ribosome binding site or ribosome binding sites, and the cDNA encoding a tether sequence or a capture sequence. Other genetic components can be added to an expression cassette, depending on the expression system (e.g., enhancers and polyadenylation signals for eukaryotic expression systems).

As used herein the term "vector" refers to a nucleic acid molecule, preferably self-replicating, which transfers an inserted nucleic acid molecule into and/or between host cells. Typically vectors are circular DNA comprising a replication origin, a selection marker, and/or viral package signal, and other regulatory elements. Vector, vector DNA, plasmid DNA, phagmid DNA are interchangeable terms in description of this invention. The term includes vectors that function primarily for insertion of DNA or RNA into a cell, replication vectors that function primarily for the replication of DNA or RNA, and expression vectors that function for transcription and/or translation of the DNA or RNA. Also included are vectors that provide more than one of the above functions.

As used herein the term "expression vector" is a polynucleotide which, when introduced into an appropriate host cell, can be transcribed and translated into a polypeptide(s). The term "expression vector," refers to vectors that direct the soluble expression of proteins of interest fused in frame with a tether sequence which is characterized by an ability to form a peptide linkage to capture sequence with a capture sequence produced by a helper vector as disclosed herein. The POI may also be fused in frame with a capture sequence which is characterized by an ability to form a peptide linkage to tether sequence with a tether sequence produced by a helper vector as disclosed herein.

The term "helper vector" refers to a genetic system, or host cell-specific vector designed to produce fusion proteins comprising an anchor protein fused in frame with a capture sequence. The anchor protein may also be fused in frame with a tether sequence. Helper vectors can be introduced into expression systems, in combination with an expression vector, transiently by co-transformation, permanently by integration into host genome, or by viral or phage infection of the host cells.

As used herein the term "display vector set" refers to particular combinations of expression vectors (which provide GC1 constructs) and helper vectors (which provide GC2 constructs). The co-expression of the GC1 and GC2 result in the display of POI on the surface of an expression system.

The term "anchor protein" as used herein, refers to a polypeptide or protein of which a portion is found outside the cell membrane or the outer surface of an expression system. Capture sequences or tether sequences are fused to the portion of the anchor protein, (usually the N-terminal portion of the anchor protein) that is found on the outer surface of a cell (see, for example, FIG. 1). Non-limiting examples of anchor proteins are provided in Table 1 or have been disclosed in other publications, such as Little et al., which is hereby incorporated by reference in its entirety.

Where phage display systems, such as bacteriophage M13 virus particles are used as an expression system, captures sequences or tether sequences can be fused, in frame, to coat proteins, such as within genes III, VI, VII, VIII and IX, modified or truncated coat proteins such as long, short or supershort versions of pIII. Alternatively, capture sequences or tether sequences can be expressed on the surface of bacterial cells, such as *E. coli*. For example, capture sequences can be fused to anchor proteins such as outer membrane proteins (Chang and Lo, 2000; Lee et al., 2004, pili and flagella (Westerlund-Wikstrom et al., 1997), modified lipoproteins (Georgiou et al., 1996), ice nucleation proteins (Jung et al., 1998), or autotransporters (Veiga et al., 2003).

Capture sequences can also be displayed on the surfaces of eukaryotic host cells, such as *Saccharomyces cerevisiae*. For example, the cell wall protein alpha-agglutinin 1 and alpha-agglutinin 2, Cwp1, Cwp2, Gas1p, Yap3p, Flo1p, Crh2p, Pir1, Pir2, Pir4, and Icwp in *S. cerevisiae*; HpSEDI, HpGASI, HpTIPI, HPWPI in *Hansenula polymorpha*, and Hwp1p, Als3p, Rbt5p in *Candida albicans* can be used to display capture sequences on yeast cell surfaces.

Likewise, mammalian cells can be manipulated to express capture sequences on the cell surface. For example, a capture sequence can be expressed on membrane anchor proteins, such as cell surface receptors (Chesnut et al., 1996, J Immunological Methods; Ho et al, 2006, PNAS, 103:9637-9642), GPI anchor sequences (U.S. Pat. No. 6,838,446), non-cleavable type 11 signal anchor sequences (U.S. Pat. No. 7,125,973).

TABLE 1

Examples for different surface display systems

| Display System | Anchor | Anchor | References |
| --- | --- | --- | --- |
| Phage | pIII | M13 Coat Protein | McCafferty et al. (1990) |
| | | | Bastien et al. (1997) |
| | pVIII | M13 Coat Protein | Benhar (2001) |
| | pVII and PIX | | Gao et al. (1999) |
| | | | Tornetta et al. (2012) |
| Virus-like particles | VP1 | Polyoma virus coat | Gleiter and Lilie (2001) |
| | L1 | Human papilloma virus | Koutsky et al. (2002) |
| Gram-negative cells | LamB | Maltoporin | Benhar (2001) |
| | OmpA | Outer membrane protein | Benhar (2001) |
| | Lpp-OmpA | Lipoprotein/OmpA chimere | Chen and Georgiou (2002) |
| | INP | Ice nucleation protein | Li et al. (2003) |
| | FliC | Flagellae protein (flagellin) | Lu et al. (1995) |
| | FimA | Fimbriae protein (fimbrillin) | Samuelson et al. (2002) |
| Gram-positive Cells | Protein A | Cell wall anchor (covalent) | Steidler et al. (1998) |
| | LysM | Cell wall anchor (non-covalent) | Shao et al. (2009) |
| | FnBPB | Fibronectin-binding protein | Strauss and Götz (1996) |
| | M6 | Cell wall binding | Wieczorek and Martin (2010) |
| S-layers | SbpA | *Lysinibacillus sphaericus* | Ilk et al. (2011) |
| | RsaA | *Caulobacter crescentus* | Nomellini et al. (2007) |
| Yeast | Agα1 | α-agglutinin | Shimojo et al. (2004) |
| | Aga1/Aga2 | a-agglutinin | Borodina et al. (2010) |
| | | | Wen et al. (2010) |
| | Flo1 | Flocculin | Matsumoto et al. (2002) |
| Endospores | CotB, C, D | Coat proteins | Isticato et al. (2001) |
| | | | Mauriello et al. (2004) |
| | | | Due et al. (2007) |

As used herein the terms "polynucleotides", "nucleic acids", "nucleotides" and "oligonucleotides" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the nucleotide polymer.

As used herein the term "amino acid" refers to either natural and/or unnatural or synthetic amino acids, including glycine and both the D or L optical isomers, and amino acid analogs and peptidomimetics.

As used herein the terms "polypeptide", "peptide", and "protein," are used interchangeably herein to refer to polymers of amino acids of any length. POI may, thus, be a polypeptide, peptide or protein.

A "protein of interest" (POI) is any desired polypeptide, peptide, or protein. Non-limiting examples of POI include antibodies, for example full length antibodies, antibody fragments, single chain antibodies (e.g., scFv, scFab), or single domain antibodies, protein scaffolds (e.g. based on fibronectin III, cystatin, lipocalins, Ankyrin repeat domains, Z domain of protein A and others), hormones, interleukins, antigens for the development of vaccines, enzymes, etc. Other examples include, and are not limited to: human growth hormone (hGH), N-methionyl human growth hormone, bovine growth hormone, parathyroid hormone, thyroxine, insulin A-chain, insulin B-chain, proinsulin, relaxin A-chain, relaxin B-chain, prorelaxin, glycoprotein hormones such as follicle stimulating hormones (FSH), thyroid stimulating hormone (TSH), and leutinizing hormone (LH), glycoprotein hormone receptors, calcitonin, glucagon, factor VIII, an antibody, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, a microbial protein, such as betalactamase, tissue factor protein, inhibin, activin, vascular endothelial growth factor, receptors for hormones or growth factors; integrin, thrombopoietin, protein A or D, rheumatoid factors, nerve growth factors such as NGF-β, platelet-growth factor, transforming growth factors (TGF) such as TGF-alpha and TGF-beta, insulin-like growth factor-I and —II, insulin-like growth factor binding proteins, CD-4, DNase, latency associated peptide, erythropoietin, osteoinductive factors, interferons such as interferon-alpha, -beta, and -gamma, colony stimulating factors (CSFs) such as M-CSF, GF-CSF, and G-CSF, interleukins (ILs) such as IL-1, IL-2, IL-3, IL-4, superoxide dismutase; decay accelerating factor, viral antigen, HIV envelope proteins such as GP120, GP140, atrial natriuretic peptides A, B or C, immunoglobulins, and fragments of any of the above-listed proteins.

As used herein the term "host cell" includes an individual cell or cell culture which can be, or has been, a recipient for the disclosed vectors. Host cells include progeny of a single host cell. The progeny may not necessarily be completely identical to the original parent cell due to natural, accidental, or deliberate mutation.

As used herein, a polypeptide or polynucleotide sequence is "essentially identical" or "substantially similar" to comparison sequence, if both sequences exhibit substantial amino acid or nucleotide sequence homology. Generally, essentially identical or substantially identical sequences are at least about 60% identical with each other, after alignment to the homologous regions. Preferably, the sequences are at least about 70% identical, more preferably, they are at least about 80% identical, more preferably, they are at least about 90% identical, of more preferably, the sequences are at least about 95% identical.

Tether and Capture Sequences

Tether and capture sequences are protein or peptide sequences which can form a covalent bond to each other spontaneously or enzymatically with or without addition or involvement of other factors (proteins, enzymes, catalysts, salts etc.). A few non-limiting examples are listed below.

SpyTag/SpyCatcher

U.S. Pat. No. 9,547,003 (the disclosure of which is hereby incorporated by reference in its entirety) discloses the components of the SpyTag/SpyCatcher system (used as a tether). As discussed therein, in this respect, the tether sequence about 5-50 amino acids in length (e.g., about 10, 20, 30, 40 or 50 amino acids in length) and is derived from SEQ ID NOs: 1, 3, 5 or 6. Capture sequences are also derived from SEQ ID NOs: 1, 3, 5 or 6 and can be of any length.

The tether sequence and capture sequence may be fused to POI at the N- or C-terminus of such proteins or polypeptides or in an internal loop. Particularly, a spacer sequence (e.g., a glycine/serine rich spacer) may flank the tether sequence or the capture sequence in order to enhance accessibility for reaction. The spacer may further include a site for specific proteolysis (e.g., by Factor X, thrombin, enterokinase or tobacco etch virus NIa protease), allowing specific release from a tether or capture sequence. Thus, the tether sequence comprises residues 302-308 of the sequence set out in SEQ ID NO: 1, SEQ ID NO: 25 (mgsshhhhhh ssglvprgsv ptivmvdayk rykgsgesgk), SEQ ID NO: 27 (VPTIVMVDAYKRYKS), or a sequence with at least 50% identity to SEQ ID NO: 1, 25 or 27, wherein said peptide tag is less than 50 amino acids in length. In certain embodiments, the tether sequence has at least about 55%, about 60%, about 65%, about 70%, about 75%, about 80%, about 85%, about 90%, or about 95% identity to SEQ ID NO: 1 and is less than 50 amino acids in length. More particularly, the tether sequence may comprise residues 301-308, 300-308, 299-308, 298-308, 297-308, 296-308, 295-308, 294-308, 293-308, 292-308, 291-308 or 290-308 of SEQ ID NO: 1 or a sequence with at least about 50% to 95% identity to residues 302-308 of SEQ ID NO: 1 or 25. Preferably the tether sequence comprises the reactive asparagine of position 303 in SEQ ID NO: 1, i.e., this residue is preferably unchanged. Further, the tether sequence may be a fragment of SEQ ID NO: 1 or 25 and, in a preferred embodiment, a tether sequence of less than 50 amino acids and which comprises residues 293-308 of the sequence set forth in SEQ ID NO: 1 or which comprises a sequence with at least 50% identity thereto is used. The peptide tags are length restricted and comprise less than 50 amino acid residues. Thus the peptide tags do not comprise the sequence of SEQ ID NO: 1 but only specific fragments thereof, or sequences with at least 50% identity e.g., 75, 80, 85, 90 or 95% identity to such specific fragments. Other embodiments utilize SEQ ID NO: 25 or a sequence having at least 50% sequence identity thereto as a tether sequence.

The capture sequence comprises or consists of residues 31-291 of the sequence set out in SEQ ID NO: 1, SEQ ID NO: 26 (msyyhhhhhh dydipttenl yfqgamyttl sglsgeqgps gdmtteedsa thikfskrde dgrelagatm elrdssgkti stwisdghvk dfylypgkyt fvetaapdgy evataitftv neqgqvtvng eatkgdaht), SEQ ID NO: 28 (yfqgamyttl sglsgeqgps gdmtteedsa thikfskrde dgrelagatm elrdssgkti stwisdghvk dfylypgkyt fvetaapdgy evataitftv neqgqvtvng eatkgdaht) or a sequence with at least 50% identity thereto e.g., with 75, 80, 85, 90, 95, 96, 97, 98 or 99% identity to residues 32-291 of SEQ ID NO: 1 or SEQ ID NO: 26 or SEQ ID NO: 28 (yfqgamyttl sglsgeqgps gdmtteedsa thikfskrde dgrelagatm elrdssgkti stwisdghvk dfylypgkyt fvetaapdgy evataitftv neqgqvtvng eatkgdaht). Specifically excluded is the complete sequence set out in SEQ ID NO: 1, however, the capture sequence should contain the reactive lysine corresponding to position 179 of SEQ ID NO: 1. Particularly, the binding partner comprises residues 31-292, 31-293, 31-294, 31-295, 31-296, 31-297, 31-298, 31-299, 31-300, 31-301 or 31-302 of the sequence set forth in SEQ ID NO: 1 or a sequence with at least 70% identity thereto, excluding the sequence of SEQ ID NO: 1.

Additionally, a tether sequence may be designed from the major pilin protein Spy0128 using the alternative isopeptide bond in the N-terminus. Therefore, tether sequence may be designed or is obtainable from an N-terminal fragment of the isopeptide protein and the remaining, truncated or overlapping protein fragment may constitute the capture sequence. The reactive lysine involved in the isopeptide bond at the N-terminus is found at position 36 of SEQ ID NO: 1 and the reactive asparagine involved in the isopeptide bond is found at position 168 of SEQ ID NO: 1. Thus, in a preferred embodiment the tether sequence comprises the reactive lysine residue in this instance and the capture sequence comprises the reactive asparagine. Particularly, a tether sequence comprises residues 31-40 of the sequence set out in SEQ ID NO: 1 or a sequence with at least 70% identity thereto and is less than 50 amino acids in length. The corresponding capture sequence for the above described tether sequence comprises residues 37-304 of the sequence set out in SEQ ID NO: 1 or has a sequence with at least 70% identity thereto, excluding the sequence of SEQ ID NO: 1. Preferably, the reactive residues in the peptide tag and binding partner are not mutated.

Another tether sequence comprises residues 179-184 e.g., 173-185 of the sequence set out in SEQ ID NO: 3 or has a sequence with at least 50% identity thereto and is less than 50 amino acids in length. The capture sequence comprises residues 191-317 e.g., 186-318 of SEQ ID NO: 3 or a sequence having at least 50% identity thereto, excluding SEQ ID NO: 3. Specifically excluded as a tether sequence or a capture sequence is the full length sequence of SEQ ID NO: 3.

Another tether sequence comprises fragments of SEQ ID NO: 5 that include the asparagine at position 266 (or sequences having at least 50% identity thereto) and a capture sequence comprising fragments of SEQ ID NO: 5 that have at least 50% sequence identity thereto and which comprises the lysine residue at position 149 but which does not include the asparagine at position 266. Neither the tether sequence nor the capture sequence comprise SEQ ID NO: 5.

In another embodiment, the tether sequence comprises a fragment of SEQ ID NO: 6 that includes the aspartic acid residue at position 101 (or a sequence at least 70% identical thereto) and the capture sequence comprises fragments of SEQ ID NO: 6 that contain the reactive lysine of position 15 (or sequences at least 50% identical thereto). Neither the tether sequence nor the capture sequence comprise SEQ ID NO: 6.

Another embodiment provides for a tether sequence comprising SEQ ID NO: 25 (mgsshhhhhh ssglvprgsv ptivmvdayk rykgsgesgk), SEQ ID NO: 27 (VPTIVMVDAYKRYKS), or a sequence with at least 50% identity to SEQ ID NO: 25 or 27, wherein said peptide tag is 15 to 40 or 50 amino acids in length. In certain embodiments, the tether sequence has at least about 55%, about 60%, about 65%, about 70%, about 75%, about 80%, about 85%, about 90%, or about 95% identity to SEQ ID NO: 25 or 27 and is less than 50 amino acids in length. Preferably the tether sequence comprises the reactive aspartic acid of position 8 in SEQ ID NO: 27, i.e., this residue is preferably unchanged.

A capture sequence for either of SEQ ID NO: 25, 27 or a sequence with at least 50% identity to SEQ ID NO: 25 or 27, that is 15 to 40 or 50 amino acids in length and contains an aspartic acid of position 8 in SEQ ID NO: 27, comprises or consists of SEQ ID NO: 26 (msyyhhhhhh dydipttenl yfqgamvttl sglsgeqgps gdmtteedsa thikfskrde dgrelagatm elrdssgkti stwisdghvk dfylypgkyt fvetaapdgy evataitftv neqgqvtvng eatkgdaht) or yfqgamvttl sglsgeqgps gdmtteedsa thikfskrde dgrelagatm elrdssgkti stwisdghvk dfylypgkyt fvetaapdgy evataitftv neqgqvtvng eatkgdaht, or a sequence with at least 50% identity thereto e.g., with 75, 80, 85, 90, 95, 96, 97, 98 or 99% identity to SEQ ID NO: 26 or SEQ ID NO: 28 (yfqgamvttl sglsgeqgps gdmtteedsa thikfskrde dgrelagatm elrdssgkti stwisdghvk dfylypgkyt fvetaapdgy evataitftv neqgqvtvng eatkgdaht). Variants have at least 50% sequence identity and retain the lysine at position 57 of SEQ ID NO: 26.

SpyLigase/SnoopLigase

Alternatively, POI can be attached to exposed surface proteins using the systems described in WO2016/193746 (which is hereby incorporated by reference in its entirety). In such embodiments, tether sequences are attached to both the POI and an anchor protein, optionally through linker sequences, such as a glycine/serine rich spacer. These tether sequences are then ligated by a ligase that is also encoded by the host cell. The tether sequence can, in some embodiments, have a length between 6-50 amino acids, e.g., 7-45, 8-40, 9-35, 10-30, 11-25 amino acids in length, e.g. it may comprise or consist of 6, 7, 8, 9, 10, 11, 12, 13, 14, 15, 16, 17, 18, 19 or 20 amino acids. Other embodiments provide a tether sequence of about 20-300 amino acids in length (e.g., about 10, 20, 30, 40, 50, 60, 70, etc. amino acids length). In some embodiments, the peptide ligase may be between 50-300 amino acids in length, e.g., 60-250, 70-225, 80-200 amino acids in length, e.g., it may comprise or consist of 60, 65, 70, 75, 80, 85, 90, 95, 100, 110, 120, 130, 140, 150, 160, 170, 180, 190 or 200 amino acids, providing it meets the definitions set forth for the ligase, below. Tether sequences attached to an anchor protein correspond to a capture sequence in this aspect of the invention.

A pair of tether sequences may be derived from any suitable isopeptide protein. For instance, tether sequences may be derived from the major pilin protein Spy0128, which has an amino acid sequence as set out in SEQ ID NO: 7 and is encoded by a nucleotide sequence as set out in SEQ ID NO: 8. Two isopeptide bonds are formed in the protein. One isopeptide bond is formed between lysine at position 179 in SEQ ID NO: 7 and asparagine at position 303 in SEQ ID NO: 7 (the reactive residues). The glutamic acid residue which induces the spontaneous isopeptide bond is found at position 258 in SEQ ID NO: 7. Thus, a pair of tether sequences developed from an isopeptide protein set forth in SEQ ID NO: 7 will preferably comprise a tether sequence comprising a fragment of the protein comprising the reactive asparagine at position 303 and a tether sequence comprising a fragment of the protein comprising the reactive lysine at position 179. A fragment of the protein comprising the glutamic acid residue at position 258 can be provided separately, i.e., as a peptide ligase that forms the isopeptide bond.

Another isopeptide bond in the major pilin protein Spy0128 occurs between the lysine residue at position 36 of SEQ ID NO: 7 and the asparagine residue at position 168 of SEQ ID NO: 7. The glutamic acid residue which induces isopeptide formation is found at position 117 in SEQ ID NO: 7. Thus, a pair of tether sequences developed from an isopeptide protein set forth in SEQ ID NO: 7 will preferably comprise a tether sequence comprising a fragment of the protein comprising the reactive lysine residue at position 36 and a tether sequence comprising a fragment of the protein comprising the reactive asparagine at position 168. A fragment of the protein comprising the glutamic acid residue at position 117 may be provided separately as a peptide ligase.

An isopeptide bond occurs between a lysine residue at position 181 of SEQ ID NO: 9 (ACE19, a domain of an adhesin protein from E. faecalis) and an asparagine residue at position 294 of SEQ ID NO: 9. The bond is induced by an aspartic acid residue at position 213 in SEQ ID NO: 9. Thus, a pair of tether sequences developed from isopeptide protein set forth in SEQ ID NO: 9 will preferably comprise a tether sequence comprising a fragment of the protein comprising the reactive asparagine residue at position 294 and a tether sequence comprising a fragment of the protein comprising the reactive lysine residue at position 181. A fragment of the protein comprising the aspartic acid residue at position 213 may be provided separately as a peptide ligase.

The collagen binding domain from S. aureus which has an amino acid sequence set out in SEQ ID NO: 10 can also be used. The isopeptide bond occurs between lysine at position 176 of SEQ ID NO: 10 and asparagine at position 308 of SEQ ID NO: 10. The aspartic acid residue which induces the isopeptide bond is at position 209 of SEQ ID NO: 10. Thus, a pair of tether sequences developed from the isopeptide protein set forth in SEQ ID NO: 10 will preferably comprise a tether sequence comprising a fragment of the protein comprising the reactive lysine at position 176 and a tether sequence comprising a fragment of the protein comprising the reactive asparagine at position 308. A fragment of the protein comprising the aspartic acid residue at position 209 may be provided separately as a peptide ligase.

FbaB from Streptococcus pyogenes can also be used to provide tether sequences and comprises a domain, CnaB2, which has an amino acid sequence set out in SEQ ID NO: 11, is encoded by the nucleotide sequence set out in SEQ ID NO: 12. The isopeptide bond in the CnaB2 domain forms between a lysine at position 15 of SEQ ID NO: 11 and an aspartic acid residue at position 101 of SEQ ID NO: 11. The glutamic acid residue which induces the isopeptide bond is at position 61 of SEQ ID NO: 11. Thus, a pair of tether sequences developed from the isopeptide protein set forth in SEQ ID NO: 11 will preferably comprise a tether sequence comprising a fragment of the protein comprising the reactive lysine at position 15 and a tether sequence comprising a fragment of the protein comprising the reactive aspartic acid at position 101. A fragment of the protein comprising the glutamic acid residue at position 61 may be provided separately as a peptide ligase.

The RrgA protein is an adhesion protein from Streptococcus pneumoniae, which has an amino acid sequence as set out in SEQ ID NO: 13 and is encoded by a nucleotide sequence as set out in SEQ ID NO: 14. An isopeptide bond is formed between lysine at position 742 in SEQ ID NO: 13 and asparagine at position 854 in SEQ ID NO: 13. The bond is induced by a glutamic acid residue at position 803 in SEQ ID NO: 13. Thus, a pair of tether sequences developed from the isopeptide protein set forth in SEQ ID NO: 13 will preferably comprise a tether sequence comprising a fragment of the protein comprising the reactive asparagine at position 854 and a tether sequence comprising a fragment of the protein comprising the reactive lysine at position 742. A fragment of the protein comprising the glutamic acid residue at position 803 may be provided separately as a peptide ligase as defined above.

The PsCs protein is a fragment of the por secretion system C-terminal sorting domain protein from Streptococcus intermedius, which has an amino acid sequence as set out in SEQ ID NO: 15 and is encoded by a nucleotide sequence as set out in SEQ ID NO: 16. An isopeptide bond is formed between lysine at position 405 in SEQ ID NO: 15 and aspartate at position 496 in SEQ ID NO: 15. Thus, a pair of tether sequences developed from the isopeptide protein set forth in SEQ ID NO: 15 will preferably comprise a tether sequence comprising a fragment of the protein comprising the reactive aspartate at position 496 and a tether sequence comprising a fragment of the protein comprising the reactive lysine at position 405.

In various embodiments, tether sequences may be derived from an isopeptide protein comprising an amino acid sequence as set forth in any one of SEQ ID NO: 21, 23, 25 or 27 or a protein with at least 70% sequence identity to an amino acid sequence as set forth in any one of SEQ ID NO: 21, 23, 25 or 27. In some embodiments, said isopeptide protein sequence above is at least 75, 80, 85, 90, 95, 96, 97, 98, 99 or 100% identical to the sequence (SEQ ID NO: 21, 23, 25 or 27) to which it is compared.

Sortase

Another means for tethering POI to anchor proteins comprises the use of sortase enzymes and sortase recognition and bridging domains. Schmohl et al. (2014), which is hereby incorporated by reference in its entirety, discuss sortase mediated ligation for the site-specific modification of proteins. In this aspect of the invention, the sortase recognition and bridging domains are considered tethering sequences and the tethering sequence fused to an anchor protein corresponds to a capture sequence in this aspect of the invention. Sortases are transpeptidases produced by Gram-positive bacteria to anchor cell surface proteins covalently to the cell wall. The Staphylococcus aureus sortase A (SrtA) cleaves a short C-terminal recognition motif (LPXTG (SEQ ID NO: 17) (referred to herein as a sortase recognition domain). The sortase recognition domain is a sortase A recognition domain or a sortase B recognition domain. In particular embodiments, the sortase recognition domain comprises or consists of the amino acid sequence: LPTGAA (SEQ ID NO: 18), LPTGGG (SEQ ID NO: 19), LPKTGG (SEQ ID NO: 20), LPETG (SEQ ID NO: 21), LPXTG (SEQ ID NO: 22) or LPXTG(X)$_n$ (SEQ ID NO: 23), where X is any amino acid, and n is 0, 1, 2, 3, 4, 5, 7, 8, 9, 10, in the range of 0-5 or 0-10, or any integer up to 100. The sortase recognition domain can be fused, in frame, to a POI or an anchor protein, optionally through a glycine/serine rich spacer. Where it is attached to a POI, it is considered a tether sequence and where it is attached to an anchor protein, it is considered a capture sequence.

The sortase A bridging domain comprises one or more glycine residues at one of its termini. In certain embodiments, the one or more glycine residues may optionally be: Gly, (Gly)$_2$, (Gly)$_3$, (Gly)$_4$, or (Gly)$_x$, where x is an integer of 1-20. The sortase bridging domain can be attached to a POI or an anchor protein, optionally through a glycine/serine rich spacer. Where it is attached to a POI, it is considered a tether sequence and where it is attached to an anchor protein, it is considered a capture sequence.

The sortase B recognition domain comprises the amino acid sequence NPX1TX2 (SEQ ID NO: 31), where X1 is glutamine or lysine; X2 is asparagine or glycine; N is asparagine; P is proline and T is threonine. The sortase B. The sortase recognition domain can be fused, in frame, to a POI or an anchor protein, optionally through a glycine/serine rich spacer. Where it is attached to a POI, it is considered a tether sequence and where it is attached to an anchor protein, it is considered a capture sequence.

The sortase B bridging domain comprises one or more glycine residues at one of its termini. In certain embodiments, the one or more glycine residues may optionally be: Gly, (Gly)$_2$, (Gly)$_3$, (Gly)$_4$ (SEQ ID NO: 32), or (Gly)$_x$, where x is an integer of 1-20. The sortase bridging domain can be attached to a POI or an anchor protein, optionally through a glycine/serine rich spacer. Where it is attached to a POI, it is considered a tether sequence and where it is attached to an anchor protein, it is considered a capture sequence.

Butelase 1

Yet another means for tethering a POI to an anchor protein comprises the use of butelase 1 to form a peptide bond between the butelase recognition motif (where Asx is Asn or Asp) and the amino terminus of another polypeptide. In this case, the Asx-His-Val motif can be fused, in frame, to a POI or an anchor protein, optionally through a glycine/serine rich spacer. Butelase can then be used to form a peptide bond between the Asx-His-Val motif and the N-terminal amino acid of the anchor protein. WO 2017/058114, which is hereby incorporated by reference in its entirety, discloses methods and materials for butelase-mediated peptide ligation.

Split Inteins

Another method for tethering a POI to an anchor protein comprises the use of split inteins. Inteins can exist as two fragments encoded by two separately transcribed and translated genes. These so-called split inteins self-associate and catalyze protein-splicing activity in trans. Split inteins have been identified in diverse cyanobacteria and archaea (Caspi et al., 2003; Choi J. et al., 2006; Dassa B. et al., 2007; Liu X. and Yang J., 2003; Wu H. et al., 1998; and Zettler J. et al., 2009, the disclosures of which are hereby incorporated by reference in their entireties). Thiel et al. (2014) and WO 2013/045632, each of which is hereby also incorporated by reference in its entirety, also disclose the use of split inteins that can be used to fuse heterologous proteins.

Vectors

The vectors of the present invention generally comprise transcriptional or translational control sequences required for expressing the POI and anchor proteins. Suitable transcription or translational control sequences include but are not limited to replication origin, promoter, enhancer, repressor binding regions, transcription initiation sites, ribosome binding sites, translation initiation sites, and termination sites for transcription and translation.

The origin of replication (generally referred to as an ori sequence) permits replication of the vector in a suitable host cell. The choice of ori will depend on the type of host cells and/or genetic packages that are employed. Where the host cells are prokaryotes, the expression vector typically comprises two ori sequences, one directing autonomous replication of the vector within the prokaryotic cells, and the other ori supports packaging of the phage particles. Preferred prokaryotic ori is capable of directing vector replication in bacterial cells. Non-limiting examples of this class of ori include pMB1, pUC, as well as other *E. coli* origins. Preferred ori supporting packaging of the phage particles includes but is not limited to f1 ori, Pf3 phage replication ori.

In the eukaryotic system, higher eukaryotes contain multiple origins of DNA replication, but the ori sequences are not clearly defined. The suitable origins of replication for mammalian vectors are normally from eukaryotic viruses. Preferred eukaryotic ori include, but are not limited to, SV40 ori, EBV ori, or HSV ori.

As used herein, a "promoter" is a DNA region capable under certain conditions of binding RNA polymerase and initiating transcription of a coding region located downstream (in the 3' direction) from the promoter. It can be constitutive or inducible. In general, the promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains responsible for the binding of RNA polymerase. Eukaryotic promoters will often, but not always, contain "TATA" boxes and "CAT" boxes.

The choice of promoters will largely depend on the host cells in which the vector is introduced. For prokaryotic cells, a variety of robust promoters are known in the art. Preferred promoters are lac promoter, Trc promoter, T7 promoter and pBAD promoter. Normally, to obtain expression of exogenous sequence in multiple species, the prokaryotic promoter can be placed immediately after the eukaryotic promoter, or inside an intron sequence downstream of the eukaryotic promoter.

Suitable promoter sequences for eukaryotic cells include the promoters for 3-phosphoglycerate kinase, or other glycolytic enzymes, such as enolase, glyceraldehyde-3phosphate dehydrogenase, hexokinase, pyruvate decarboxylase, phosphofructokinase, glucose-6phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Preferred promoters for mammalian cells are SV40 promoter, CMV promoter, β-actin promoter and their hybrids. Preferred promoters for yeast cell includes but is not limited to GAL 10, GAL I, TEFI in *S. cerevisiae*, and GAP, AOX1 in *P. pastoris*.

In constructing the subject vectors, the termination sequences associated with the exogenous sequence are also inserted into the 3' end of the sequence desired to be transcribed to provide polyadenylation of the mRNA and/or transcriptional termination signal. The terminator sequence preferably contains one or more transcriptional termination sequences (such as polyadenylation sequences) and may also be lengthened by the inclusion of additional DNA sequence so as to further disrupt transcriptional readthrough. Preferred terminator sequences (or termination sites) of the present invention have a gene that is followed by a transcription termination sequence, either its own termination sequence or a heterologous termination sequence. Examples of such termination sequences include stop codons coupled to various yeast transcriptional termination sequences or mammalian polyadenylation sequences that are known in the art and are widely available. Where the terminator comprises a gene, it can be advantageous to use a gene which encodes a detectable or selectable marker; thereby providing a means by which the presence and/or absence of the terminator sequence (and therefore the corresponding inactivation and/or activation of the transcription unit) can be detected and/or selected.

In addition to the above-described elements, the vectors may contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins, e.g., ampicillin, kanamycin, neomycin, zeocin, G418, methotrexate, etc.; (b) complement auxotrophic deficiencies; or (c) supply critical nutrients not available from complex media. The choice of the proper marker gene will depend on the host cell, and appropriate genes for different hosts are known in the art.

In one embodiment, the expression vector is a shuttle vector, capable of replicating in at least two unrelated host systems. In order to facilitate such replication, the vector generally contains at least two origins of replication, one effective in each host system. Typically, shuttle vectors are capable of replicating in a eukaryotic host system and a prokaryotic host system. This enables detection of protein expression in the eukaryotic host (the expression cell type) and amplification of the vector in the prokaryotic host (the amplification cell type). Preferably, one origin of replication is derived from SV40 or 2u and one is derived from pUC, although any suitable origin known in the art may be used provided it directs replication of the vector. Where the vector is a shuttle vector, the vector preferably contains at least two selectable markers, one for the expression cell type and one for the amplification cell type. Any selectable marker known in the art or those described herein may be used provided it functions in the expression system being utilized.

The vectors encompassed by the invention can be obtained using recombinant cloning methods and/or by chemical synthesis. A vast number of recombinant cloning techniques such as PCR, restriction endonuclease digestion and ligation are well known in the art, and need not be described in detail herein. One of skill in the art can also use the sequence data provided herein or that in the public or proprietary databases to obtain a desired vector by any synthetic means available in the art. Additionally, using well-known restriction and ligation techniques, appropriate sequences can be excised from various DNA sources and integrated in operative relationship with the exogenous sequences to be expressed in accordance with the present invention.

The application also provides the following non-limiting items:

1. A combination of vectors comprising:
   a) a first vector comprising a genetic construct (GC1) comprising polynucleotide encoding a protein of interest (POI) fused, in frame, to a tether sequence; and
   b) a second vector comprising a genetic construct (GC2) comprising polynucleotide encoding an anchor protein fused, in frame, to a capture sequence, the tether sequence and capture sequence forming a covalent bond when brought into contact with one another either spontaneously or with the help of an enzyme or a combination of vectors comprising:
   a) a first vector comprising a genetic construct (GC1) comprising polynucleotide encoding a protein of interest (POI) fused, in frame, to a capture sequence; and
   b) a second vector comprising a genetic construct (GC2) comprising polynucleotide encoding an anchor protein fused, in frame, to a tether sequence, the tether sequence and capture sequence forming a covalent bond when brought into contact with one another either spontaneously or with the help of an enzyme;

2. The combination of vectors according to item 1, wherein each vector comprises transcriptional or translational control sequences for expressing the POI and anchor protein;

3. The combination of vectors according to item 1, wherein said transcription or translational control sequences are selected from replication origins, promoters, enhancers, repressor binding regions, transcription initiation sites, ribosome binding sites, translation initiation sites, and termination sites for transcription and translation;

4. The combination of vectors according to any one of items 1-3, wherein said POI is selected from antibodies, antibody fragments, single chain antibodies, scFv, scFab, single domain antibodies, protein scaffolds (e.g. based on fibronectin III, cystatin, lipocalins, Ankyrin repeat domains, Z domain of protein A and others), enzymes, hormones, interleukins, antigens for the development of vaccines, human growth hormone (hGH), N-methionyl human growth hormone, bovine growth hormone, parathyroid hormone, thyroxine, insulin A-chain, insulin B-chain, proinsulin, relaxin A-chain, relaxin B-chain, prorelaxin, follicle stimulating hormones (FSH), thyroid stimulating hormone (TSH), leutinizing hormone (LH), glycoprotein hormone receptors, calcitonin, glucagon, factor VIII, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, a microbial protein, beta-lactamase, tissue factor protein, inhibin, activin, vascular endothelial growth factor, receptors for hormones or growth factors; integrin, thrombopoietin, protein A or D, rheumatoid factors, nerve growth factors, NGF-β, platelet-growth factor, transforming growth factors (TGF), TGF-alpha, TGF-beta, insulin-like growth factor-I or -II, insulin-like growth factor binding proteins, DNase, latency associated peptide, erythropoietin, osteoinductive factors, interferons, interferon-alpha, interferon-beta, interferon-gamma, colony stimulating factors (CSFs), M-CSF, GF-CSF, and G-CSF, interleukins (ILs), IL-1, IL-2, IL-3, IL-4, superoxide dismutase; decay accelerating factor, viral antigens, HIV envelope proteins, GP120, GP140, and atrial natriuretic peptides A, B or C;

5. The combination of vectors according to any one of items 1-4, wherein said tethering sequence is selected from a SpyTag sequence selected from any one of SEQ ID NOs: 1, 3, 5, 6, 25 or 27 a protein with at least 50% sequence identity to an amino acid sequence as set forth in any one of SEQ ID NOs: 1, 3, 5, 6, 25 or 27, a SnoopTag sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

6. The combination of vectors according to any one of items 1-5, wherein capture sequence is a SpyCatcher sequence selected from any one of SEQ ID NOs: 1, 3, 5, 6, 26 or yfqgamyttlsglsgeqgpsgdmtteedsathikfskrdedgrelagatmelrdssgktistwisdghvkdfylypgkytfvetaapdg yevataitftvneqgqvtvngeatkgdaht (SEQ ID NO: 28) a protein with at least 50% sequence identity to an amino acid sequence as set forth in any one of SEQ ID NOs: 1, 3, 5, 6, 26 or yfqgamyttlsglsgeqgpsgdmtteedsathikfskrdedgrelagatmelrdssgktistwisdghvkdfylypgkytfvetaapdg yevataitftvneqgqvtvngeatkgdaht (SEQ ID NO: 28), a SnoopCatcher sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

7. The combination of vectors according to any one of items 1-6, wherein said anchor protein is selected from pIII, pVI, p VII, pVIII, pIX, outer membrane proteins of bacterial cells, pili, flagella modified bacterial lipoproteins, ice nucleation proteins, autotransporters, LamB, OmpA, Lpp-OmpA, INP, FliC, FimA, Protein A, LysM, FnBPB, M6, SbpA, RsaA, cell wall protein alpha-agglutinin 1, alpha-agglutinin 2, Cwp1, Cwp2, Gas1p, Yap3p, Flo1p, Crh2p, Pir1, Pir2, Pir4, Icwp, HpSEDI, HpGASI, HpTIPI, HPWPI, Hwplp, Als3p, Rbt5p, surface receptors, or GPI anchor sequences;

8. A prokaryotic or eukaryotic host cell comprising a combination of vectors according to any one of items 1-7;

9. The prokaryotic or eukaryotic host cell according to item 8, wherein and said host cell comprises a vector comprising a promoter operably linked to a polynucleotide encoding a ligase derived from SEQ ID NOs: 13, 7, 11, 9, 10 or 15 or a ligase having at least 70% sequence identity to a ligase derived from SEQ ID NOs: 13, 7, 11, 9, 10 or 15; a vector comprising a promoter operably linked to a comprising a polynucleotide encoding a sortase; or a vector comprising a promoter operably linked to a polynucleotide encoding a butelase; or said host cell comprises, incorporated into its genome, a promoter operably linked to: a polynucleotide encoding a ligase derived from SEQ ID NOs: 13, 7, 11, 9, 10 or 15 or a ligase having at least 70% sequence identity to a ligase derived from SEQ ID NOs: 13, 7, 11, 9, 10 or 15; a polynucleotide encoding a sortase; or a polynucleotide encoding a butelase;

10. A method for displaying a (poly)peptide/protein on the surface of a bacteriophage particle comprising: causing or allowing the attachment of a protein of interest (POI) to an anchor protein in the protein coat of said bacteriophage particle, wherein said attachment is caused by the formation of a peptide bond between a tether sequence fused to said POI and a capture sequence fused to said anchor protein;

11. The method according to item 10, wherein said tethering sequence is selected from a SpyTag sequence selected from any one of SEQ ID NOs: 1, 3, 5, 6, 25 or 27 or a protein with at least 50% sequence identity to an amino acid sequence as set forth in any one of SEQ ID NOs: 1, 3, 5, 6, 25 or 27, a SnoopTag sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

12. The method according to item 10, wherein capture sequence is a SpyCatcher sequence selected from any one of SEQ ID NOs: 1, 3, 5, 6, 26 or 28, a protein with at least 70% sequence identity to an amino acid sequence as set forth in any one of SEQ ID NOs: 1, 3, 5, 6, 26 or 28, a SnoopCatcher sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

13. The method according to any one of items 10-12, wherein said anchor protein is selected from pIII, pVI, p VII, pVIII, or pIX;

14. The method according to any one of items 10-13, wherein said POI is selected from antibodies, antibody fragments, single chain antibodies, scFv, scFab, single domain antibodies, protein scaffolds (e.g. based on fibronectin III, cystatin, lipocalins, Ankyrin repeat domains, Z domain of protein A and others), enzymes, hormones, interleukins, antigens for the development of vaccines, human growth hormone hGH), N-methionyl human growth hormone, bovine growth hormone, parathyroid hormone, thyroxine, insulin A-chain, insulin B-chain, proinsulin, relaxin A-chain, relaxin B-chain, prorelaxin, follicle stimulating hormones (FSH), thyroid stimulating hormone (TSH), leutinizing hormone (LH), glycoprotein hormone receptors, calcitonin, glucagon, factor VIII, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, a microbial protein, beta-lactamase, tissue factor protein, inhibin, activin, vascular endothelial growth factor, receptors for hormones or growth factors; integrin, thrombopoietin, protein A or D, rheumatoid factors, nerve growth factors, NGF-β, platelet-growth factor, transforming growth factors (TGF), TGF-alpha, TGF-beta, insulin-like growth factor-I or -II, insulin-like growth factor binding proteins, DNase, latency associated peptide, erythropoietin, osteoinductive factors, interferons, interferon-alpha, interferon-beta, interferon-gamma, colony stimulating factors (CSFs), M-CSF, GF-CSF, and G-CSF, interleukins (ILs), IL-1, IL-2, IL-3, IL-4, superoxide dismutase; decay accelerating factor, viral antigens, HIV envelope proteins, GP120, GP140, and atrial natriuretic peptides A, B or C;

15. The method according to item 14, wherein said POI is an antibody, antibody fragment, single chain antibody, scFv, scFab, or single domain antibody;

16. A method for displaying a (poly)peptide/protein on the surface of a prokaryotic or eukaryotic cell comprising: causing or allowing the attachment of a protein of interest (POI) to an anchor protein expressed on the outer surface of said prokaryotic or eukaryotic cell, wherein said attachment is caused by the formation of a peptide bond between a tether sequence fused to said POI and a capture sequence fused to said anchor protein;

17. The method according to item 16, wherein said tethering sequence is selected from a SpyTag sequence selected from any one of SEQ ID NOs: 1, 3, 5, 6, 25 or 27 a protein with at least 70% sequence identity to an amino acid sequence as set forth in any one of SEQ ID NOs: 1, 3, 5, 6, 25 or 27, a SnoopTag sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

18. The method according to item 16, wherein capture sequence is a SpyCatcher sequence selected from any one of SEQ ID NOs: 1, 3, 5, 6, 26, or 28 a protein with at least 70% sequence identity to an amino acid sequence as set forth in any one of SEQ ID NOs: 1, 3, 5, 6, 26, or 28, a SnoopCatcher sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

19. The method according to any one of items 16-18, wherein said method comprises the expression of said POI on the surface of a prokaryotic cell and said anchor protein is selected from outer membrane proteins, pili, flagella, modified lipoproteins, ice nucleation proteins, autotransporters, LamB, OmpA, Lpp-OmpA, INP, FliC, FimA, Protein A, LysM, FnBPB, M6, SbpA, or RsaA;

20. The method according to any one of items 16-18, wherein said method comprises the expression of said POI on the surface of an eukaryotic cell and said anchor protein is selected from cell wall protein alpha-agglutinin 1, alpha-agglutinin 2, Cwp1, Cwp2, Gas1p, Yap3p, Flo1p, Crh2p, Pir1, Pir2, Pir4, Icwp, HpSEDI, HpGASI, HpTIPI, HPWPI, Hwplp, Als3p, Rbt5p, surface receptors, or GPI anchor sequences;

21. The method according to any one of items 16-19, wherein said POI is selected from antibodies, antibody fragments, single chain antibodies, scFv, scFab, single domain antibodies, protein scaffolds (e.g. based on fibronectin III, cystatin, lipocalins, Ankyrin repeat domains, Z domain of protein A and others), enzymes, hormones, interleukins, antigens for the development of vaccines, human growth hormone hGH), N-methionyl human growth hormone, bovine growth hormone, parathyroid hormone, thyroxine, insulin A-chain, insulin B-chain, proinsulin, relaxin A-chain, relaxin B-chain, prorelaxin, follicle stimulating hormones (FSH), thyroid stimulating hormone (TSH), leutinizing hormone (LH), glycoprotein hormone receptors, calcitonin, glucagon, factor VIII, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, a microbial protein, beta-lactamase, tissue factor protein, inhibin, activin, vascular endothelial growth factor, receptors for hormones or growth factors; integrin, thrombopoietin, protein A or D, rheumatoid factors, nerve growth factors, NGF-β, platelet-growth factor, transforming growth factors (TGF), TGF-alpha, TGF-beta, insulin-like growth factor-I or -II, insulin-like growth factor binding proteins, DNase, latency associated peptide, erythropoietin, osteoinductive factors, interferons, interferon-alpha, interferon-beta, interferon-gamma, colony stimulating factors (CSFs), M-CSF, GF-CSF, and G-CSF, interleukins (ILs), IL-1, IL-2, IL-3, IL-4, superoxide dismutase; decay accelerating factor, viral antigens, HIV envelope proteins, GP120, GP140, and atrial natriuretic peptides A, B or C;

22. The method according to item 21, wherein said POI is an antibody, antibody fragment, single chain antibody, scFv, scFab, or single domain antibody;

23. A helper phage such as VCSM13 or M13KO7 with a modification of the phage DNA to express a capture sequence-anchor sequence fusion protein or a tether sequence-anchor sequence fusion protein which can be used to infect prokaryotic cells to produce phage which carry capture or tether sequence on its surface;

24. The phage according to item 23, wherein said tethering sequence is selected from a SpyTag sequence selected from any one of SEQ ID NOs: 1, 3, 5, 6, 25 or 27 a protein with at least 70% sequence identity to an amino acid sequence as set forth in any one of SEQ ID NOs: 1, 3, 5, 6, 25 or 27, a SnoopTag sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

25. The phage according to item 23, wherein capture sequence is a SpyCatcher sequence selected from any one of SEQ ID NOs: 1, 3, 5, 6, 26 or 28 a protein with at least 70% sequence identity to an amino acid sequence as set forth in any one of SEQ ID NOs: 1, 3, 5, 6, 26 or 28, a SnoopCatcher sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

26. A prokaryotic or eukaryotic host cell with a modified genome to express a capture sequence-anchor sequence fusion protein or a tether sequence-anchor sequence fusion protein which can be used to display capture or tether sequence on its surface or on the surface of a virus or phage produced by the host cell; and/or a modified genome to express a ligase derived from SEQ ID NOs: 13, 7, 11, 9, 10 or 15 or a ligase having at least 70% sequence identity to a ligase derived from SEQ ID NOs: 13, 7, 11, 9, 10 or 15; a vector comprising a promoter operably linked to a comprising a polynucleotide encoding a sortase; or a vector comprising a promoter operably linked to a polynucleotide encoding a butelase;

27. The prokaryotic or eukaryotic host cell according to item 26, wherein said tethering sequence is selected from a SpyTag sequence selected from any one of SEQ ID NOs: 1, 3, 5, 6, 25 or 27 a protein with at least 70% sequence identity to an amino acid sequence as set forth in any one of SEQ ID NOs: 1, 3, 5, 6, 25 or 27, a SnoopTag sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein; and 28. The prokaryotic or eukaryotic host cell according to item 26, wherein capture sequence is a SpyCatcher sequence selected from any one of SEQ ID NOs: 1, 3, 5, 6, 26 or 28 a protein with at least 70% sequence identity to an amino acid sequence as set forth in any one of SEQ ID NOs: 1, 3, 5, 6, 26 or 28, a SnoopCatcher sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting.

Example 1—Covalent Capture Display

This example describes the covalent display of human Fab fragments, adalimumab and trastuzumab, with a SpyTag at the C-terminus of the heavy chain on the surface of M13 phages which have a SpyCatcher fused to the N-terminus of the pIII. SpyTag and SpyCatcher form a covalent bond within the *E. coli* that leads to a covalent linkage of the Fab to the pIII phage coat protein.

Modification of Helperphages to Produce SpyCatcher-pIII

Figure 2:
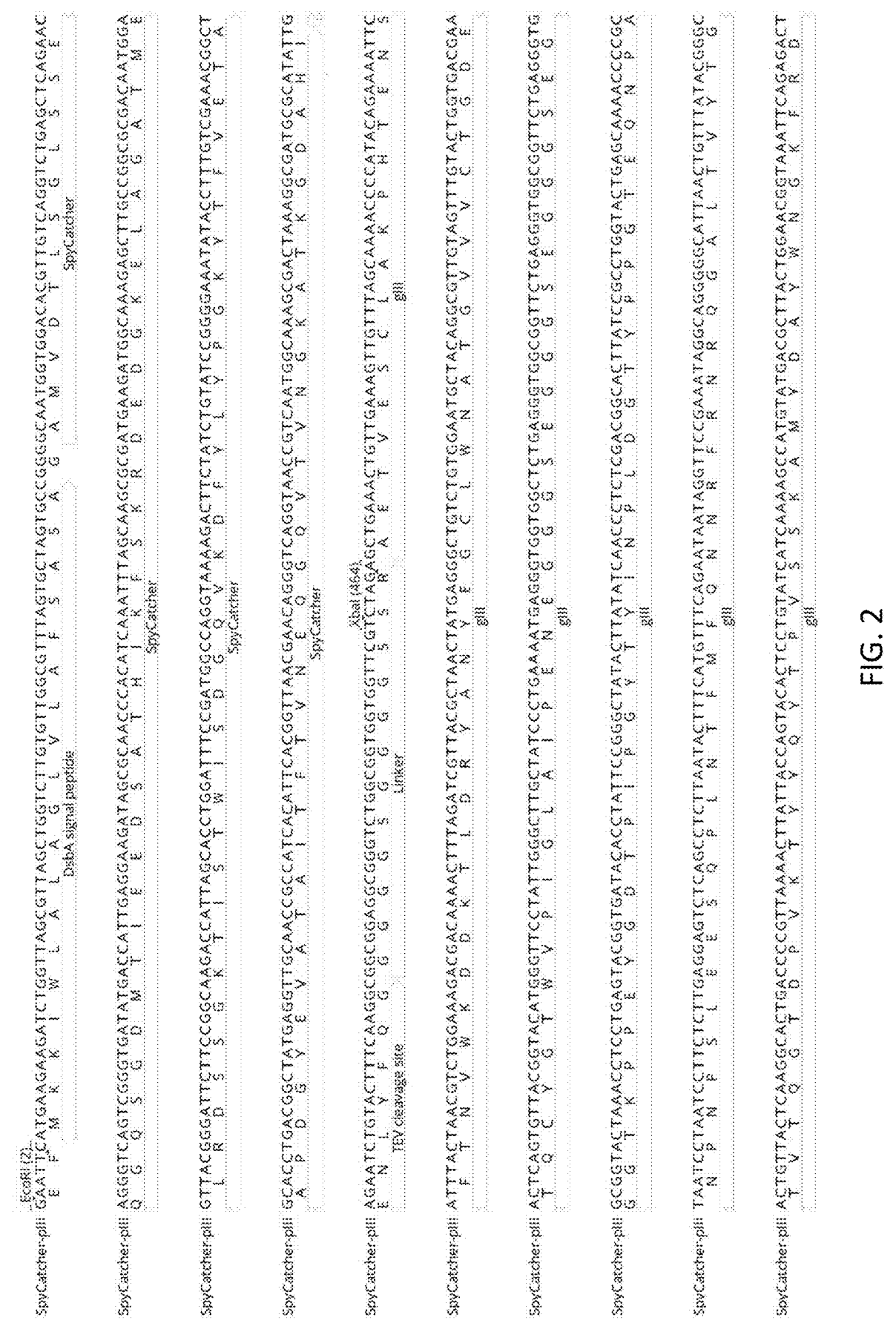
Figure 2:
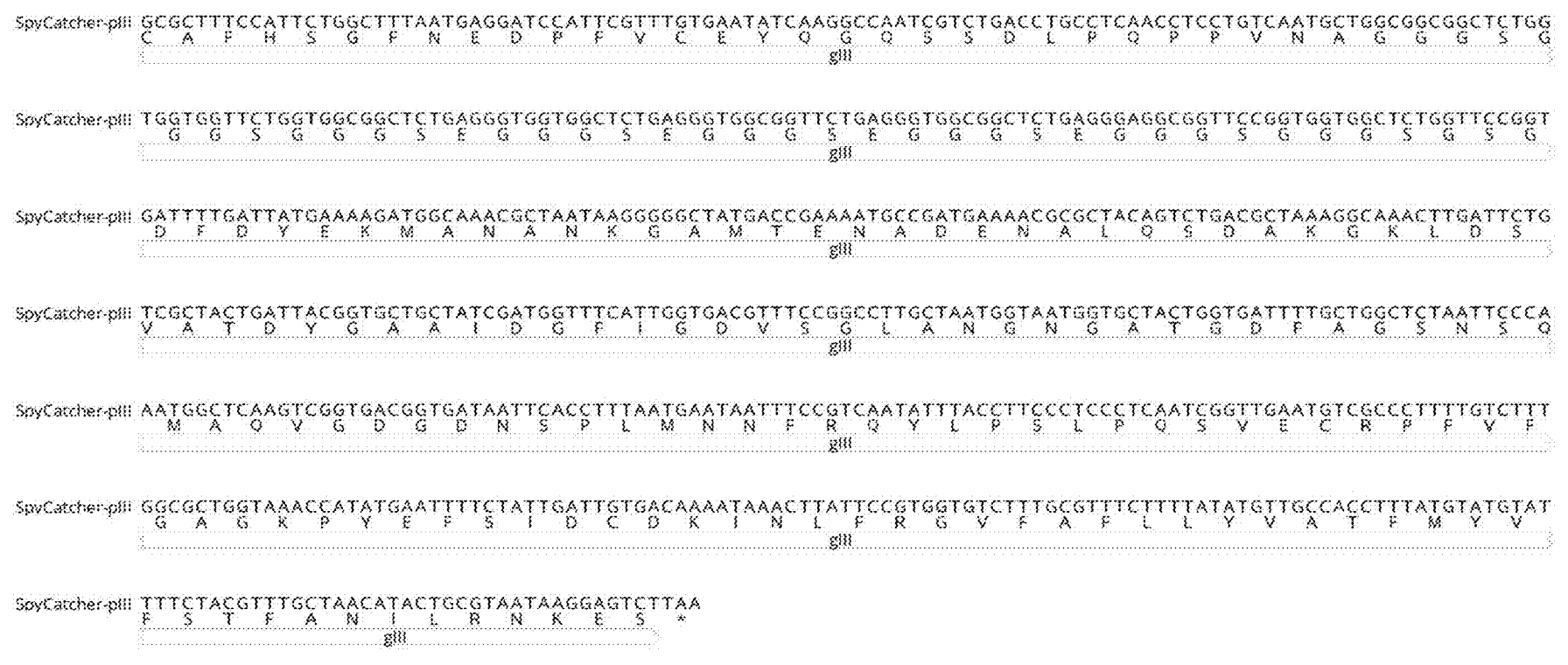

VCSM13 helperphage were modified to replace the gIII with a SpyCatcher-gIII genetic fusion. Cloning was done by ligation of restriction digested PCR products. The phage genome was PCR amplified and restriction sites were inserted with primers at the beginning of the gIII (forward primer with XbaI site) and before the start codon of the gIII (reverse primer with EcoRI site) omitting the gIII signal peptide. The inserted sequence with matching restriction sites consists of a DsbA signal peptide, SpyCatcher, TEV protease cleavage site and a short linker (GGGGSGGGS, SEQ ID NO: 33, FIG. 2). After transformation into *E. coli* XL1 Blue F' competent cells, clones with correct insert were identified by colony PCR to distinguish the shorter wt gIII from the SpyCatcher-gIII Correct insertion was confirmed by sequencing the relevant region of PCR amplified phage DNA.

Production of SpyCatcher-pIII Helperphage

XL1F' carrying the modified helperphage genome were grown in 50 ml 2×YT with kanamycin at 37° C. overnight. Next day, six 300 ml cultures were inoculated from the overnight culture to OD600 of 0.1 and grown in 2×YT with kanamycin at 37° C. to an OD600 of ~0.6 and then transferred to 18° C. for helperphage production overnight. Bacteria were spun down and phage were purified and concentrated from the supernatant by PEG precipitation as described below. The phage pellet was dissolved in 1000 µl PBS and after addition of 20% glycerol aliquots were stored at −80° C.

XL1 Blue F', MC1061 F' or TG1F' cells were grown in 2×YT to an OD600 of 0.6-0.8 and then infected with the modified helperphage for 45 min without shaking and 45 min with shaking. The culture was incubated on a shaker at 37° C. for 3-4 h and was then transferred to a larger volume of 2×YT with 50 µg/ml kanamycin (e.g. 50 ml culture and 350 ml 2×YT) for overnight phage production at 18° C. The next day, the phages were precipitated as described below, dissolved in 400 µl PBS and stored at −80° C. after addition of 20% glycerol.

Phage PEG Precipitation

Phage were precipitated from the overnight culture supernatant by addition of ¼ the volume+10% of ice cold PEG/NaCl solution (20% PEG 6000, 2.5M NaCl). Supernatant was incubated on ice on a shaker for 30 min and phages were centrifuged at 13,000×g for 60 min at 2-8° C. The supernatant was discarded and the pellet resuspended in 10 ml PBS. Remaining bacteria were removed from the phage solution by sterile filtration with a 0.22 µm filter and PEG/NaCl precipitation was repeated as described. The phage pellet was dissolved in PBS.

SpyCatcher-pIII Helperphage Analysis

1. Spot Titration

Phage titer and infectivity were determined by spot titration and by ELISA. For spot titration, a culture was inoculated with a TG1F' colony from a M9 minimal agar plate and grown to OD600 of 0.6-0.8 at 37° C. A 1:10 dilution series of the helperphage in 2×YT was prepared and 10 µl of the dilution was mixed with 90 µl TG1F' culture, incubated at 37° C. for 30 min and then 5 µl were plated on a LB agar plate containing 1% glucose and 50 µg/ml kanamycin and incubated at 37° C. overnight. Unmodified VCSM13 helperphages were used as a reference. Colonies in spots with less than 30 colonies were counted and the titer was calculated according to the dilution and used volumes. Titers were ~$10^{11}$ cfu/ml.

2. ELISA

Determination of the phage titer and proof of display of the SpyCatcher on the phage surface was done by ELISA. An ELISA microtiter plate was coated at 4° C. overnight with an anti-M13 antibody (anti-pVIII, 1 µl/ml in PBS) and anti-SpyCatcher Fab (5 µg/ml in PBS), respectively. After blocking with Chemiblocker in TBST at room temperature for 1-2 h, a 1:2 dilution series of modified helperphage and wt VCSM13 helperphage with known titer were added to the ELISA plate and incubated at room temperature for 1 h. Detection was performed with an anti-M13 HRP detection antibody and QuantaBlu peroxidase fluorescence substrate. The titer estimated by this method was at ~$5 \times 10^{13}$ phage/ml. The ELISA with anti-SpyCatcher capture antibody gave a strong signal thus confirming the presence of phage with one or more SpyCatchers displayed on the surface.

3. Western Blot

Presence of the SpyCatcher on the surface of the phage was also confirmed by Western blot of denatured phage with an anti-SpyCatcher antibody and an anti-pIII antibody, respectively. A Bio-Rad Mini-PROTEAN™ Vertical Electrophoresis Cell was used along with a Mini-Protean TGX 4-20% gel and the Bio-Rad Precision Plus Protein Standard molecular weight marker. Proteins were blotted to a PVDF membrane by using the Bio-Rad Trans-Blot Turbo Transfer System. The membrane was blocked with milk in TBST for 1 h on a shaker followed by incubation for 1 h with either one of the two primary antibodies. Secondary antibody for the anti-SpyCatcher primary was an HRP conjugated anti-hFab antibody, for anti-pIII an HRP conjugated anti-mouse IgG antibody was used. Clarity Western ECL substrate was used for detection.

Figure 3:
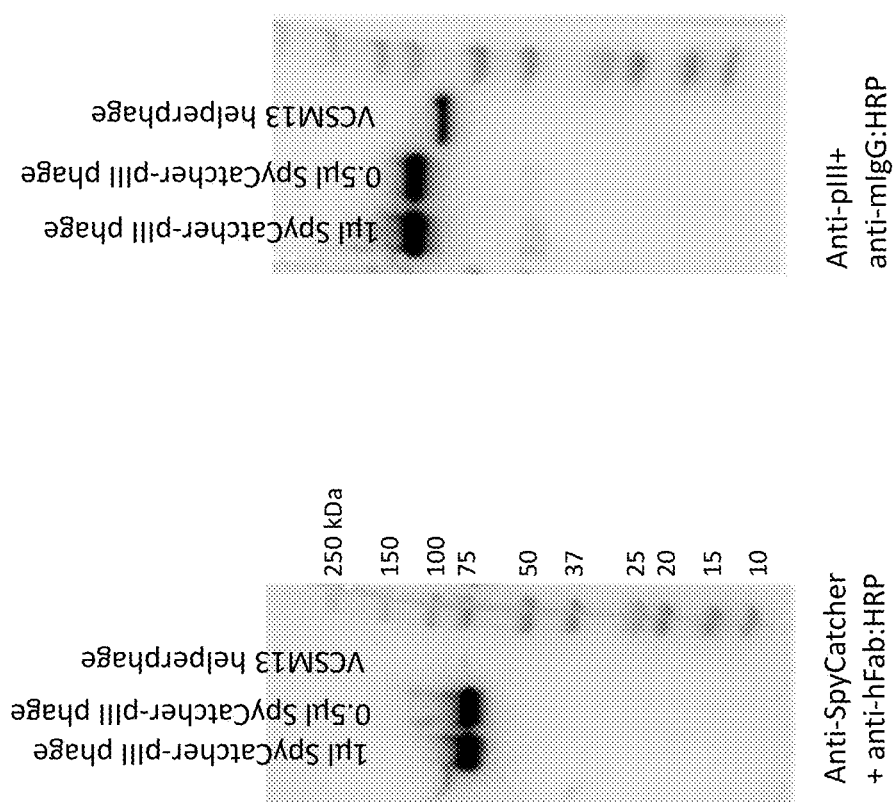
FIGS. 3A-3B illustrate Western blot analysis of SpyCatcher phage compared to VCSM13 phage.

The Western blot with anti-SpyCatcher detection shows a band for SpyCatcher phages only but not for VCSM13 phages (negative control; FIG. 3A). The blot with anti-pIII detection shows that the pIII band in SpyCatcher phages runs higher than VCSM13 phages. The shift equaled the increase in molecular weight by the SpyCatcher fused to the pIII (FIG. 3B).

Fab-SpyTag Constructs

Human Fab antibody fragments (trastuzumab and adalimumab) with a SpyTag (Spy) and hexahistidine tag (H) at the C-terminus of the heavy chain were cloned into a bicistronic expression vector pBBx1, consisting of a lac promoter, Shine-Dalgarno (SD) sequence, start codon, pelB leader sequence, Fab light chain stop codon, SD sequence, start codon, ompA leader sequence Fab heavy chain, SpyTag, His tag, and stop codon. The vector furthermore carries a ColE1 and f1 origin of replication, a chloramphenicol resistance and lac repressor (LacI).

Covalent Capture Display

The plasmids described above were transformed into TG1F' cells. A freshly inoculated culture was grown overnight in 5 ml 2×YT with chloramphenicol and 1% glucose at 37° C. on a shaker. Next day, a 100 ml culture was inoculated with this preculture to an OD600 of 0.05 and grown at 37° C. to an OD600 of 0.5. 50 ml of this culture were infected with SpyCatcher-pIII helperphages at 37° C. for 45 min without shaking and 45 min with shaking. Bacteria were spun down and the supernatant was discarded. The pellet was resuspended in 300 ml 2×YT with chloramphenicol, kanamycin, and 0.25 mM IPTG and cultured overnight at 30° C. for phage production. Bacteria were spun down and phages were PEG precipitated from the supernatant as described before. The phage pellet was dissolved in 500-1000 μl PBS and stored at −80° C. after addition of 20% glycerol.

Analysis of Covalent Capture Display Fab Phages

1. Spot Titration

Spot titration was performed as described for the SpyCatcher-pIII phages. Titers were in the range of $1-3 \times 10^{13}$ cfu.

2. ELISA

Phage ELISA was performed as described above for the SpyCatcher-pIII phages. Fab displaying phages with known titer were used as a standard to determine the phage titer. Titers determined with this method were in the range of $1 \times 10^{14}$ phages/ml.

Instead of the anti-SpyCatcher antibody an anti-Fd capture antibody was used for the second ELISA. This antibody can capture phages which carry a Fab heavy chain (Fd) on the surface of the phages and thus this assay confirms a successful Fab covalent capture display. This ELISA gave a strong signal thus indicating a good display rate of most likely several Fab per phage.

3. Western Blot

Figure 4:
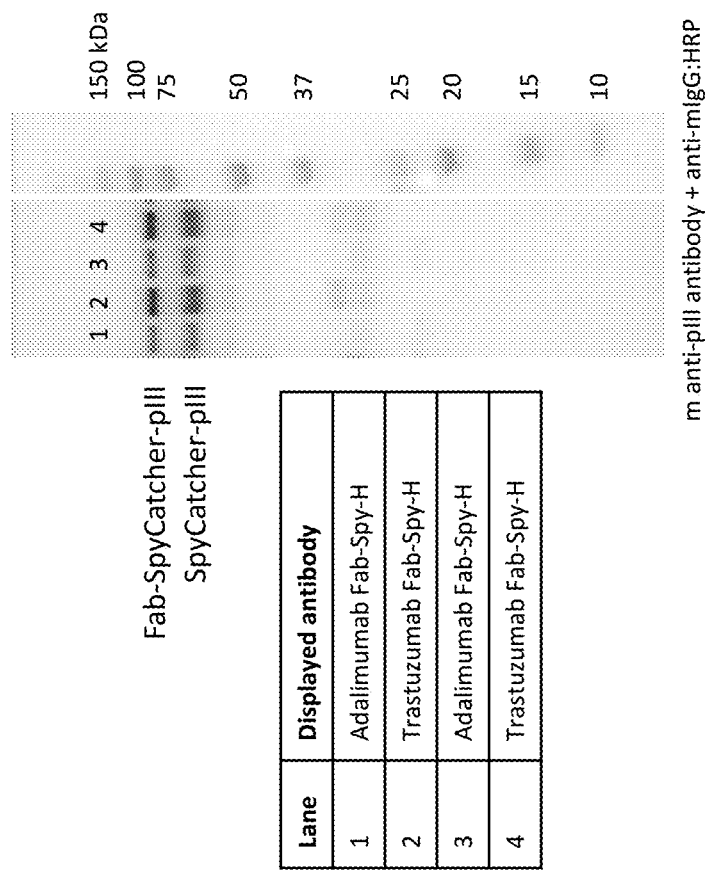
FIG. 4 is a Western blot of Fab phages. The Fab expressing phages were analyzed by Western blot with an anti-pIII antibody. Two main bands are visible, the Fab-SpyTag- SpyCatcher-pIII and SpyCatcher-pIII fusion protein (FIGS. 3A-3B). The intensity ratio of the two bands indicates an average display rate of approximately 2 Fab per phage (each phage carries ~5 pIII proteins at the tip of the coat).

Fab phages were analyzed by Western blot with an anti-pIII antibody. Western blot was performed as described above for SpyCatcher-pIII phages. Two main bands are visible, the Fab-SpyTag-SpyCatcher-pIII and SpyCatcher-pIII fusion protein (FIG. 4). The intensity ratio of the two bands indicates an average display rate of approximately 2 Fab per phage (each phage carries ~5 pIII proteins at the tip of the coat).

4. Functionality—Antigen Binding

Figure 5:
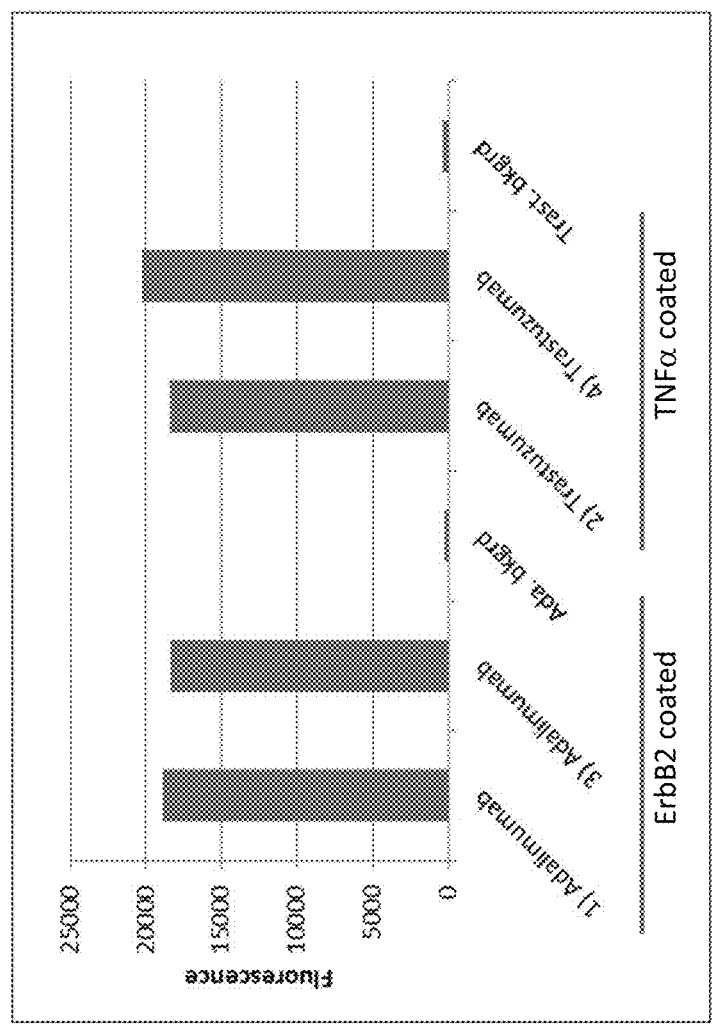
FIG. 5 demonstrates proper folding of the Fab on the surface of the phage. Fab displaying phages were analyzed by ELISA for antigen binding capability (TNFα for Adalimumab and ErbB2 for Trastuzumab). Both Fab phages demonstrated a strong signal over background value which confirms the functionality of the Fab on the surface of the phage.

To confirm proper folding of the Fab on the surface of the phage, Fab displaying phages were also analyzed by ELISA for antigen binding capability. Fab antigens, TNF-α for Adalimumab and ErbB2 for Trastuzumab, were coated on an ELISA plate at 5 μg/ml in PBS overnight at 4° C. After blocking with Chemiblocker in TBST for 1 h, the plate was incubated with a 1:500 dilution of the Fab phage in TBST for 1 h. Phages were detected with an HRP-conjugated anti-M13 antibody and QuantaBlu fluorescence substrate. For both Fab phages a strong signal over background value confirmed functionality of the Fab on the surface of the phage (FIG. 5).

5. Phagemid DNA Retrieval after Phage Infection

To confirm that the Fab-displaying phages carry the phagemid TG1F' was infected with the Fab phages and DNA of single colonies was analyzed for phagemid by PCR.

1 ml of a culture of TG1F' in 2×YT at OD600 of 0.4-0.6 was infected with 10 μl Fab phages and incubated at 37° C. without shaking for 45 min followed by 45 min with shaking. Different amounts of this culture (10 μl, 1 μl, and 0.1 μl) were plated on LB agar plates with chloramphenicol and glucose. Single colonies were picked for a colony-PCR with primers which anneal in the pBBx1 phagemid. The presence of a PCR product of correct size was confirmed for all colonies by agarose gel electrophoresis.

REFERENCES

Bastien, N., Trudel, M., and Simard, C., 1997, Protective immune responses induced by the immunization of mice with a recombinant bacteriophage displaying an epitope of the human respiratory syncytial virus. Virology 234: 118-122.

Batonick, M., Kiss, M. M., Fuller, E. P., Magadan, C. M., Holland, E. G., Zhao, Q., Wang, D., Kay, B. K., Weiner, M. P., 2016, pMINERVA: A donor-acceptor system for the in vivo recombineering of scFv into IgG molecules. J Immunol Methods 431:22-30.

Benhar, I., 2001, Biotechnological applications of phage and cell display. Biotechnol Adv 19:1-33

Borodina, I., Jensen, B. M., Søndergaard, I., and Poulsen, L. K., 2010, Display of wasp venom allergens on the cell surface of Saccharomyces cerevisiae. Microb Cell Fact 9:74.

Caspi, J. et al., 2003, Distribution of split DnaE inteins in cyanobacteria. Mol Microbiol. 50: 1569-1577.

Chang and Lo, 2000, Modification with a phosphorylation tag of PKA in the TraT-based display vector of Escherichia coli. J Biotechnol 78:115-122.

Chen, W. and Georgiou, G., 2002, Cell-surface display of heterologous proteins: From high-throughput screening to environmental applications. Biotechnol Bioeng 79:496-503.

Chesnut, J. D. et al., 1996, Selective isolation of transiently transfected cells from a mammalian cell population with vectors expressing a membrane anchored single-chain antibody. J Immunological Methods. 193(1):17-27.

Choi, J. et al., 2006, Protein Trans-splicing and Characterization of a Split Family B-type DNA Polymerase from the Hyperthermophilic Archaeal Parasite Nanoarchaeum equitans. J Mol Biol. 356: 1093-1106.

Dassa, B. et al., 2007, Trans Protein Splicing of Cyanobacterial Split Inteins in Endogenous and Exogenous Combinations. Biochemistry. 46:322-330.

Duc, L. H., Hong, H. A., Atkins, H. S., Flick-Smith, H. C., Durrani, Z., Rijpkema, S., et al., 2007, Immunization against anthrax using Bacillus subtilis spores expressing the anthrax protective antigen. Vaccine 25:346-355.

Fierer, J. O., Veggiani, G., Howarth, M., 2014, SpyLigase peptide-peptide ligation polymerizes affibodies to enhance magnetic cancer cell capture. Proc Natl Acad Sci USA. 111:E1176-1181.

Gao, C. S., Mao, S. L., Lo, C. H. L., Wirsching, P., Lerner, R. A., Janda, K. D., 1999, Making artificial antibodies: A format for phage display of combinatorial heterodimeric arrays. PNAS 96(11):6025-30.

Georgiou, G. et al., 1996, Display of β-lactamase on the Escherichia coli surface: outer membrane phenotypes conferred by Lpp'-OmpA'-β-lactamase fusions. Protein Eng 9: 239-247.

Gleiter, S., and Lilie, H., 2001, Coupling of antibodies via protein Z on modified polyoma virus-like particles. Protein Sci 10:434-444.

Ho, M. et al, 2006, Isolation of anti-CD22 Fv with high affinity by Fv display on human cells. PNAS, 103:9637-9642.

Ilk, N., Schumi, C. T., Bohle, B., Egelseer, E. M., and Sleytr, U. B., 2011, Expression of an endotoxin-free S-layer/allergen fusion protein in gram-positive Bacillus subtilis 1012 for the potential application as vaccines for immunotherapy of atopic allergy. Microb Cell Fact 10:6.

Isticato, R., Cangiano, G., Tran, H. T., Ciabattini, A., Medaglini, D., Oggioni, M. R. et al., 2001, Surface display of recombinant proteins on *Bacillus subtilis* spores. J Bacteriol 183:6294-6301.

Jung, H. C. et al., 1998, Surface display of *Zymomonas mobilis* levansucrase by using the ice-nucleation protein of *Pseudomonas syringae*. Nat Biotechnol 16:576-580.

Keeble, A. H., Banerjee, A., Ferla, M. P., Reddington, S. C., Khairil Anuar, I. N. A., Howarth, M., 2017, Evolving accelerated amidation by SpyTag/SpyCatcher to analyze membrane dynamics. Ange, Chem. Int. Ed. 56:16521-16525.

Koutsky, L. A., Ault, K. A., Wheeler, C. M., Brown, D. R., Barr, E., Alvarez, F. B. et al., 2002, A controlled trial of a human papillomavirus type 16 vaccine. N Engl J Med 347:1645-1651.

Lee, S. H. et al., 2004, Display of Bacterial Lipase on the *Escherichia coli* Cell Surface by Using FadL as an Anchoring Motif and Use of the Enzyme in Enantioselective Biocatalysis. Appl Environ Microbiol 70:5074-5080.

Li, L., Kang, D. G., and Cha, H. J., 2003, Functional display of foreign protein on surface of *Escherichia coli* using N-terminal domain of ice nucleation protein. Biotechnol Bioeng 85:214-221.

Little, M. et al., 1994, Surface display of antibodies, Biotechnol Adv. 12(3):539-555.

Liu, X. and Yang J., 2003, Split dnaE Genes Encoding Multiple Novel Inteins in *Trichodesmium erythraeum*. J Biol Chem. 278:26315-26318.

Lu, Z., Murray, K. S., Cleave, V. V., LaVallie, E. R., Stahl, M. L., and McCoy, J. M., 1995, Expression of thioredoxin random peptide libraries on the *Escherichia coli* surface as functional fusions to flagellin: a system designed for exploring protein-protein interactions. Bio/Technology 13:366-372.

Matsumoto, T., Fukuda, H., Ueda, M., Tanaka, A., and Kondo, A., 2002, Construction of yeast strains with high cell surface lipase activity by using novel display systems based on the Flo1p flocculation functional domain. Appl Environ Microbiol 68:4517-4522.

Mauriello, E. M., Duc, L. H., Isticato, R., Cangiano, G., Hong, H. A., De, F. M. et al., 2004, Display of heterologous antigens on the *Bacillus subtilis* spore coat using CotC as a fusion partner. Vaccine 22:1177-1187.

Mazor, Y., Van Blarcom, T., Carroll, S., Georgiou, G., 2010, Selection of full-length IgGs by tandem display on filamentous phage particles *Escherichia coli* fluorescence-activated cell sorting screening. The FEBS Journal. 277 (10):2291-2303.

McCafferty, J., Griffiths, A. D., Winter, G., and Chiswell, D. J., 1990, Phage antibodies: filamentous phage displaying antibody variable domains. Nature 348:552-554.

Nguyen, G. K. T., Wang, S., Qiu, Y., Hemu, X., Lian, Y., Tam, J. P., 2014, Butelase 1 is an Asx-specific ligase enabling peptide macrocyclization and synthesis. Nat Chem Biol. 10:732-738.

Nomellini, J. F., Duncan, G., Dorocicz, I. R., and Smit, J., 2007, S-layer-mediated display of the immunoglobulin G-binding domain of streptococcal protein G on the surface of *Caulobacter crescentus*: development of an immunoactive reagent. Appl Environ Microbiol 73:3245-3253.

Qi, H., Lu, H., Qiu, H. J., Petrenko, V., Liu, A., 2012, Phagemid vectors for phage display: properties, characteristics and construction. J Mol Biol. 417(3):129-143.

Reddington, S. C., Howarth, M., 2015, Secrets of a covalent interaction for biomaterials and biotechnology: SpyTag and SpyCatcher. Current opinion in chemical biology. 29:94-99.

Rondot, S., Koch, J., Breitling, F., Dubel, S., 2001, A helper phage to improve single-chain antibody presentation in phage display. Nat Biotechnol. 19(1):75-78.

Rothe, C., Urlinger, S., Lohning, C., Prassler, J., Stark, Y., Jager, U. et al., 2008, The human combinatorial antibody library HuCAL GOLD combines diversification of all six CDRs according to the natural immune system with a novel display method for efficient selection of high-affinity antibodies. J Mol Biol. 376(4):1182-1200.

Samuelson, P., Gunneriusson, E., Nygren, P. A., and Stahl, S., 2002, Display of proteins on bacteria. J Biotechnol 96:129-154.

Schmohl, L., Schwarzer, D., 2014, Sortase-mediated ligations for the site-specific modification of proteins. Current Opinion in Chemical Biology. 22:122-128.

Shao, X., Jiang, M., Yu, Z., Cai, H., and Li, L., 2009, Surface display of heterologous proteins in *Bacillus thuringiensis* using a peptidoglycan hydrolase anchor. Microb Cell Fact 8:48.

Shimojo, R., Furukawa, H., Fukuda, H., and Kondo, A., 2004, Preparation of yeast strains displaying IgG binding domain ZZ and EGFP for novel antigen detection system. J Biosci Bioeng 96:493-495.

Steidler, L., Viaene, J., Fiers, W., and Remaut, E., 1998, Functional display of a heterologous protein on the surface of *Lactococcus lactis* by means of the cell wall anchor of *Staphylococcus aureus* protein A. Appl Environ Microbiol 64:342-345.

Strauss, A. and Gotz. F., 1996, In vivo immobilization of enzymatically active polypeptides on the cell surface of *Staphylococcus carnosus*. Mol Microbiol 21:491-500.

Tesar, D., Hotzel, I., 2013, A dual host vector for Fab phage display and expression of native IgG in mammalian cells. Protein Eng Des Sel 26:655-662.

Thiel, I. V., Volkmann, G., Pietrokovski, S., Mootz, H. D., 2014, An atypically split intein engineered for a highly efficient protein labeling. Angew Chem Int Ed Engl. 53:1306-1310.

Toplak, A., Nuljens, T., Quaedflieg, P. J. L., Wu, B., Janssen, D. B., 2016, Peptiligase, an enzyme foe efficient chemoenzymatic peptide synthesis and cyclization in water. Adv Synth Catal. 358:32140-32147.

Tornetta, M., Reddy, R., Wheeler, J. C., 2012, Selection and maturation of antibodies by phage display through fusion to pIX. Methods 58(1):34-9.

Veggiani, G. et al., 2016, Programmable polyproteams built using twin peptide superglues. Proc Natl Acad Sci USA 113:1202-1207.

Veiga, E. et al., 2003, Autotransporters as Scaffolds for Novel Bacterial Adhesins: Surface Properties of *Escherichia coli* Cells Displaying Jun/Fos Dimerization Domains. J Bacteriol 185:5585-5590.

Wang, K. C., Wang, X., Zhong, P., Luo, P. P., 2010, Adapter-directed display: a modular design for shuttling display on phage surfaces. J Mol Biol. 395:1088-1101.

Ward, R. L., Clark, M. A., Lees, J., Hawkins, N. J., 1996, Retrieval of human antibodies from phage-display libraries using enzymatic cleavage. J Immunol Methods. 189 (1):73-82.

Wen, F., Sun, J., and Zhao, H., 2010, Yeast surface display of trifunctional minicellulosomes for simultaneous saccharifi-cation and fermentation of cellulose to ethanol. Appl Environ Microbiol 76:1251-1260.

Westerlund-Wikstrom, B. et al., 1997, Functional expression of adhesive peptides as fusions to *Escherichia coli* flagellin. Protein Eng 10:1319-1326.

Wieczorek, A. S., and Martin, V. J. J. (2010) Engineering the cell surface display of cohesins for assembly of cellulosome-inspired enzyme complexes on *Lactococcus lactis*. Microb Cell Fact 9:69.

Wu, H. et al., 1998, Protein trans-splicing by a split intein encoded in a split DnaE gene of *Synechocystis* sp. PCC6803. Proc Natl Acad Sci USA. 95:9226-9231.

Zakeri, B. et al., 2012, Peptide tag forming a rapid covalent bond to a protein, through engineering a bacterial adhesion. Proc Natl Acad Sci USA. 109:E690-697.

Zettler, J. et al., 2009, The Naturally Split Npu DnaE Intein Exhibits an Extraordinarily High Rate in the Protein Trans-Splicing Reaction. FEBS Letters. 553:909-914.

---

I claim:

1. A combination of vectors comprising:
   a) a first vector comprising a genetic construct (GC1) comprising polynucleotide encoding a protein of interest (POI) fused, in frame, to a tether sequence; and
   b) a second vector comprising a genetic construct (GC2) comprising polynucleotide encoding an anchor protein fused, in frame, to a capture sequence,
   the tether sequence and capture sequence forming a covalent bond when brought into contact with one another either spontaneously or with the help of an enzyme; or
   a combination of vectors comprising:
   a) a first vector comprising a genetic construct (GC1) comprising polynucleotide encoding a protein of interest (POI) fused, in frame, to a capture sequence; and
   b) a second vector comprising a genetic construct (GC2) comprising polynucleotide encoding an anchor protein fused, in frame, to a tether sequence,
   the tether sequence and capture sequence forming a covalent bond when brought into contact with one another either spontaneously or with the help of an enzyme;
   the POI being selected from antibodies, antibody fragments, single chain antibodies, scFv, scFab, or single domain antibodies and the anchor protein being selected from pIII, pVI, pVII, pVIII, or pIX.

2. The combination of vectors according to claim 1, wherein each vector comprises transcriptional or translational control sequences for expressing the POI and anchor protein.

3. The combination of vectors according to claim 1, wherein said transcription or translational control sequences are selected from replication origins, promoters, enhancers, repressor binding regions, transcription initiation sites, ribosome binding sites, translation initiation sites, and termination sites for transcription and translation.

4. The combination of vectors according to claim 1, wherein said POI is selected from the group consisting of antibody fragments, single chain antibodies, scFv, scFab, and single domain antibodies.

5. The combination of vectors according to claim 2, wherein:
   a) the tethering sequence comprises SEQ ID NO: 27 or comprises a tethering sequence having at least 70% sequence identity to SEQ ID NO: 27 and the capture sequence comprises SEQ ID NO: 28 or a polypeptide having at least 70% identity to SEQ ID NO: 28;
   b) the tethering sequence comprises between 5 and 50 consecutive amino acids of SEQ ID NO: 6, said tethering sequence including the aspartic acid residue at position 101 or a tethering sequence having at least 70% identity to said tethering sequence and the capture sequence comprises amino acids 22-137 of SEQ ID NO: 30; or
   c) the tethering sequence comprises SEQ ID NO: 34 or a tethering sequence at least 70% identical thereto and the capture sequence comprises amino acids 22-137 of SEQ ID NO: 30.

6. The combination of vectors according to claim 1, wherein said anchor protein is pIII.

7. A prokaryotic host cell comprising a combination of vectors according to claim 1.

8. The combination of vectors according to claim 5, wherein the tethering sequence comprises SEQ ID NO: 27 and the capture sequence comprises SEQ ID NO: 28.

9. The combination of vectors according to claim 5, wherein the tethering sequence comprises between 5 and 50 consecutive amino acids of SEQ ID NO: 6 and includes the aspartic acid residue at position 101 and the capture sequence comprises amino acids 22-137 of SEQ ID NO: 30.

10. The combination of vectors according to claim 5, wherein the tethering sequence comprises SEQ ID NO: 34 and the capture sequence comprises amino acids 22-137 of SEQ ID NO: 30.

11. The combination of vectors according to claim 1, said combination of vectors comprising:
 a) a first vector comprising a genetic construct (GC1) comprising polynucleotide encoding a protein of interest (POI) fused, in frame, to a tether sequence; and
 b) a second vector comprising a genetic construct (GC2) comprising polynucleotide encoding an anchor protein fused, in frame, to a capture sequence,
 the tether sequence and capture sequence forming a covalent bond when brought into contact with one another either spontaneously or with the help of an enzyme.

12. The combination of vectors according to claim 11, wherein:
 a) said first vector comprising a genetic construct (GC1) comprising polynucleotide encoding a protein of interest (POI) fused, in frame, to a tether sequence is an expression vector; and
 b) said second vector comprising a genetic construct (GC2) comprising polynucleotide encoding an anchor protein fused, in frame, to a capture sequence is a helper vector.

13. The combination of vectors according to claim 12, wherein the tethering sequence comprises SEQ ID NO: 27 and the capture sequence comprises SEQ ID NO: 28.

14. The combination of vectors according to claim 12, wherein the tethering sequence comprises between 5 and 50 consecutive amino acids of SEQ ID NO: 6, said tethering sequence including the aspartic acid residue at position 101 or a tethering sequence having at least 70% identity to said tethering sequence and the capture sequence comprises amino acids 22-137 of SEQ ID NO: 30.

15. The combination of vectors according to claim 12, wherein the tethering sequence comprises SEQ ID NO: 34 and the capture sequence comprises amino acids 22-137 of SEQ ID NO: 30.

16. The prokaryotic host cell according to claim 7, said combination of vectors comprising:
 a) a first vector comprising a genetic construct (GC1) comprising polynucleotide encoding a protein of interest (POI) fused, in frame, to a tether sequence; and
 b) a second vector comprising a genetic construct (GC2) comprising polynucleotide encoding an anchor protein fused, in frame, to a capture sequence,
 the tether sequence and capture sequence forming a covalent bond when brought into contact with one another either spontaneously or with the help of an enzyme.

17. The prokaryotic host cell according to claim 16, wherein:
 a) said first vector comprising a genetic construct (GC1) comprising polynucleotide encoding a protein of interest (POI) fused, in frame, to a tether sequence is an expression vector; and
 b) said second vector comprising a genetic construct (GC2) comprising polynucleotide encoding an anchor protein fused, in frame, to a capture sequence is a helper vector that is integrated into the prokaryotic host cell genome.

18. The prokaryotic host cell according to claim 17, wherein the tethering sequence comprises SEQ ID NO: 27 and the capture sequence comprises SEQ ID NO: 28.

19. The prokaryotic host cell according to claim 17, wherein the tethering sequence comprises between 5 and 50 consecutive amino acids of SEQ ID NO: 6, said tethering sequence including the aspartic acid residue at position 101 or a tethering sequence having at least 70% identity to said tethering sequence and the capture sequence comprises amino acids 22-137 of SEQ ID NO: 30.

20. The prokaryotic host cell according to claim 17, wherein the tethering sequence comprises SEQ ID NO: 34 and the capture sequence comprises amino acids 22-137 of SEQ ID NO: 30.

21. The combination of vectors according to claim 1, said combination of vectors comprising:
 a) a first vector comprising a genetic construct (GC1) comprising polynucleotide encoding a protein of interest (POI) fused, in frame, to a capture sequence; and
 b) a second vector comprising a genetic construct (GC2) comprising polynucleotide encoding an anchor protein fused, in frame, to a tether sequence,
the tether sequence and capture sequence forming a covalent bond when brought into contact with one another either spontaneously or with the help of an enzyme;
the POI being selected from antibodies, antibody fragments, single chain antibodies, scFv, scFab, or single domain antibodies and the anchor protein being selected from pIII, pVI, pVII, pVIII, or pIX.

* * * * *

SEQUENCE LISTING

```
<160> NUMBER OF SEQ ID NOS: 48

<210> SEQ ID NO 1
<211> LENGTH: 340
<212> TYPE: PRT
<213> ORGANISM: Streptococcus pyogenes

<400> SEQUENCE: 1

Met Lys Leu Arg His Leu Leu Leu Thr Gly Ala Ala Leu Thr Ser Phe
1               5                   10                  15

Ala Ala Thr Thr Val His Gly Glu Thr Val Val Asn Gly Ala Lys Leu
            20                  25                  30

Thr Val Thr Lys Asn Leu Asp Leu Val Asn Ser Asn Ala Leu Ile Pro
        35                  40                  45

Asn Thr Asp Phe Thr Phe Lys Ile Glu Pro Asp Thr Thr Val Asn Glu
    50                  55                  60

Asp Gly Asn Lys Phe Lys Gly Val Ala Leu Asn Thr Pro Met Thr Lys
65                  70                  75                  80

Val Thr Tyr Thr Asn Ser Asp Lys Gly Gly Ser Asn Thr Lys Thr Ala
                85                  90                  95

Glu Phe Asp Phe Ser Glu Val Thr Phe Glu Lys Pro Gly Val Tyr Tyr
            100                 105                 110

Tyr Lys Val Thr Glu Glu Lys Ile Asp Lys Val Pro Gly Val Ser Tyr
        115                 120                 125

Asp Thr Thr Ser Tyr Thr Val Gln Val His Val Leu Trp Asn Glu Glu
    130                 135                 140

Gln Gln Lys Pro Val Ala Thr Tyr Ile Val Gly Tyr Lys Glu Gly Ser
145                 150                 155                 160

Lys Val Pro Ile Gln Phe Lys Asn Ser Leu Asp Ser Thr Thr Leu Thr
                165                 170                 175

Val Lys Lys Lys Val Ser Gly Thr Gly Gly Asp Arg Ser Lys Asp Phe
            180                 185                 190

Asn Phe Gly Leu Thr Leu Lys Ala Asn Gln Tyr Tyr Lys Ala Ser Glu
        195                 200                 205

Lys Val Met Ile Glu Lys Thr Thr Lys Gly Gly Gln Ala Pro Val Gln
    210                 215                 220

Thr Glu Ala Ser Ile Asp Gln Leu Tyr His Phe Thr Leu Lys Asp Gly
225                 230                 235                 240

Glu Ser Ile Lys Val Thr Asn Leu Pro Val Gly Val Asp Tyr Val Val
                245                 250                 255

Thr Glu Asp Asp Tyr Lys Ser Glu Lys Tyr Thr Thr Asn Val Glu Val
            260                 265                 270

Ser Pro Gln Asp Gly Ala Val Lys Asn Ile Ala Gly Asn Ser Thr Glu
        275                 280                 285

Gln Glu Thr Ser Thr Asp Lys Asp Met Thr Ile Thr Phe Thr Asn Lys
```

```
                290                 295                 300
Lys Asp Phe Glu Val Pro Thr Gly Val Ala Met Thr Val Ala Pro Tyr
305                 310                 315                 320

Ile Ala Leu Gly Ile Val Ala Val Gly Gly Ala Leu Tyr Phe Val Lys
                325                 330                 335

Lys Lys Asn Ala
            340

<210> SEQ ID NO 2
<211> LENGTH: 1023
<212> TYPE: DNA
<213> ORGANISM: Streptococcus pyogenes

<400> SEQUENCE: 2
atgaaattac gtcacttact attaacggga gcagccctaa ctagttttgc tgctacaaca      60
gttcacgggg agactgttgt aaacggagcc aaactaacag ttacaaaaaa ccttgattta     120
gttaatagca atgcattaat tccaaataca gattttacat ttaaaatcga acctgatact     180
actgtcaacg aagacggaaa taagtttaaa ggtgtagctt gaacacacc gatgactaaa      240 gtcacttaca ccaattcaga taaggtgga tcaaatacga aaactgcaga atttgatttt      300
tcagaagtta cttttgaaaa accaggtgtt tattattaca agtaactga ggagaagata      360 gataaagttc ctggtgtttc ttatgataca acatcttaca ctgttcaagt tcatgtcttg     420
tggaatgaag agcaacaaaa accagtagct acttatattg ttggttataa agaaggtagt     480
aaggtgccaa ttcagttcaa aaatagctta gattctacta cattaacggt gaagaaaaaa     540
gtttcaggta ccggtggaga tcgctctaaa gattttaatt ttggtctgac tttaaaagca     600
aatcagtatt ataaggcgtc agaaaaagtc atgattgaga agacaactaa aggtggtcaa     660
gctcctgttc aaacagaggc tagtatagat caactctatc attttacctt gaaagatggt     720
gaatcaatca agtcacaaa tcttccagta ggtgtggatt atgttgtcac tgaagacgat     780
tacaaatcag aaaaatatac aaccaacgtg gaagttagtc ctcaagatgg agctgtaaaa    840
aatatcgcag gtaattcaac tgaacaagag acatctactg ataaagatat gaccattact    900
tttacaaata aaaagacttt tgaagtgcca acaggagtag caatgactgt ggcaccatat    960
attgctttag gaattgtagc agttggtgga gctctcttact ttgttaaaaa gaaaaatgct   1020
taa                                                                 1023

<210> SEQ ID NO 3
<211> LENGTH: 674
<212> TYPE: PRT
<213> ORGANISM: Enterococcus faecalis

<400> SEQUENCE: 3

Met Thr Lys Ser Val Lys Phe Leu Val Leu Leu Val Met Ile Leu
1               5                   10                  15

Pro Ile Ala Gly Ala Leu Leu Ile Gly Pro Ile Ser Phe Gly Ala Glu
            20                  25                  30

Leu Ser Lys Ser Ser Ile Val Asp Lys Val Glu Leu Asp His Thr Thr
        35                  40                  45

Leu Tyr Gln Gly Glu Met Thr Ser Ile Lys Val Ser Phe Ser Asp Lys
    50                  55                  60

Glu Asn Gln Lys Ile Lys Pro Gly Asp Thr Ile Thr Leu Thr Leu Pro
65                  70                  75                  80

Asp Ala Leu Val Gly Met Thr Glu Asn Asp Ser Ser Pro Arg Lys Ile
```

```
                    85                  90                  95
Asn Leu Asn Gly Leu Gly Glu Val Phe Ile Tyr Lys Asp His Val Val
                100                 105                 110

Ala Thr Phe Asn Glu Lys Val Glu Ser Leu His Asn Val Asn Gly His
            115                 120                 125

Phe Ser Phe Gly Ile Lys Thr Leu Ile Thr Asn Ser Ser Gln Pro Asn
        130                 135                 140

Val Ile Glu Thr Asp Phe Gly Thr Ala Thr Ala Thr Gln Arg Leu Thr
145                 150                 155                 160

Ile Glu Gly Val Thr Asn Thr Glu Thr Gly Gln Ile Glu Arg Asp Tyr
                165                 170                 175

Pro Phe Phe Tyr Lys Val Gly Asp Leu Ala Gly Glu Ser Asn Gln Val
            180                 185                 190

Arg Trp Phe Leu Asn Val Asn Leu Asn Lys Ser Asp Val Thr Glu Asp
        195                 200                 205

Ile Ser Ile Ala Asp Arg Gln Gly Ser Gly Gln Gln Leu Asn Lys Glu
    210                 215                 220

Ser Phe Thr Phe Asp Ile Val Asn Asp Lys Glu Thr Lys Tyr Ile Ser
225                 230                 235                 240

Leu Ala Glu Phe Glu Gln Gln Gly Tyr Gly Lys Ile Asp Phe Val Thr
                245                 250                 255

Asp Asn Asp Phe Asn Leu Arg Phe Tyr Arg Asp Lys Ala Arg Phe Thr
            260                 265                 270

Ser Phe Ile Val Arg Tyr Thr Ser Thr Ile Thr Glu Ala Gly Gln His
        275                 280                 285

Gln Ala Thr Phe Glu Asn Ser Tyr Asp Ile Asn Tyr Gln Leu Asn Asn
    290                 295                 300

Gln Asp Ala Thr Asn Glu Lys Asn Thr Ser Gln Val Lys Asn Val Phe
305                 310                 315                 320

Val Glu Gly Glu Ala Ser Gly Asn Gln Asn Val Glu Met Pro Thr Glu
                325                 330                 335

Glu Ser Leu Asp Ile Pro Leu Glu Thr Ile Asp Glu Trp Glu Pro Lys
            340                 345                 350

Thr Pro Thr Ser Glu Gln Ala Thr Glu Thr Ser Glu Lys Thr Asp Thr
        355                 360                 365

Thr Glu Thr Ala Glu Ser Ser Gln Pro Glu Val His Val Ser Pro Thr
    370                 375                 380

Glu Glu Glu Asn Pro Asp Glu Gly Glu Thr Leu Gly Thr Ile Glu Pro
385                 390                 395                 400

Ile Ile Pro Glu Lys Pro Ser Val Thr Thr Glu Glu Asn Gly Thr Thr
                405                 410                 415

Glu Thr Ala Glu Ser Ser Gln Pro Glu Val His Val Ser Pro Thr Glu
            420                 425                 430

Glu Glu Asn Pro Asp Glu Ser Glu Thr Leu Gly Thr Ile Glu Pro Ile
        435                 440                 445

Ile Pro Glu Lys Pro Ser Val Thr Thr Glu Glu Asn Gly Thr Thr Glu
    450                 455                 460

Thr Ala Glu Ser Ser Gln Pro Glu Val His Val Ser Pro Ala Glu Glu
465                 470                 475                 480

Glu Asn Pro Asp Glu Ser Glu Thr Leu Gly Thr Ile Leu Pro Ile Leu
                485                 490                 495

Pro Glu Lys Pro Ser Val Thr Thr Glu Glu Asn Gly Thr Thr Glu Thr
            500                 505                 510
```

```
Ala Glu Ser Ser Gln Pro Glu Val His Val Ser Pro Thr Glu Glu Glu
        515                 520                 525

Asn Pro Asp Glu Ser Glu Thr Leu Gly Thr Ile Ala Pro Ile Ile Pro
    530                 535                 540

Glu Lys Pro Ser Val Thr Thr Glu Glu Asn Gly Ile Thr Glu Thr Ala
545                 550                 555                 560

Glu Ser Ser Gln Pro Glu Val His Val Ser Pro Thr Lys Glu Ile Thr
                565                 570                 575

Thr Thr Glu Lys Lys Gln Pro Ser Thr Glu Thr Thr Val Glu Lys Asn
        580                 585                 590

Lys Asn Val Thr Ser Lys Asn Gln Pro Gln Ile Leu Asn Ala Pro Leu
    595                 600                 605

Asn Thr Leu Lys Asn Glu Gly Ser Pro Gln Leu Ala Pro Gln Leu Leu
610                 615                 620

Ser Glu Pro Ile Gln Lys Leu Asn Glu Ala Asn Gly Gln Arg Glu Leu
625                 630                 635                 640

Pro Lys Thr Gly Thr Thr Lys Thr Pro Phe Met Leu Ile Ala Gly Ile
                645                 650                 655

Leu Ala Ser Thr Phe Ala Val Leu Gly Val Ser Tyr Leu Gln Ile Arg
        660                 665                 670

Lys Asn

<210> SEQ ID NO 4
<211> LENGTH: 2025
<212> TYPE: DNA
<213> ORGANISM: Enterococcus faecalis

<400> SEQUENCE: 4
atgacaaaaa gtgtaaaatt tttagtgtta ctgttggtaa tgattctacc aattgcgggg      60
gcgttattga ttggtccaat ttcgtttggc gccgaattga gcaaaagttc aatcgttgac     120
aaagtagaat tagatcacac tactttatat caaggagaga tgacctcaat taaagtatct     180
tttagtgaca agaaaaatca gaaaataaaa cctggagata ctattacttt aactttacca     240
gacgcactag ttggaatgac cgagaacgat agttcaccac gaaaaatcaa tttaaatggt     300
ttaggggaag ttttatcta aaagatcat gttgtagcaa catttaacga aaaagttgaa     360
tctttacata atgtgaatgg gcatttttct ttcgggatta aaacgcttat caccaatagt     420
tctcaaccga atgtgataga acggatttc ggaacagcaa cggcgactca acgtttgacg     480
attgaaggag tgactaacac agagactggc caaattgagc gagactatcc gtttttttat     540
aaagtaggcg atttggctgg agagtcaaat caagtacgtt ggttttttaaa tgtgaacctc     600 aataaatccg atgtcacaga agatatttca attgcggatc gacaaggaag tggtcaacaa     660
ttaaataaag agagttttac atttgatatt gtgaatgaca agaaactaa atatatttca     720 cttgccgagt tgagcaaca aggttatggc aaaattgact cgtaacaga taatgacttt     780 aacttacgtt tttatcggga taaagcacgc tttacttcct ttatcgtccg ttacacttcg     840
acaatcacag aagcaggcca acatcaagca acatttgaaa atagttatga catcaattat     900
caactaaaca atcaagacgc aacgaatgaa aaaaatacat cacaggttaa aaatgttttt     960
gtagaaggcg aggcaagcgg caatcaaaat gtggaaatgc aacagaagaa aagtctagac    1020 attccttag agacaataga tgaatgggaa ccaaagacac tacttcgga acaggcaaca    1080 gaaacaagtg aaaagacaga cacaacagaa accgcagaaa gcagccaacc agaagttcat    1140
```

```
gtctcaccaa cagaagaaga aaatccagat gaaggtgaaa cactaggcac gattgagcca    1200
atcatacctg aaaaaccaag tgtgacaact gaagagaatg gcacgacaga aactgcagaa    1260
agcagccaac cagaagttca tgtctcacca acagaagaag aaaatccaga tgaaagtgaa    1320
acactaggca cgattgagcc aatcatacct gaaaaaccaa gtgtgacaac tgaagagaac    1380
ggcacaacag aaaccgcaga aagcagccaa ccagaagttc atgtctcacc agcggaagaa    1440
gaaaatccag atgaaagtga aacgttaggt acaattttac caatcctacc tgaaaaacca    1500
agtgtgacaa ctgaagagaa tggcacaacg gaaactgcag aaagcagtca accagaagtc    1560
catgtgtcgc caacggaaga agaaaatcca gatgaaagtg aaacactagg cacgattgca    1620
ccaatcatac ctgaaaaacc aagcgtaaca actgaagaga atggtataac ggaaacggca    1680
gaaagcagcc agccagaagt tcatgtctca ccaacaaaag aaattactac aactgagaaa    1740
aaacagccat ccacagaaac aactgtggag aaaaataaaa atgttacatc aaaaaatcaa    1800
ccacaaatac taaacgctcc attaaataca ttgaaaaatg aaggaagccc acagttggct    1860
ccccaactgc ttagtgaacc aattcaaaaa ttaaatgaag caaacgggca acgagaactt    1920
cccaaaacag gcacaacaaa aacaccgttt atgctaatag caggaatact ggcaagtaca    1980
tttgccgttt taggtgtaag ttatctacaa atcagaaaga attaa                    2025
```

<210> SEQ ID NO 5  
<211> LENGTH: 303  
<212> TYPE: PRT  
<213> ORGANISM: Staphylococcus aureus

<400> SEQUENCE: 5

```
Gly Ser Ala Arg Asp Ile Ser Ser Thr Asn Val Thr Asp Leu Thr Val
1               5                   10                  15

Ser Pro Ser Lys Ile Glu Asp Gly Gly Lys Thr Thr Val Lys Met Thr
            20                  25                  30

Phe Asp Asp Lys Asn Gly Lys Ile Gln Asn Gly Asp Met Ile Lys Val
        35                  40                  45

Ala Trp Pro Thr Ser Gly Thr Val Lys Ile Glu Gly Tyr Ser Lys Thr
    50                  55                  60

Val Pro Leu Thr Val Lys Gly Glu Gln Val Gly Gln Ala Val Ile Thr
65                  70                  75                  80

Pro Asp Gly Ala Thr Ile Thr Phe Asn Asp Lys Val Glu Lys Leu Ser
                85                  90                  95

Asp Val Ser Gly Phe Ala Glu Phe Glu Val Gln Gly Arg Asn Leu Thr
            100                 105                 110

Gln Thr Asn Thr Ser Asp Asp Lys Val Ala Thr Ile Thr Ser Gly Asn
        115                 120                 125

Lys Ser Thr Asn Val Thr Val His Lys Ser Glu Ala Gly Thr Ser Ser
    130                 135                 140

Val Phe Tyr Tyr Lys Thr Gly Asp Met Leu Pro Glu Asp Thr Thr His
145                 150                 155                 160

Val Arg Trp Phe Leu Asn Ile Asn Asn Glu Lys Ser Tyr Val Ser Lys
                165                 170                 175

Asp Ile Thr Ile Lys Asp Gln Ile Gln Gly Gln Gln Leu Asp Leu
            180                 185                 190

Ser Thr Leu Asn Ile Asn Val Thr Gly Thr His Ser Asn Tyr Tyr Ser
        195                 200                 205

Gly Gln Ser Ala Ile Thr Asp Phe Glu Lys Ala Phe Pro Gly Ser Lys
    210                 215                 220
```

```
Ile Thr Val Asp Asn Thr Lys Asn Thr Ile Asp Val Thr Ile Pro Gln
225                 230                 235                 240

Gly Tyr Gly Ser Tyr Asn Ser Phe Ser Ile Asn Tyr Lys Thr Lys Ile
                245                 250                 255

Thr Asn Glu Gln Gln Lys Glu Phe Val Asn Asn Ser Gln Ala Trp Tyr
            260                 265                 270

Gln Glu His Gly Lys Glu Val Asn Gly Lys Ser Phe Asn His Thr
        275                 280                 285

Val His Asn Ile Asn Ala Asn Ala Gly Ile Glu Gly Thr Val Lys
    290                 295                 300

<210> SEQ ID NO 6
<211> LENGTH: 102
<212> TYPE: PRT
<213> ORGANISM: Streptococcus pyogenes

<400> SEQUENCE: 6

Met Thr Ile Glu Glu Asp Ser Ala Thr His Ile Lys Phe Ser Lys Arg
1               5                   10                  15

Asp Ile Asp Gly Lys Glu Leu Ala Gly Ala Thr Met Glu Leu Arg Asp
            20                  25                  30

Ser Ser Gly Lys Thr Ile Ser Thr Trp Ile Ser Asp Gly Gln Val Lys
        35                  40                  45

Asp Phe Tyr Leu Met Pro Gly Lys Tyr Thr Phe Val Glu Thr Ala Ala
    50                  55                  60

Pro Asp Gly Tyr Glu Val Ala Thr Ala Ile Thr Phe Thr Val Asn Glu
65                  70                  75                  80

Gln Gly Gln Val Thr Val Asn Gly Lys Ala Thr Lys Gly Asp Ala His
                85                  90                  95

Ile Val Met Val Asp Ala
            100

<210> SEQ ID NO 7
<211> LENGTH: 340
<212> TYPE: PRT
<213> ORGANISM: Streptococcus pyogenes

<400> SEQUENCE: 7

Met Lys Leu Arg His Leu Leu Leu Thr Gly Ala Ala Leu Thr Ser Phe
1               5                   10                  15

Ala Ala Thr Thr Val His Gly Glu Thr Val Val Asn Gly Ala Lys Leu
            20                  25                  30

Thr Val Thr Lys Asn Leu Asp Leu Val Asn Ser Asn Ala Leu Ile Pro
        35                  40                  45

Asn Thr Asp Phe Thr Phe Lys Ile Glu Pro Asp Thr Thr Val Asn Glu
    50                  55                  60

Asp Gly Asn Lys Phe Lys Gly Val Ala Leu Asn Thr Pro Met Thr Lys
65                  70                  75                  80

Val Thr Tyr Thr Asn Ser Asp Lys Gly Gly Ser Asn Thr Lys Thr Ala
                85                  90                  95

Glu Phe Asp Phe Ser Glu Val Thr Phe Glu Lys Pro Gly Val Tyr Tyr
            100                 105                 110

Tyr Lys Val Thr Glu Glu Lys Ile Asp Lys Val Pro Gly Val Ser Tyr
        115                 120                 125

Asp Thr Thr Ser Tyr Thr Val Gln Val His Val Leu Trp Asn Glu Glu
    130                 135                 140
```

Gln Gln Lys Pro Val Ala Thr Tyr Ile Val Gly Tyr Lys Glu Gly Ser
145                 150                 155                 160

Lys Val Pro Ile Gln Phe Lys Asn Ser Leu Asp Ser Thr Thr Leu Thr
                165                 170                 175

Val Lys Lys Val Ser Gly Thr Gly Gly Asp Arg Ser Lys Asp Phe
            180                 185                 190

Asn Phe Gly Leu Thr Leu Lys Ala Asn Gln Tyr Tyr Lys Ala Ser Glu
            195                 200                 205

Lys Val Met Ile Glu Lys Thr Thr Lys Gly Gly Gln Ala Pro Val Gln
            210                 215                 220

Thr Glu Ala Ser Ile Asp Gln Leu Tyr His Phe Thr Leu Lys Asp Gly
225                 230                 235                 240

Glu Ser Ile Lys Val Thr Asn Leu Pro Val Gly Val Asp Tyr Val Val
                245                 250                 255

Thr Glu Asp Asp Tyr Lys Ser Glu Lys Tyr Thr Thr Asn Val Glu Val
            260                 265                 270

Ser Pro Gln Asp Gly Ala Val Lys Asn Ile Ala Gly Asn Ser Thr Glu
            275                 280                 285

Gln Glu Thr Ser Thr Asp Lys Asp Met Thr Ile Thr Phe Thr Asn Lys
290                 295                 300

Lys Asp Phe Glu Val Pro Thr Gly Val Ala Met Thr Val Ala Pro Tyr
305                 310                 315                 320

Ile Ala Leu Gly Ile Val Ala Val Gly Gly Ala Leu Tyr Phe Val Lys
                325                 330                 335

Lys Lys Asn Ala
            340

<210> SEQ ID NO 8
<211> LENGTH: 1023
<212> TYPE: DNA
<213> ORGANISM: Streptococcus pyogenes

<400> SEQUENCE: 8
atgaaattac gtcacttact attaacggga gcagccctaa ctagttttgc tgctacaaca      60
gttcacgggg agactgttgt aaacggagcc aaactaacag ttacaaaaaa ccttgattta     120
gttaatagca atgcattaat tccaaataca gattttacat ttaaaatcga acctgatact     180
actgtcaacg aagacggaaa taagtttaaa ggtgtagctt gaacacacc gatgactaaa     240 gtcacttaca ccaattcaga taaggtgga tcaaatacga aaactgcaga atttgatttt     300
tcagaagtta cttttgaaaa accaggtgtt tattattaca agtaactga ggagaagata     360 gataaagttc ctggtgtttc ttatgataca acatcttaca ctgttcaagt tcatgtcttg     420
tggaatgaag agcaacaaaa accagtagct acttatattg ttggttataa agaaggtagt     480
aaggtgccaa ttcagttcaa aaatagctta gattctacta cattaacggt gaagaaaaaa     540
gtttcaggta ccggtggaga tcgctctaaa gattttaatt ttggtctgac tttaaaagca     600
aatcagtatt ataaggcgtc agaaaaagtc atgattgaga agacaactaa aggtggtcaa     660
gctcctgttc aaacagaggc tagtatagat caactctatc attttacctt gaaagatggt     720
gaatcaatca agtcacaaa tcttccagta ggtgtggatt atgttgtcac tgaagacgat     780
tacaaatcag aaaatatac aaccaacgtg aagttagtc ctcaagatgg agctgtaaaa     840
aatatcgcag gtaattcaac tgaacaagag acatctactg ataaagatat gaccattact     900
tttacaaata aaaaagactt tgaagtgcca acaggagtag caatgactgt ggcaccatat     960

```
attgctttag gaattgtagc agttggtgga gctctttact ttgttaaaaa gaaaaatgct   1020
taa                                                                1023
```

<210> SEQ ID NO 9
<211> LENGTH: 674
<212> TYPE: PRT
<213> ORGANISM: Enterococcus faecalis

<400> SEQUENCE: 9

| | | | | | | | | | | | | | | |
|---|---|---|---|---|---|---|---|---|---|---|---|---|---|---|
| Met | Thr | Lys | Ser | Val | Lys | Phe | Leu | Val | Leu | Leu | Val | Met | Ile | Leu |
| 1 | | | | 5 | | | | | 10 | | | | | 15 |
| Pro | Ile | Ala | Gly | Ala | Leu | Leu | Ile | Gly | Pro | Ile | Ser | Phe | Gly | Ala | Glu |
| | | | 20 | | | | | 25 | | | | | 30 | | |
| Leu | Ser | Lys | Ser | Ser | Ile | Val | Asp | Lys | Val | Glu | Leu | Asp | His | Thr | Thr |
| | | 35 | | | | | 40 | | | | | 45 | | | |
| Leu | Tyr | Gln | Gly | Glu | Met | Thr | Ser | Ile | Lys | Val | Ser | Phe | Ser | Asp | Lys |
| | 50 | | | | | 55 | | | | | 60 | | | | |
| Glu | Asn | Gln | Lys | Ile | Lys | Pro | Gly | Asp | Thr | Ile | Thr | Leu | Thr | Leu | Pro |
| 65 | | | | | 70 | | | | | 75 | | | | | 80 |
| Asp | Ala | Leu | Val | Gly | Met | Thr | Glu | Asn | Asp | Ser | Ser | Pro | Arg | Lys | Ile |
| | | | | 85 | | | | | 90 | | | | | 95 | |
| Asn | Leu | Asn | Gly | Leu | Gly | Glu | Val | Phe | Ile | Tyr | Lys | Asp | His | Val | Val |
| | | | 100 | | | | | 105 | | | | | 110 | | |
| Ala | Thr | Phe | Asn | Glu | Lys | Val | Glu | Ser | Leu | His | Asn | Val | Asn | Gly | His |
| | | 115 | | | | | 120 | | | | | 125 | | | |
| Phe | Ser | Phe | Gly | Ile | Lys | Thr | Leu | Ile | Thr | Asn | Ser | Ser | Gln | Pro | Asn |
| | 130 | | | | | 135 | | | | | 140 | | | | |
| Val | Ile | Glu | Thr | Asp | Phe | Gly | Thr | Ala | Thr | Ala | Thr | Gln | Arg | Leu | Thr |
| 145 | | | | | 150 | | | | | 155 | | | | | 160 |
| Ile | Glu | Gly | Val | Thr | Asn | Thr | Glu | Thr | Gly | Gln | Ile | Glu | Arg | Asp | Tyr |
| | | | | 165 | | | | | 170 | | | | | 175 | |
| Pro | Phe | Phe | Tyr | Lys | Val | Gly | Asp | Leu | Ala | Gly | Glu | Ser | Asn | Gln | Val |
| | | | 180 | | | | | 185 | | | | | 190 | | |
| Arg | Trp | Phe | Leu | Asn | Val | Asn | Leu | Asn | Lys | Ser | Asp | Val | Thr | Glu | Asp |
| | | | 195 | | | | | 200 | | | | | 205 | | |
| Ile | Ser | Ile | Ala | Asp | Arg | Gln | Gly | Ser | Gly | Gln | Gln | Leu | Asn | Lys | Glu |
| | | 210 | | | | | 215 | | | | | 220 | | | |
| Ser | Phe | Thr | Phe | Asp | Ile | Val | Asn | Asp | Lys | Glu | Thr | Lys | Tyr | Ile | Ser |
| 225 | | | | | 230 | | | | | 235 | | | | | 240 |
| Leu | Ala | Glu | Phe | Glu | Gln | Gln | Gly | Tyr | Gly | Lys | Ile | Asp | Phe | Val | Thr |
| | | | | 245 | | | | | 250 | | | | | 255 | |
| Asp | Asn | Asp | Phe | Asn | Leu | Arg | Phe | Tyr | Arg | Asp | Lys | Ala | Arg | Phe | Thr |
| | | | 260 | | | | | 265 | | | | | 270 | | |
| Ser | Phe | Ile | Val | Arg | Tyr | Thr | Ser | Thr | Ile | Thr | Glu | Ala | Gly | Gln | His |
| | | 275 | | | | | 280 | | | | | 285 | | | |
| Gln | Ala | Thr | Phe | Glu | Asn | Ser | Tyr | Asp | Ile | Asn | Tyr | Gln | Leu | Asn | Asn |
| | 290 | | | | | 295 | | | | | 300 | | | | |
| Gln | Asp | Ala | Thr | Asn | Glu | Lys | Asn | Thr | Ser | Gln | Val | Lys | Asn | Val | Phe |
| 305 | | | | | 310 | | | | | 315 | | | | | 320 |
| Val | Glu | Gly | Glu | Ala | Ser | Gly | Asn | Gln | Asn | Val | Glu | Met | Pro | Thr | Glu |
| | | | | 325 | | | | | 330 | | | | | 335 | |
| Glu | Ser | Leu | Asp | Ile | Pro | Leu | Glu | Thr | Ile | Asp | Glu | Trp | Glu | Pro | Lys |
| | | | 340 | | | | | 345 | | | | | 350 | | |

-continued

Thr Pro Thr Ser Glu Gln Ala Thr Glu Thr Ser Lys Thr Asp Thr
        355                 360                 365

Thr Glu Thr Ala Glu Ser Ser Gln Pro Glu Val His Val Ser Pro Thr
        370                 375                 380

Glu Glu Glu Asn Pro Asp Glu Gly Thr Leu Gly Thr Ile Glu Pro
385                 390                 395                 400

Ile Ile Pro Glu Lys Pro Ser Val Thr Thr Glu Glu Asn Gly Thr Thr
                405                 410                 415

Glu Thr Ala Glu Ser Ser Gln Pro Glu Val His Val Ser Pro Thr Glu
            420                 425                 430

Glu Glu Asn Pro Asp Glu Ser Glu Thr Leu Gly Thr Ile Glu Pro Ile
        435                 440                 445

Ile Pro Glu Lys Pro Ser Val Thr Thr Glu Glu Asn Gly Thr Thr Glu
    450                 455                 460

Thr Ala Glu Ser Ser Gln Pro Glu Val His Val Ser Pro Ala Glu Glu
465                 470                 475                 480

Glu Asn Pro Asp Glu Ser Glu Thr Leu Gly Thr Ile Leu Pro Ile Leu
                485                 490                 495

Pro Glu Lys Pro Ser Val Thr Thr Glu Glu Asn Gly Thr Thr Glu Thr
            500                 505                 510

Ala Glu Ser Ser Gln Pro Glu Val His Val Ser Pro Thr Glu Glu Glu
        515                 520                 525

Asn Pro Asp Glu Ser Glu Thr Leu Gly Thr Ile Ala Pro Ile Ile Pro
    530                 535                 540

Glu Lys Pro Ser Val Thr Thr Glu Glu Asn Gly Ile Thr Glu Thr Ala
545                 550                 555                 560

Glu Ser Ser Gln Pro Glu Val His Val Ser Pro Thr Lys Glu Ile Thr
                565                 570                 575

Thr Thr Glu Lys Lys Gln Pro Ser Thr Glu Thr Thr Val Glu Lys Asn
            580                 585                 590

Lys Asn Val Thr Ser Lys Asn Gln Pro Gln Ile Leu Asn Ala Pro Leu
        595                 600                 605

Asn Thr Leu Lys Asn Glu Gly Ser Pro Gln Leu Ala Pro Gln Leu Leu
    610                 615                 620

Ser Glu Pro Ile Gln Lys Leu Asn Glu Ala Asn Gly Gln Arg Glu Leu
625                 630                 635                 640

Pro Lys Thr Gly Thr Thr Lys Thr Pro Phe Met Leu Ile Ala Gly Ile
                645                 650                 655

Leu Ala Ser Thr Phe Ala Val Leu Gly Val Ser Tyr Leu Gln Ile Arg
            660                 665                 670

Lys Asn

<210> SEQ ID NO 10
<211> LENGTH: 331
<212> TYPE: PRT
<213> ORGANISM: Staphylococcus aureus

<400> SEQUENCE: 10

Met Asn Lys Asn Val Leu Lys Phe Met Val Phe Ile Met Leu Leu Asn
1               5                   10                  15

Ile Ile Thr Pro Leu Phe Asn Lys Asn Glu Ala Phe Ala Ala Arg Asp
            20                  25                  30

Ile Ser Ser Thr Asn Val Thr Asp Leu Thr Val Ser Pro Ser Lys Ile
        35                  40                  45

Glu Asp Gly Gly Lys Thr Thr Val Lys Met Thr Phe Asp Asp Lys Asn
 50                  55                  60

Gly Lys Ile Gln Asn Gly Asp Met Ile Lys Val Ala Trp Pro Thr Ser
 65                  70                  75                  80

Gly Thr Val Lys Ile Glu Gly Tyr Ser Lys Thr Val Pro Leu Thr Val
                 85                  90                  95

Lys Gly Glu Gln Val Gly Gln Ala Val Ile Thr Pro Asp Gly Ala Thr
            100                 105                 110

Ile Thr Phe Asn Asp Lys Val Glu Lys Leu Ser Asp Val Ser Gly Phe
        115                 120                 125

Ala Glu Phe Glu Val Gln Gly Arg Asn Leu Thr Gln Thr Asn Thr Ser
130                 135                 140

Asp Asp Lys Val Ala Thr Ile Thr Ser Gly Asn Lys Ser Thr Asn Val
145                 150                 155                 160

Thr Val His Lys Ser Glu Ala Gly Thr Ser Ser Val Phe Tyr Tyr Lys
                165                 170                 175

Thr Gly Asp Met Leu Pro Glu Asp Thr Thr His Val Arg Trp Phe Leu
            180                 185                 190

Asn Ile Asn Asn Glu Lys Ser Tyr Val Ser Lys Asp Ile Thr Ile Lys
        195                 200                 205

Asp Gln Ile Gln Gly Gly Gln Gln Leu Asp Leu Ser Thr Leu Asn Ile
210                 215                 220

Asn Val Thr Gly Thr His Ser Asn Tyr Tyr Ser Gly Gln Ser Ala Ile
225                 230                 235                 240

Thr Asp Phe Glu Lys Ala Phe Pro Gly Ser Lys Ile Thr Val Asp Asn
                245                 250                 255

Thr Lys Asn Thr Ile Asp Val Thr Ile Pro Gln Gly Tyr Gly Ser Tyr
            260                 265                 270

Asn Ser Phe Ser Ile Asn Tyr Lys Thr Lys Ile Thr Asn Glu Gln Gln
        275                 280                 285

Lys Glu Phe Val Asn Asn Ser Gln Ala Trp Tyr Gln Glu His Gly Lys
290                 295                 300

Glu Glu Val Asn Gly Lys Ser Phe Asn His Thr Val His Asn Ile Asn
305                 310                 315                 320

Ala Asn Ala Gly Ile Glu Gly Thr Val Lys Gly
                325                 330

<210> SEQ ID NO 11
<211> LENGTH: 102
<212> TYPE: PRT
<213> ORGANISM: Streptococcus pyogenes

<400> SEQUENCE: 11

Met Thr Ile Glu Glu Asp Ser Ala Thr His Ile Lys Phe Ser Lys Arg
1               5                   10                  15

Asp Ile Asp Gly Lys Glu Leu Ala Gly Ala Thr Met Glu Leu Arg Asp
            20                  25                  30

Ser Ser Gly Lys Thr Ile Ser Thr Trp Ile Ser Asp Gly Gln Val Lys
        35                  40                  45

Asp Phe Tyr Leu Met Pro Gly Lys Tyr Thr Phe Val Glu Thr Ala Ala
    50                  55                  60

Pro Asp Gly Tyr Glu Val Ala Thr Ala Ile Thr Phe Thr Val Asn Glu
65                  70                  75                  80

Gln Gly Gln Val Thr Val Asn Gly Lys Ala Thr Lys Gly Asp Ala His
                85                  90                  95

Ile Val Met Val Asp Ala
            100

<210> SEQ ID NO 12
<211> LENGTH: 309
<212> TYPE: DNA
<213> ORGANISM: Streptococcus pyogenes

<400> SEQUENCE: 12

```
atgacaattg aagaagatag tgctacccat attaaattct caaaacgtga tattgacggc    60
aaagagttag ctggtgcaac tatggagttg cgtgattcat ctggtaaaac tattagtaca   120
tggatttcag atggacaagt gaaagatttc tacctgatgc aggaaaaata catttgtc    180
gaaaccgcag caccagacgg ttatgaggta gcaactgcta ttacctttac agttaatgag   240
caaggtcagg ttactgtaaa tggcaaagca actaaaggtg acgctcatat tgtcatggtt   300
gatgcttga                                                            309
```

<210> SEQ ID NO 13
<211> LENGTH: 893
<212> TYPE: PRT
<213> ORGANISM: Streptococcus pneumoniae

<400> SEQUENCE: 13

Met Leu Asn Arg Glu Thr His Met Lys Lys Val Arg Lys Ile Phe Gln
1               5                   10                  15

Lys Ala Val Ala Gly Leu Cys Cys Ile Ser Gln Leu Thr Ala Phe Ser
            20                  25                  30

Ser Ile Val Ala Leu Ala Glu Thr Pro Glu Thr Ser Pro Ala Ile Gly
        35                  40                  45

Lys Val Val Ile Lys Glu Thr Gly Glu Gly Gly Ala Leu Leu Gly Asp
    50                  55                  60

Ala Val Phe Glu Leu Lys Asn Asn Thr Asp Gly Thr Thr Val Ser Gln
65                  70                  75                  80

Arg Thr Glu Ala Gln Thr Gly Glu Ala Ile Phe Ser Asn Ile Lys Pro
                85                  90                  95

Gly Thr Tyr Thr Leu Thr Glu Ala Gln Pro Pro Val Gly Tyr Lys Pro
            100                 105                 110

Ser Thr Lys Gln Trp Thr Val Glu Val Glu Lys Asn Gly Arg Thr Thr
        115                 120                 125

Val Gln Gly Glu Gln Val Glu Asn Arg Glu Glu Ala Leu Ser Asp Gln
    130                 135                 140

Tyr Pro Gln Thr Gly Thr Tyr Pro Asp Val Gln Thr Pro Tyr Gln Ile
145                 150                 155                 160

Ile Lys Val Asp Gly Ser Glu Lys Asn Gly Gln His Lys Ala Leu Asn
                165                 170                 175

Pro Asn Pro Tyr Glu Arg Val Ile Pro Glu Gly Thr Leu Ser Lys Arg
            180                 185                 190

Ile Tyr Gln Val Asn Asn Leu Asp Asp Asn Gln Tyr Gly Ile Glu Leu
        195                 200                 205

Thr Val Ser Gly Lys Thr Val Tyr Glu Gln Lys Asp Lys Ser Val Pro
    210                 215                 220

Leu Asp Val Val Ile Leu Leu Asp Asn Ser Asn Ser Met Ser Asn Ile
225                 230                 235                 240

Arg Asn Lys Asn Ala Arg Arg Ala Glu Arg Ala Gly Glu Ala Thr Arg
                245                 250                 255

```
Ser Leu Ile Asp Lys Ile Thr Ser Asp Ser Glu Asn Arg Val Ala Leu
            260                 265                 270

Val Thr Tyr Ala Ser Thr Ile Phe Asp Gly Thr Glu Phe Thr Val Glu
        275                 280                 285

Lys Gly Val Ala Asp Lys Asn Gly Lys Arg Leu Asn Asp Ser Leu Phe
    290                 295                 300

Trp Asn Tyr Asp Gln Thr Ser Phe Thr Asn Thr Lys Asp Tyr Ser
305                 310                 315                 320

Tyr Leu Lys Leu Thr Asn Asp Lys Asn Asp Ile Val Glu Leu Lys Asn
                325                 330                 335

Lys Val Pro Thr Glu Ala Glu Asp His Asp Gly Asn Arg Leu Met Tyr
            340                 345                 350

Gln Phe Gly Ala Thr Phe Thr Gln Lys Ala Leu Met Lys Ala Asp Glu
        355                 360                 365

Ile Leu Thr Gln Gln Ala Arg Gln Asn Ser Gln Lys Val Ile Phe His
    370                 375                 380

Ile Thr Asp Gly Val Pro Thr Met Ser Tyr Pro Ile Asn Phe Asn His
385                 390                 395                 400

Ala Thr Phe Ala Pro Ser Tyr Gln Asn Gln Leu Asn Ala Phe Phe Ser
                405                 410                 415

Lys Ser Pro Asn Lys Asp Gly Ile Leu Leu Ser Asp Phe Ile Thr Gln
            420                 425                 430

Ala Thr Ser Gly Glu His Thr Ile Val Arg Gly Asp Gly Gln Ser Tyr
        435                 440                 445

Gln Met Phe Thr Asp Lys Thr Val Tyr Glu Lys Gly Ala Pro Ala Ala
    450                 455                 460

Phe Pro Val Lys Pro Glu Lys Tyr Ser Glu Met Lys Ala Ala Gly Tyr
465                 470                 475                 480

Ala Val Ile Gly Asp Pro Ile Asn Gly Gly Tyr Ile Trp Leu Asn Trp
                485                 490                 495

Arg Glu Ser Ile Leu Ala Tyr Pro Phe Asn Ser Asn Thr Ala Lys Ile
            500                 505                 510

Thr Asn His Gly Asp Pro Thr Arg Trp Tyr Tyr Asn Gly Asn Ile Ala
        515                 520                 525

Pro Asp Gly Tyr Asp Val Phe Thr Val Gly Ile Gly Ile Asn Gly Asp
    530                 535                 540

Pro Gly Thr Asp Glu Ala Thr Ala Thr Ser Phe Met Gln Ser Ile Ser
545                 550                 555                 560

Ser Lys Pro Glu Asn Tyr Thr Asn Val Thr Asp Thr Thr Lys Ile Leu
                565                 570                 575

Glu Gln Leu Asn Arg Tyr Phe His Thr Ile Val Thr Gly Lys Lys Ser
            580                 585                 590

Ile Glu Asn Gly Thr Ile Thr Asp Pro Met Gly Glu Leu Ile Asp Leu
        595                 600                 605

Gln Leu Gly Thr Asp Gly Arg Phe Asp Pro Ala Asp Tyr Thr Leu Thr
    610                 615                 620

Ala Asn Asp Gly Ser Arg Leu Glu Asn Gly Gln Ala Val Gly Gly Pro
625                 630                 635                 640

Gln Asn Asp Gly Gly Leu Leu Lys Asn Ala Lys Val Leu Tyr Asp Thr
                645                 650                 655

Thr Glu Lys Arg Ile Arg Val Thr Gly Leu Tyr Leu Gly Thr Asp Glu
            660                 665                 670
```

```
Lys Val Thr Leu Thr Tyr Asn Val Arg Leu Asn Asp Glu Phe Val Ser
            675                 680                 685

Asn Lys Phe Tyr Asp Thr Asn Gly Arg Thr Thr Leu His Pro Lys Glu
        690                 695                 700

Val Glu Gln Asn Thr Val Arg Asp Phe Pro Ile Pro Lys Ile Arg Asp
705                 710                 715                 720

Val Arg Lys Tyr Pro Glu Ile Thr Ile Ser Lys Glu Lys Lys Leu Gly
                725                 730                 735

Asp Ile Glu Phe Ile Lys Val Asn Lys Asn Asp Lys Lys Pro Leu Arg
            740                 745                 750

Gly Ala Val Phe Ser Leu Gln Lys Gln His Pro Asp Tyr Pro Asp Ile
        755                 760                 765

Tyr Gly Ala Ile Asp Gln Asn Gly Thr Tyr Gln Asn Val Arg Thr Gly
    770                 775                 780

Glu Asp Gly Lys Leu Thr Phe Lys Asn Leu Ser Asp Gly Lys Tyr Arg
785                 790                 795                 800

Leu Phe Glu Asn Ser Glu Pro Ala Gly Tyr Lys Pro Val Gln Asn Lys
                805                 810                 815

Pro Ile Val Ala Phe Gln Ile Val Asn Gly Glu Val Arg Asp Val Thr
            820                 825                 830

Ser Ile Val Pro Gln Asp Ile Pro Ala Gly Tyr Glu Phe Thr Asn Asp
        835                 840                 845

Lys His Tyr Ile Thr Asn Glu Pro Ile Pro Pro Lys Arg Glu Tyr Pro
    850                 855                 860

Arg Thr Gly Gly Ile Gly Met Leu Pro Phe Tyr Leu Ile Gly Cys Met
865                 870                 875                 880

Met Met Gly Gly Val Leu Leu Tyr Thr Arg Lys His Pro
                885                 890
```

<210> SEQ ID NO 14
<211> LENGTH: 2682
<212> TYPE: DNA
<213> ORGANISM: Streptococcus pneumoniae

<400> SEQUENCE: 14

```
atgctgaacc gcgaaaccca tatgaaaaaa gtaagaaaga tatttcagaa ggcagttgca      60
ggactgtgct gtatatctca gttgacagct ttttcttcga tagttgcttt agcagaaacg     120
cctgaaacca gtccagcgat aggaaaagta gtgattaagg agacaggcga aggaggagcg     180
cttctaggag atgccgtctt tgagttgaaa acaatacgg atggcacaac tgtttcgcaa      240
aggacagagg cgcaaacagg agaagcgata ttttcaaaca taaaacctgg acatacacc      300
ttgacagaag cccaacctcc agttggttat aaaccctcta ctaaacaatg gactgttgaa     360
gttgagaaga atggtcggac gactgtccaa ggtgaacagg tagaaaatcg agaagaggct     420
ctatctgacc agtatccaca aacagggact tatccagatg ttcaaacacc ttatcagatt     480
attaaggtag atggttcgga aaaaaacgga cagcacaagg cgttgaatcc gaatccatat     540
gaacgtgtga ttccagaagg tacactttca agagaattt atcaagtgaa taatttggat     600
gataaccaat atggaatcga attgacggtt agtgggaaaa cagtgtatga acaaaaagat     660
aagtctgtgc cgctggatgt cgttatcttg ctcgataact caaatagtat gagtaacatt     720
cgaaacaaga atgctcgacg tgcggaaaga gctggtgagg cgacacgttc tcttattgat     780
aaaattacat ctgattcaga aaataggta gcgcttgtga cttatgcttc cactatcttt     840
gatgggaccg agtttacagt agaaaaaggg gtagcagata aaaacggaaa gcgattgaat     900
```

-continued

```
gattctcttt tttggaatta tgatcagacg agttttacaa ccaataccaa agattatagt    960
tatttaaagc tgactaatga taagaatgac attgtagaat taaaaaataa ggtacctacc   1020
gaggcagaag accatgatgg aaatagattg atgtaccaat tcggtgccac ttttactcag   1080
aaagctttga tgaaggcaga tgagattttg acacaacaag cgagacaaaa tagtcaaaaa   1140
gtcatttttcc atattacgga tggtgtccca actatgtcgt atccgattaa ttttaatcat   1200
gctacgtttg ctccatcata tcaaaatcaa ctaaatgcat tttttagtaa atctcctaat   1260
aaagatggaa tactattaag tgattttatt acgcaagcaa ctagtggaga acatacaatt   1320
gtacgcggag atgggcaaag ttaccagatg tttacagata agacagttta tgaaaaaggt   1380
gctcctgcag ctttcccagt taaacctgaa aaatattctg aaatgaaggc ggctggttat   1440
gcagttatag cgatccaat taatggtgga tatatttggc ttaattggag agagagtatt   1500
ctggcttatc cgtttaattc taatactgct aaaattacca atcatggtga ccctacaaga   1560
tggtactata cgggaatat tgctcctgat gggtatgatg tctttacggt aggtattggt   1620
attaacggag atcctggtac ggatgaagca acggctacta gttttatgca agtatttct   1680
agtaaacctg aaaactatac caatgttact gacacgacaa aaatattgga acagttgaat   1740
cgttatttcc acaccatcgt aactgaaaag aaatcaattg agaatggtac gattacagat   1800
ccgatgggtg agttaattga tttgcaattg ggcacagatg gaagatttga tccagcagat   1860
tacactttaa ctgcaaacga tggtagtcgc ttggagaatg acaagctgt aggtggtcca   1920
caaaatgatg tggtttgtt aaaaaatgca aagtgctct atgatacgac tgagaaaagg   1980
attcgtgtaa caggtctgta ccttggaacg gatgaaaaag ttacgttgac ctacaatgtt   2040
cgtttgaatg atgagtttgt aagcaataaa ttttatgata ccaatggtcg aacaacctta   2100
catcctaagg aagtagaaca gaacacagtg cgcgacttcc cgattcctaa gattcgtgat   2160
gtgcggaagt atccagaaat cacaatttca aaagagaaaa aacttggtga cattgagttt   2220
attaaggtca ataaaaatga taaaaaacca ctgagaggtg cggtctttag tcttcaaaaa   2280
caacatccgg attatccaga tatttatgga gctattgatc aaaatggcac ttatcaaaat   2340
gtgagaacag gtgaagatgg taagttgacc tttaaaaatc tgtcagatgg aaatatcga   2400
ttatttgaaa attctgaacc agctggttat aaacccgttc aaaataagcc tatcgttgcc   2460
ttccaaatag taaatggaga agtcagagat gtgacttcaa tcgttccaca agatatacca   2520
gcgggttacg agtttacgaa tgataagcac tatattacca atgaacctat tcctccaaag   2580
agagaatatc ctcgaactgg tggtatcgga atgttgccat tctatctgat aggttgcatg   2640
atgatgggag gagttctatt atacacacgg aaacatccgt aa                     2682
```

<210> SEQ ID NO 15
<211> LENGTH: 738
<212> TYPE: PRT
<213> ORGANISM: Streptococcus intermedius

<400> SEQUENCE: 15

```
Met Lys Lys Arg Arg Gly Gln Phe Phe Lys Ser Ala Ile Ser Phe Leu
1               5                   10                  15

Val Val Phe Leu Met Val Met Val Ser Ile Ile Tyr Pro Ser Ser Lys
            20                  25                  30

Ile Lys Ala Asp Gly Phe Pro Asn Asp Ala Thr Gly Val Ser Pro Asn
        35                  40                  45

Gly Lys Tyr Tyr Ser Ala Gly Arg Glu Asn Arg Leu Gly Met Val Thr
```

-continued

```
            50                  55                  60
Ser Asp Glu Leu His Thr Ala Thr Glu Leu Phe Gly Phe Cys Met Ala
 65                  70                  75                  80

Asn Ser Lys Lys Tyr Pro Gly Tyr Asp Ser Lys Asp Glu Tyr Phe
                 85                  90                  95

Gly Val Tyr Glu Gln Ile Leu Asn Leu Asn Lys Glu Ser Phe Asn Lys
                100                 105                 110

Leu Val Arg Asp Asn His Thr Tyr Gly Asn Ile Pro Thr Ser Pro Glu
                115                 120                 125

Glu Leu Trp Asp Lys Val Ser Lys Leu Ile Tyr Ile Tyr Leu Lys Asp
130                 135                 140

Pro Thr Asn Val Ile Gly Gln Ala Gly Trp Thr Asn Pro Gln Asp Ala
145                 150                 155                 160

Met Tyr Glu Phe Tyr Thr Val Val Gln Gln Glu Ile Trp Arg Tyr Thr
                165                 170                 175

Asp Gly Gln Lys Val Asp Lys Asp Thr Asn Ser Tyr Leu Tyr Tyr Lys
                180                 185                 190

Tyr Ser Lys Gln Gly Gln Lys Ala Val Tyr Leu Leu Arg Asp Ala Val
                195                 200                 205

Asn Ser Ile Ser Ile Pro Ser Asn Phe Glu Leu Arg Gly Tyr Lys Pro
                210                 215                 220

Glu Trp Val Gln Gly Gln Lys Gly Tyr Gln Ala Ile Val Thr Gly Arg
225                 230                 235                 240

Leu Lys Val Asp Gln Pro Val Gly Glu Ile Lys Thr Thr Val Thr Ala
                245                 250                 255

Gly Gly Lys Thr Ser Ser Glu Asn Asp Ile Ala Thr Leu Lys Ala Gln
                260                 265                 270

Asp Val Ile Gly Gly Val Glu Val Ser Asp Lys Ile Thr Tyr Ser Gly
                275                 280                 285

Leu Tyr Pro Asn Thr Glu Tyr Asp Val Ile Gly Glu Ile Tyr Glu Val
                290                 295                 300

Lys Asp Gly Glu Leu Val Asn Pro Gly Arg Pro Val Ser Val Val Asn
305                 310                 315                 320

Ser Gly Asp Asp Leu Lys Thr Asp Ala Thr Gly Lys Gly Lys Trp Thr
                325                 330                 335

Leu Asn Phe Gly Lys Leu Asp Leu Glu Ala Gly Lys Ser Tyr Val Val
                340                 345                 350

Phe Glu Lys Val Val Ser Leu Lys Asn Val Ile Asp Thr Asp Gly Asp
                355                 360                 365

Gly Lys Pro Asp Lys Lys Gln Glu Leu Ser His Asn Asp Pro Lys Asp
                370                 375                 380

Lys Ser Gln Thr Phe Thr Ile Leu Pro Lys Glu Ile Val Glu Gln Asp
385                 390                 395                 400

Val Val Phe Ser Lys Val Asn Val Ala Gly Glu Glu Ile Ala Gly Ala
                405                 410                 415

Lys Ile Gln Leu Lys Asp Ala Gln Gly Val Val His Ser Trp Thr
                420                 425                 430

Ser Lys Ala Gly Gln Ser Glu Thr Val Lys Leu Lys Ala Gly Thr Tyr
                435                 440                 445

Thr Phe His Glu Ala Ser Ala Pro Thr Gly Tyr Leu Ala Val Thr Asp
                450                 455                 460

Ile Thr Phe Glu Val Asp Val Gln Gly Lys Val Thr Val Lys Asp Ala
465                 470                 475                 480
```

Asn Gly Asn Gly Val Lys Ala Asp Gly Asn Lys Leu Thr Val Thr Asp
                485                 490                 495

Gln Ala Ala Pro Ser Val Pro Asn Glu Gln Asp Val Val Phe Ser Lys
            500                 505                 510

Val Asn Val Ala Gly Glu Glu Ile Ala Gly Ala Lys Ile Gln Leu Lys
        515                 520                 525

Asp Ala Gln Gly Gln Val Val His Ser Trp Thr Ser Lys Ala Gly Gln
    530                 535                 540

Ser Glu Thr Val Lys Leu Lys Ala Gly Thr Tyr Thr Phe His Glu Ala
545                 550                 555                 560

Ser Ala Pro Thr Gly Tyr Leu Ala Val Thr Asp Ile Thr Phe Glu Val
                565                 570                 575

Asp Val Gln Gly Lys Val Thr Val Lys Asp Ala Asn Gly Asn Gly Val
            580                 585                 590

Lys Ala Asp Gly Asn Lys Leu Thr Val Thr Asp Gln Ala Ala Pro Ser
        595                 600                 605

Val Pro Asn Glu Gln Asp Val Val Phe Ser Lys Val Asn Val Ala Gly
    610                 615                 620

Glu Glu Ile Ala Gly Ala Lys Ile Gln Leu Lys Asp Ala Gln Gly Gln
625                 630                 635                 640

Val Val His Ser Trp Thr Ser Lys Ala Gly Gln Ser Glu Thr Val Lys
                645                 650                 655

Leu Lys Ala Gly Thr Tyr Thr Phe His Glu Ala Ser Ala Pro Thr Gly
            660                 665                 670

Tyr Leu Ala Val Thr Asp Ile Thr Phe Glu Val Asp Val Gln Gly Lys
        675                 680                 685

Val Thr Val Lys Asp Ala Asn Gly Asn Gly Val Lys Ala Asp Gly Asn
    690                 695                 700

Lys Leu Thr Val Thr Asp Gln Ala Ala Pro Ser Val Pro Asn Glu Gln
705                 710                 715                 720

Asp Val Val Phe Ser Lys Val Asn Val Ala Gly Glu Glu Ile Ala Gly
                725                 730                 735

Ala Lys

<210> SEQ ID NO 16
<211> LENGTH: 2215
<212> TYPE: DNA
<213> ORGANISM: Streptococcus intermedius

<400> SEQUENCE: 16
atgaaaaaga gaagaggaca attttcaaa agtgcaattt cgttttggt tgtatttttg      60 atggtaatgg taagtatcat ttacccatct tcaaaaatta agcagatgg atttcctaat    120 gatgctacgg gagtatcgcc aaatggtaaa tattactcgg cagggagaga aaccgttta    180 ggaatggtta catcagatga attgcataca gctacagaat tattcggttt ttgtatggca    240
aatagcaaga aatatccagg atatgattca aaaaaggatg agtattttgg ggtgtatgaa    300
caaatcttaa accttaataa agaaagcttt aataagcttg ttagagataa tcatacgtat    360
ggtaacattc ctacaagtcc agaggaactt tgggataaag tatctaaact gatttatatt    420
tatttgaaag accctacaaa tgttattgga caagctgggt ggacgaatcc acaggatgca    480
atgtatgaat tttatactgt tgtacaacag gaaatatggc gttatacaga tggcaaaaag    540
gtggataaag acaccaattc atatttgtat tataaatatt caaaacaagg tcaaaaagca    600

```
gtgtacttac tgcgtgacgc tgtgaatagc atcagtatac ctagtaattt tgaacttcgt       660
ggctataaac ctgaatgggt tcaaggtcaa aaaggatacc aagctattgt aactggtaga       720
ttgaaagtag atcaacctgt cggggaaata aagactacag taacagcagg tggaaaaacc       780
tcaagtgaaa acgacattgc tacattgaag gcgcaagacg ttataggtgg ggttgaagtc       840
tctgataaga taacatatag tggtctttat ccaaatacag aatatgatgt tataggtgaa       900
atttacgaag taaagatgg agaacttgtt aatccaggac gaccggtttc tgtagtcaat        960
agtggtgacg atttaaaaac agatgcaaca ggaaaaggga atggacatt aaactttgga      1020 aagcttgatt tagaagcagg aaaatcctat gtggtctttg aaaagttgt ttcattaaaa       1080 aacgtgatag atacagatgg agatggaaaa ccggataaaa acaagaact atcgcataat      1140 gatccaaaag ataaatcgca aacatttaca attttaccta aggaaatagt tgaacaagac      1200
gttgtcttca gtaaggtgaa tgtggctggt gaagaaatcg ctggtgcgaa gatccaactg      1260
aaggatgcgc aaggtcaagt tgttcattcc tggacttcta aagcgggtca agtgaaacg       1320 gtcaaattga aagctggcac ctatactttc catgaagcat ccgctccgac tggttacttg      1380
gccgtaacgg atatcacatt cgaagtagat gttcaaggaa aagtgacggt taaggatgcc      1440
aacggcaatg tgttaaggc ggatggtaat aagttaacgg tgaccgatca agctgctcct      1500
agcgtaccga atgaacaaga cgttgtcttc agtaaggtga atgtggctgg tgaagaaatc      1560
gctggtgcga agatccaact gaaggatgcg caaggtcaag ttgttcattc ctggacttct      1620
aaagcgggtc aaagtgaaac ggtcaaattg aaagctggca cctatacttt ccatgaagca      1680
tccgctccga ctggttactt ggccgtaacg gatatcacat tcgaagtaga tgttcaagga      1740
aaagtgacgg ttaaggatgc caacggcaat ggtgttaagg cggatggtaa taagttaacg      1800
gtgaccgatc aagctgctcc tagcgtaccg aatgaacaag acgttgtctt cagtaaggtg      1860
aatgtggctg gtgaagaaat cgctggtgcg aagatccaac tgaaggatgc gcaaggtcaa      1920
gttgttcatt cctggacttc taaagcgggt caaagtgaaa cggtcaaatt gaaagctggc      1980
acctatactt tccatgaagc atccgctccg actggttact tggccgtaac ggatatcaca      2040
ttcgaagtag atgttcaagg aaaagtgacg gttaaggatg ccaacggcaa tggtgttaag      2100
gcggatggta ataagttaac ggtgaccgat caagctgctc tagcgtacc gaatgaacaa       2160 gacgttgtct tcagtaaggt gaatgtggct ggtgaagaaa tcgctggtgc gaaga           2215
```

<210> SEQ ID NO 17
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: X is any amino acid

<400> SEQUENCE: 17

Leu Pro Xaa Thr Gly
1               5

<210> SEQ ID NO 18
<211> LENGTH: 6
<212> TYPE: PRT
<213> ORGANISM: Artificial Sequence
<220> FEATURE:
<223> OTHER INFORMATION: synthetic

```
<400> SEQUENCE: 18

Leu Pro Thr Gly Ala Ala
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic

<400> SEQUENCE: 19

Leu Pro Thr Gly Gly Gly
1               5

<210> SEQ ID NO 20
<211> LENGTH: 6
<212> TYPE: PRT
<213> ORGANISM: Artificial Sequence
<220> FEATURE:
<223> OTHER INFORMATION: synthetic

<400> SEQUENCE: 20

Leu Pro Lys Thr Gly Gly
1               5

<210> SEQ ID NO 21
<211> LENGTH: 5
<212> TYPE: PRT
<213> ORGANISM: Artificial Sequence
<220> FEATURE:
<223> OTHER INFORMATION: synthetic

<400> SEQUENCE: 21

Leu Pro Glu Thr Gly
1               5

<210> SEQ ID NO 22
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: X is any amino acid

<400> SEQUENCE: 22

Leu Pro Xaa Thr Gly
1               5

<210> SEQ ID NO 23
<211> LENGTH: 6
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: X is any amino acid
<220> FEATURE:
<221> NAME/KEY: MISC_FEATURE
<222> LOCATION: (6)..(6)
<223> OTHER INFORMATION: X is any amino acid

<400> SEQUENCE: 23
```

Leu Pro Xaa Thr Gly Xaa
1               5

<210> SEQ ID NO 24
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (3)..(3)
<223> OTHER INFORMATION: X is glutamine or lysine
<220> FEATURE:
<221> NAME/KEY: MISC_FEATURE
<222> LOCATION: (5)..(5)
<223> OTHER INFORMATION: X is asparagine or glycine

<400> SEQUENCE: 24

Asn Pro Xaa Thr Xaa
1               5

<210> SEQ ID NO 25
<211> LENGTH: 40
<212> TYPE: PRT
<213> ORGANISM: Artificial Sequence
<220> FEATURE:
<223> OTHER INFORMATION: synthetic

<400> SEQUENCE: 25

Met Gly Ser Ser His His His His His His Ser Ser Gly Leu Val Pro
1               5                   10                  15

Arg Gly Ser Val Pro Thr Ile Val Met Val Asp Ala Tyr Lys Arg Tyr
            20                  25                  30

Lys Gly Ser Gly Glu Ser Gly Lys
        35                  40

<210> SEQ ID NO 26
<211> LENGTH: 139
<212> TYPE: PRT
<213> ORGANISM: Artificial Sequence
<220> FEATURE:
<223> OTHER INFORMATION: synthetic

<400> SEQUENCE: 26

Met Ser Tyr Tyr His His His His His His Asp Tyr Asp Ile Pro Thr
1               5                   10                  15

Thr Glu Asn Leu Tyr Phe Gln Gly Ala Met Val Thr Thr Leu Ser Gly
            20                  25                  30

Leu Ser Gly Glu Gln Gly Pro Ser Gly Asp Met Thr Thr Glu Glu Asp
        35                  40                  45

Ser Ala Thr His Ile Lys Phe Ser Lys Arg Asp Glu Asp Gly Arg Glu
    50                  55                  60

Leu Ala Gly Ala Thr Met Glu Leu Arg Asp Ser Ser Gly Lys Thr Ile
65                  70                  75                  80

Ser Thr Trp Ile Ser Asp Gly His Val Lys Asp Phe Tyr Leu Tyr Pro
                85                  90                  95

Gly Lys Tyr Thr Phe Val Glu Thr Ala Ala Pro Asp Gly Tyr Glu Val
            100                 105                 110

Ala Thr Ala Ile Thr Phe Thr Val Asn Glu Gln Gly Gln Val Thr Val
        115                 120                 125

Asn Gly Glu Ala Thr Lys Gly Asp Ala His Thr
    130                 135

<210> SEQ ID NO 27
<211> LENGTH: 15
<212> TYPE: PRT
<213> ORGANISM: Artificial Sequence
<220> FEATURE:
<223> OTHER INFORMATION: synthetic

<400> SEQUENCE: 27

Val Pro Thr Ile Val Met Val Asp Ala Tyr Lys Arg Tyr Lys Ser
1               5                   10                  15

<210> SEQ ID NO 28
<211> LENGTH: 119
<212> TYPE: PRT
<213> ORGANISM: Artificial Sequence
<220> FEATURE:
<223> OTHER INFORMATION: synthetic

<400> SEQUENCE: 28

Tyr Phe Gln Gly Ala Met Val Thr Thr Leu Ser Gly Leu Ser Gly Glu
1               5                   10                  15

Gln Gly Pro Ser Gly Asp Met Thr Thr Glu Glu Asp Ser Ala Thr His
            20                  25                  30

Ile Lys Phe Ser Lys Arg Asp Glu Asp Gly Arg Glu Leu Ala Gly Ala
        35                  40                  45

Thr Met Glu Leu Arg Asp Ser Ser Gly Lys Thr Ile Ser Thr Trp Ile
    50                  55                  60

Ser Asp Gly His Val Lys Asp Phe Tyr Leu Tyr Pro Gly Lys Tyr Thr
65                  70                  75                  80

Phe Val Glu Thr Ala Ala Pro Asp Gly Tyr Glu Val Ala Thr Ala Ile
                85                  90                  95

Thr Phe Thr Val Asn Glu Gln Gly Gln Val Thr Val Asn Gly Glu Ala
            100                 105                 110

Thr Lys Gly Asp Ala His Thr
        115

<210> SEQ ID NO 29
<211> LENGTH: 1689
<212> TYPE: DNA
<213> ORGANISM: Artificial Sequence
<220> FEATURE:
<223> OTHER INFORMATION: examplary SpyCatcher-pIII sequence
<220> FEATURE:
<221> NAME/KEY: CDS
<222> LOCATION: (1)..(1689)
<220> FEATURE:
<221> NAME/KEY: misc_feature
<222> LOCATION: (1)..(6)
<223> OTHER INFORMATION: EcoRI (2)
<220> FEATURE:
<221> NAME/KEY: misc_feature
<222> LOCATION: (7)..(63)
<223> OTHER INFORMATION: DsbA signal peptide
<220> FEATURE:
<221> NAME/KEY: misc_feature
<222> LOCATION: (64)..(411)
<223> OTHER INFORMATION: SpyCatcher
<220> FEATURE:
<221> NAME/KEY: misc_feature
<222> LOCATION: (412)..(432)
<223> OTHER INFORMATION: TEV cleavage site
<220> FEATURE:
<221> NAME/KEY: misc_feature
<222> LOCATION: (433)..(468)
<223> OTHER INFORMATION: Linker
<220> FEATURE:

```
<221> NAME/KEY: misc_feature
<222> LOCATION: (463)..(468)
<223> OTHER INFORMATION: Xba1
<220> FEATURE:
<221> NAME/KEY: misc_feature
<222> LOCATION: (469)..(1686)
<223> OTHER INFORMATION: gIII

<400> SEQUENCE: 29
```

| | | | | | | | | | | | | | | | | |
|---|---|---|---|---|---|---|---|---|---|---|---|---|---|---|---|---|
| gaa | ttc | atg | aag | aag | atc | tgg | tta | gcg | tta | gct | ggt | ctt | gtg | ttg | gcg | 48 |
| Glu | Phe | Met | Lys | Lys | Ile | Trp | Leu | Ala | Leu | Ala | Gly | Leu | Val | Leu | Ala | |
| 1 | | | | 5 | | | | | 10 | | | | | 15 | | |
| ttt | agt | gct | agt | gcc | ggg | gca | atg | gtg | gac | acg | ttg | tca | ggt | ctg | agc | 96 |
| Phe | Ser | Ala | Ser | Ala | Gly | Ala | Met | Val | Asp | Thr | Leu | Ser | Gly | Leu | Ser | |
| | | | 20 | | | | | 25 | | | | | 30 | | | |
| tca | gaa | cag | ggt | cag | tcg | ggt | gat | atg | acc | att | gag | gaa | gat | agc | gca | 144 |
| Ser | Glu | Gln | Gly | Gln | Ser | Gly | Asp | Met | Thr | Ile | Glu | Glu | Asp | Ser | Ala | |
| | 35 | | | | | 40 | | | | | 45 | | | | | |
| acc | cac | atc | aaa | ttt | agc | aag | cgc | gat | gaa | gat | ggc | aaa | gag | ctt | gcc | 192 |
| Thr | His | Ile | Lys | Phe | Ser | Lys | Arg | Asp | Glu | Asp | Gly | Lys | Glu | Leu | Ala | |
| | 50 | | | | 55 | | | | | 60 | | | | | | |
| ggc | gcg | aca | atg | gag | tta | cgg | gat | tct | tcc | ggc | aag | acc | att | agc | acc | 240 |
| Gly | Ala | Thr | Met | Glu | Leu | Arg | Asp | Ser | Ser | Gly | Lys | Thr | Ile | Ser | Thr | |
| 65 | | | | 70 | | | | | 75 | | | | | 80 | | |
| tgg | att | tcc | gat | ggc | cag | gta | aaa | gac | ttc | tat | ctg | tat | ccg | ggg | aaa | 288 |
| Trp | Ile | Ser | Asp | Gly | Gln | Val | Lys | Asp | Phe | Tyr | Leu | Tyr | Pro | Gly | Lys | |
| | | | | 85 | | | | | 90 | | | | | 95 | | |
| tat | acc | ttt | gtc | gaa | acg | gct | gca | cct | gac | ggc | tat | gag | gtt | gca | acc | 336 |
| Tyr | Thr | Phe | Val | Glu | Thr | Ala | Ala | Pro | Asp | Gly | Tyr | Glu | Val | Ala | Thr | |
| | | | 100 | | | | | 105 | | | | | 110 | | | |
| gcc | atc | aca | ttc | acg | gtt | aac | gaa | cag | ggt | cag | gta | acc | gtc | aat | ggc | 384 |
| Ala | Ile | Thr | Phe | Thr | Val | Asn | Glu | Gln | Gly | Gln | Val | Thr | Val | Asn | Gly | |
| | | 115 | | | | | 120 | | | | | 125 | | | | |
| aaa | gcg | act | aaa | ggc | gat | gcg | cat | att | gag | aat | ctg | tac | ttt | caa | ggc | 432 |
| Lys | Ala | Thr | Lys | Gly | Asp | Ala | His | Ile | Glu | Asn | Leu | Tyr | Phe | Gln | Gly | |
| | 130 | | | | | 135 | | | | | 140 | | | | | |
| ggc | gga | ggc | ggg | tct | ggc | ggt | ggt | ggt | tcg | tct | aga | gct | gaa | act | gtt | 480 |
| Gly | Gly | Gly | Gly | Ser | Gly | Gly | Gly | Gly | Ser | Ser | Arg | Ala | Glu | Thr | Val | |
| 145 | | | | | 150 | | | | | 155 | | | | | 160 | |
| gaa | agt | tgt | tta | gca | aaa | ccc | cat | aca | gaa | aat | tca | ttt | act | aac | gtc | 528 |
| Glu | Ser | Cys | Leu | Ala | Lys | Pro | His | Thr | Glu | Asn | Ser | Phe | Thr | Asn | Val | |
| | | | | 165 | | | | | 170 | | | | | 175 | | |
| tgg | aaa | gac | gac | aaa | act | tta | gat | cgt | tac | gct | aac | tat | gag | ggc | tgt | 576 |
| Trp | Lys | Asp | Asp | Lys | Thr | Leu | Asp | Arg | Tyr | Ala | Asn | Tyr | Glu | Gly | Cys | |
| | | | 180 | | | | | 185 | | | | | 190 | | | |
| ctg | tgg | aat | gct | aca | ggc | gtt | gta | gtt | tgt | act | ggt | gac | gaa | act | cag | 624 |
| Leu | Trp | Asn | Ala | Thr | Gly | Val | Val | Val | Cys | Thr | Gly | Asp | Glu | Thr | Gln | |
| | | 195 | | | | | 200 | | | | | 205 | | | | |
| tgt | tac | ggt | aca | tgg | gtt | cct | att | ggg | ctt | gct | atc | cct | gaa | aat | gag | 672 |
| Cys | Tyr | Gly | Thr | Trp | Val | Pro | Ile | Gly | Leu | Ala | Ile | Pro | Glu | Asn | Glu | |
| | 210 | | | | | 215 | | | | | 220 | | | | | |
| ggt | ggt | ggc | tct | gag | ggt | ggc | ggt | tct | gag | ggt | ggc | ggt | tct | gag | ggt | 720 |
| Gly | Gly | Gly | Ser | Glu | Gly | Gly | Gly | Ser | Glu | Gly | Gly | Gly | Ser | Glu | Gly | |
| 225 | | | | | 230 | | | | | 235 | | | | | 240 | |
| ggc | ggt | act | aaa | cct | cct | gag | tac | ggt | gat | aca | cct | att | ccg | ggc | tat | 768 |
| Gly | Gly | Thr | Lys | Pro | Pro | Glu | Tyr | Gly | Asp | Thr | Pro | Ile | Pro | Gly | Tyr | |
| | | | 245 | | | | | 250 | | | | | 255 | | | |
| act | tat | atc | aac | cct | ctc | gac | ggc | act | tat | ccg | cct | ggt | act | gag | caa | 816 |
| Thr | Tyr | Ile | Asn | Pro | Leu | Asp | Gly | Thr | Tyr | Pro | Pro | Gly | Thr | Glu | Gln | |
| | | 260 | | | | | 265 | | | | | 270 | | | | |
| aac | ccc | gct | aat | cct | aat | cct | tct | ctt | gag | gag | tct | cag | cct | ctt | aat | 864 |

```
                Asn Pro Ala Asn Pro Asn Pro Ser Leu Glu Glu Ser Gln Pro Leu Asn
                            275                 280                 285 act ttc atg ttt cag aat aat agg ttc cga aat agg cag ggg gca tta           912
Thr Phe Met Phe Gln Asn Asn Arg Phe Arg Asn Arg Gln Gly Ala Leu
        290                 295                 300 act gtt tat acg ggc act gtt act caa ggc act gac ccc gtt aaa act           960
Thr Val Tyr Thr Gly Thr Val Thr Gln Gly Thr Asp Pro Val Lys Thr
305                 310                 315                 320 tat tac cag tac act cct gta tca tca aaa gcc atg tat gac gct tac          1008
Tyr Tyr Gln Tyr Thr Pro Val Ser Ser Lys Ala Met Tyr Asp Ala Tyr
                325                 330                 335 tgg aac ggt aaa ttc aga gac tgc gct ttc cat tct ggc ttt aat gag          1056
Trp Asn Gly Lys Phe Arg Asp Cys Ala Phe His Ser Gly Phe Asn Glu
        340                 345                 350 gat cca ttc gtt tgt gaa tat caa ggc caa tcg tct gac ctg cct caa          1104
Asp Pro Phe Val Cys Glu Tyr Gln Gly Gln Ser Ser Asp Leu Pro Gln
        355                 360                 365 cct cct gtc aat gct ggc ggc ggc tct ggt ggt ggt tct ggt ggc ggc          1152
Pro Pro Val Asn Ala Gly Gly Gly Ser Gly Gly Gly Ser Gly Gly Gly
370                 375                 380 tct gag ggt ggt ggc tct gag ggt ggc ggt tct gag ggt ggc ggc tct          1200
Ser Glu Gly Gly Gly Ser Glu Gly Gly Gly Ser Glu Gly Gly Gly Ser
385                 390                 395                 400 gag gga ggc ggt tcc ggt ggt ggc tct ggt tcc ggt gat ttt gat tat          1248
Glu Gly Gly Gly Ser Gly Gly Gly Ser Gly Ser Gly Asp Phe Asp Tyr
                405                 410                 415 gaa aag atg gca aac gct aat aag ggg gct atg acc gaa aat gcc gat          1296
Glu Lys Met Ala Asn Ala Asn Lys Gly Ala Met Thr Glu Asn Ala Asp
        420                 425                 430 gaa aac gcg cta cag tct gac gct aaa ggc aaa ctt gat tct gtc gct          1344
Glu Asn Ala Leu Gln Ser Asp Ala Lys Gly Lys Leu Asp Ser Val Ala
        435                 440                 445 act gat tac ggt gct gct atc gat ggt ttc att ggt gac gtt tcc ggc          1392
Thr Asp Tyr Gly Ala Ala Ile Asp Gly Phe Ile Gly Asp Val Ser Gly
450                 455                 460 ctt gct aat ggt aat ggt gct act ggt gat ttt gct ggc tct aat tcc          1440
Leu Ala Asn Gly Asn Gly Ala Thr Gly Asp Phe Ala Gly Ser Asn Ser
465                 470                 475                 480 caa atg gct caa gtc ggt gac ggt gat aat tca cct tta atg aat aat          1488
Gln Met Ala Gln Val Gly Asp Gly Asp Asn Ser Pro Leu Met Asn Asn
                485                 490                 495 ttc cgt caa tat tta cct tcc ctc cct caa tcg gtt gaa tgt cgc cct          1536
Phe Arg Gln Tyr Leu Pro Ser Leu Pro Gln Ser Val Glu Cys Arg Pro
        500                 505                 510 ttt gtc ttt ggc gct ggt aaa cca tat gaa ttt tct att gat tgt gac          1584
Phe Val Phe Gly Ala Gly Lys Pro Tyr Glu Phe Ser Ile Asp Cys Asp
        515                 520                 525 aaa ata aac tta ttc cgt ggt gtc ttt gcg ttt ctt tta tat gtt gcc          1632
Lys Ile Asn Leu Phe Arg Gly Val Phe Ala Phe Leu Leu Tyr Val Ala
530                 535                 540 acc ttt atg tat gta ttt tct acg ttt gct aac ata ctg cgt aat aag          1680
Thr Phe Met Tyr Val Phe Ser Thr Phe Ala Asn Ile Leu Arg Asn Lys
545                 550                 555                 560 gag tct taa                                                              1689
Glu Ser <210> SEQ ID NO 30
<211> LENGTH: 562
<212> TYPE: PRT
<213> ORGANISM: Artificial Sequence
```

<220> FEATURE:
<223> OTHER INFORMATION: Synthetic Construct

<400> SEQUENCE: 30

```
Glu Phe Met Lys Lys Ile Trp Leu Ala Leu Ala Gly Leu Val Leu Ala
1               5                   10                  15

Phe Ser Ala Ser Ala Gly Ala Met Val Asp Thr Leu Ser Gly Leu Ser
            20                  25                  30

Ser Glu Gln Gly Gln Ser Gly Asp Met Thr Ile Glu Glu Asp Ser Ala
        35                  40                  45

Thr His Ile Lys Phe Ser Lys Arg Asp Glu Asp Gly Lys Glu Leu Ala
    50                  55                  60

Gly Ala Thr Met Glu Leu Arg Asp Ser Ser Gly Lys Thr Ile Ser Thr
65                  70                  75                  80

Trp Ile Ser Asp Gly Gln Val Lys Asp Phe Tyr Leu Tyr Pro Gly Lys
                85                  90                  95

Tyr Thr Phe Val Glu Thr Ala Ala Pro Asp Gly Tyr Glu Val Ala Thr
            100                 105                 110

Ala Ile Thr Phe Thr Val Asn Glu Gln Gly Gln Val Thr Val Asn Gly
        115                 120                 125

Lys Ala Thr Lys Gly Asp Ala His Ile Glu Asn Leu Tyr Phe Gln Gly
    130                 135                 140

Gly Gly Gly Ser Gly Gly Gly Ser Ser Arg Ala Glu Thr Val
145                 150                 155                 160

Glu Ser Cys Leu Ala Lys Pro His Thr Glu Asn Ser Phe Thr Asn Val
                165                 170                 175

Trp Lys Asp Asp Lys Thr Leu Asp Arg Tyr Ala Asn Tyr Glu Gly Cys
            180                 185                 190

Leu Trp Asn Ala Thr Gly Val Val Val Cys Thr Gly Asp Glu Thr Gln
        195                 200                 205

Cys Tyr Gly Thr Trp Val Pro Ile Gly Leu Ala Ile Pro Glu Asn Glu
    210                 215                 220

Gly Gly Gly Ser Glu Gly Gly Ser Glu Gly Gly Ser Glu Gly
225                 230                 235                 240

Gly Gly Thr Lys Pro Pro Glu Tyr Gly Asp Thr Pro Ile Pro Gly Tyr
                245                 250                 255

Thr Tyr Ile Asn Pro Leu Asp Gly Thr Tyr Pro Pro Gly Thr Glu Gln
            260                 265                 270

Asn Pro Ala Asn Pro Asn Pro Ser Leu Glu Glu Ser Gln Pro Leu Asn
        275                 280                 285

Thr Phe Met Phe Gln Asn Asn Arg Phe Arg Asn Arg Gln Gly Ala Leu
    290                 295                 300

Thr Val Tyr Thr Gly Thr Val Thr Gln Gly Thr Asp Pro Val Lys Thr
305                 310                 315                 320

Tyr Tyr Gln Tyr Thr Pro Val Ser Ser Lys Ala Met Tyr Asp Ala Tyr
                325                 330                 335

Trp Asn Gly Lys Phe Arg Asp Cys Ala Phe His Ser Gly Phe Asn Glu
            340                 345                 350

Asp Pro Phe Val Cys Glu Tyr Gln Gly Gln Ser Ser Asp Leu Pro Gln
        355                 360                 365

Pro Pro Val Asn Ala Gly Gly Ser Gly Gly Gly Ser Gly Gly Gly
    370                 375                 380

Ser Glu Gly Gly Gly Ser Glu Gly Gly Gly Ser Glu Gly Gly Gly Ser
385                 390                 395                 400
```

Glu Gly Gly Gly Ser Gly Gly Ser Gly Ser Gly Asp Phe Asp Tyr
                405                 410                 415

Glu Lys Met Ala Asn Ala Asn Lys Gly Ala Met Thr Glu Asn Ala Asp
            420                 425                 430

Glu Asn Ala Leu Gln Ser Asp Ala Lys Gly Lys Leu Asp Ser Val Ala
        435                 440                 445

Thr Asp Tyr Gly Ala Ala Ile Asp Gly Phe Ile Gly Asp Val Ser Gly
    450                 455                 460

Leu Ala Asn Gly Asn Gly Ala Thr Gly Asp Phe Ala Gly Ser Asn Ser
465                 470                 475                 480

Gln Met Ala Gln Val Gly Asp Gly Asp Asn Ser Pro Leu Met Asn Asn
                485                 490                 495

Phe Arg Gln Tyr Leu Pro Ser Leu Pro Gln Ser Val Glu Cys Arg Pro
            500                 505                 510

Phe Val Phe Gly Ala Gly Lys Pro Tyr Glu Phe Ser Ile Asp Cys Asp
        515                 520                 525

Lys Ile Asn Leu Phe Arg Gly Val Phe Ala Phe Leu Leu Tyr Val Ala
    530                 535                 540

Thr Phe Met Tyr Val Phe Ser Thr Phe Ala Asn Ile Leu Arg Asn Lys
545                 550                 555                 560

Glu Ser

<210> SEQ ID NO 31
<211> LENGTH: 5
<212> TYPE: PRT
<213> ORGANISM: Artificial sequence
<220> FEATURE:
<223> OTHER INFORMATION: sortase B recognition domain
<220> FEATURE:
<221> NAME/KEY: MISC_FEATURE
<222> LOCATION: (3)..(3)
<223> OTHER INFORMATION: Xaa is glutamine or lysine
<220> FEATURE:
<221> NAME/KEY: MISC_FEATURE
<222> LOCATION: (5)..(5)
<223> OTHER INFORMATION: Xaa is asparagine or glycine

<400> SEQUENCE: 31

Asn Pro Xaa Thr Xaa
1               5

<210> SEQ ID NO 32
<211> LENGTH: 4
<212> TYPE: PRT
<213> ORGANISM: Artificial Sequence
<220> FEATURE:
<223> OTHER INFORMATION: sortase B bridging domain

<400> SEQUENCE: 32

Gly Gly Gly Gly
1

<210> SEQ ID NO 33
<211> LENGTH: 10
<212> TYPE: PRT
<213> ORGANISM: Artificial Sequence
<220> FEATURE:
<223> OTHER INFORMATION: linker

<400> SEQUENCE: 33

Gly Gly Gly Gly Ser Gly Gly Gly Gly Ser
1               5                   10

<210> SEQ ID NO 34
<211> LENGTH: 13
<212> TYPE: PRT
<213> ORGANISM: Artificial Sequence
<220> FEATURE:
<223> OTHER INFORMATION: SpyTag

<400> SEQUENCE: 34

Ala His Ile Val Met Val Asp Ala Tyr Lys Pro Thr Lys
1               5                   10

<210> SEQ ID NO 35
<211> LENGTH: 16
<212> TYPE: PRT
<213> ORGANISM: Artificial Sequence
<220> FEATURE:
<223> OTHER INFORMATION: SpyTag variant

<400> SEQUENCE: 35

Pro Pro Val Pro Thr Ile Val Met Val Asp Ala Tyr Lys Pro Thr Lys
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: SpyTag variant

<400> SEQUENCE: 36

Arg Pro Cys Tyr Val Ile Val Met Val Asp Ala Tyr Lys Pro Thr Lys
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: SpyTag variant

<400> SEQUENCE: 37

Gly Arg Tyr Ala Trp Ile Val Met Val Asp Ala Tyr Lys Pro Thr Lys
1               5                   10                  15

<210> SEQ ID NO 38
<211> LENGTH: 13
<212> TYPE: PRT
<213> ORGANISM: Artificial Sequence
<220> FEATURE:
<223> OTHER INFORMATION: SpyTag variant

<400> SEQUENCE: 38

Val Pro Thr Ile Val Met Val Asp Cys Tyr Lys Arg Tyr
1               5                   10

<210> SEQ ID NO 39
<211> LENGTH: 13
<212> TYPE: PRT
<213> ORGANISM: Artificial Sequence
<220> FEATURE:
<223> OTHER INFORMATION: SpyTag variant

<400> SEQUENCE: 39

Val Pro Thr Ile Val Met Val Asp Cys Cys Leu Phe Cys
1               5                   10

```
<210> SEQ ID NO 40
<211> LENGTH: 13
<212> TYPE: PRT
<213> ORGANISM: Artificial Sequence
<220> FEATURE:
<223> OTHER INFORMATION: SpyTag variant

<400> SEQUENCE: 40

Val Pro Thr Ile Val Met Val Asp Phe Trp Met Arg Cys
1               5                   10

<210> SEQ ID NO 41
<211> LENGTH: 13
<212> TYPE: PRT
<213> ORGANISM: Artificial Sequence
<220> FEATURE:
<223> OTHER INFORMATION: SpyTag variant

<400> SEQUENCE: 41

Val Pro Thr Ile Val Met Val Asp Cys Arg Leu Asp Ser
1               5                   10

<210> SEQ ID NO 42
<211> LENGTH: 13
<212> TYPE: PRT
<213> ORGANISM: Artificial Sequence
<220> FEATURE:
<223> OTHER INFORMATION: SpyTag variant

<400> SEQUENCE: 42

Val Pro Thr Ile Val Met Val Asp Cys Gln Leu Ala Ser
1               5                   10

<210> SEQ ID NO 43
<211> LENGTH: 13
<212> TYPE: PRT
<213> ORGANISM: Artificial Sequence
<220> FEATURE:
<223> OTHER INFORMATION: SpyTag variant

<400> SEQUENCE: 43

Val Pro Thr Ile Val Met Val Asp Cys Ser Leu Ser Pro
1               5                   10

<210> SEQ ID NO 44
<211> LENGTH: 13
<212> TYPE: PRT
<213> ORGANISM: Artificial Sequence
<220> FEATURE:
<223> OTHER INFORMATION: SpyTag variant

<400> SEQUENCE: 44

Val Pro Thr Ile Val Met Val Asp Pro Tyr Gln Gly Thr
1               5                   10

<210> SEQ ID NO 45
<211> LENGTH: 13
<212> TYPE: PRT
<213> ORGANISM: Artificial Sequence
<220> FEATURE:
<223> OTHER INFORMATION: SpyTag variant

<400> SEQUENCE: 45

Val Pro Thr Ile Val Met Val Asp Tyr Pro Ser Arg Cys
1               5                   10
```

```
<210> SEQ ID NO 46
<211> LENGTH: 13
<212> TYPE: PRT
<213> ORGANISM: Artificial Sequence
<220> FEATURE:
<223> OTHER INFORMATION: SpyTag variant

<400> SEQUENCE: 46

Val Pro Thr Ile Val Met Val Asp Cys Tyr Lys Arg Tyr
1               5                   10

<210> SEQ ID NO 47
<211> LENGTH: 13
<212> TYPE: PRT
<213> ORGANISM: Artificial Sequence
<220> FEATURE:
<223> OTHER INFORMATION: SpyTag variant

<400> SEQUENCE: 47

Val Pro Thr Ile Val Met Val Asp Phe Ile Leu Ala Asn
1               5                   10

<210> SEQ ID NO 48
<211> LENGTH: 14
<212> TYPE: PRT
<213> ORGANISM: Artificial Sequence
<220> FEATURE:
<223> OTHER INFORMATION: SpyTag variant

<400> SEQUENCE: 48

Val Pro Thr Ile Val Met Val Asp Ala Tyr Lys Arg Tyr Lys
1               5                   10
```